(12) United States Patent
Cauller et al.

(10) Patent No.: US 8,457,757 B2
(45) Date of Patent: Jun. 4, 2013

(54) IMPLANTABLE TRANSPONDER SYSTEMS AND METHODS

(75) Inventors: Larry Cauller, Plano, TX (US);
Richard Weiner, Dallas, TX (US)

(73) Assignee: Micro Transponder, Inc., Austin, TX (US)

( * ) Notice: Subject to any disclaimer, the term of this patent is extended or adjusted under 35 U.S.C. 154(b) by 0 days.

(21) Appl. No.: 12/323,854

(22) Filed: Nov. 26, 2008

(65) Prior Publication Data

US 2009/0157147 A1 Jun. 18, 2009

Related U.S. Application Data

(60) Provisional application No. 60/990,278, filed on Nov. 26, 2007.

(51) Int. Cl.
*A61N 1/36* (2006.01)

(52) U.S. Cl.
USPC .............................................. 607/61

(58) Field of Classification Search
USPC .............................................. 607/61
See application file for complete search history.

(56) References Cited

U.S. PATENT DOCUMENTS

| | | | |
|---|---|---|---|
| 2,641,259 A | 6/1953 | Bartrow | |
| 3,750,653 A | 8/1973 | Simon | |
| 3,796,221 A | 3/1974 | Hagfors | |
| 3,830,242 A | 8/1974 | Greatbatch | |
| 3,885,211 A * | 5/1975 | Gutai | 320/108 |
| 3,893,462 A | 7/1975 | Manning | |
| 3,942,535 A | 3/1976 | Schulman | |
| 4,019,519 A | 4/1977 | Geerling | |
| 4,044,775 A | 8/1977 | McNichols | |
| 4,154,239 A | 5/1979 | Turley | |
| 4,167,179 A | 9/1979 | Kirsch | |
| 4,361,153 A | 11/1982 | Slocum et al. | |
| 4,399,818 A | 8/1983 | Money | |
| 4,541,432 A | 9/1985 | Molina-Negro et al. | |
| 4,592,359 A | 6/1986 | Galbraith | |
| 4,612,934 A | 9/1986 | Borkan | |
| 4,661,103 A | 4/1987 | Harman | |
| 4,723,536 A | 2/1988 | Rauscher et al. | |
| 4,750,499 A | 6/1988 | Hoffer | |
| 4,832,033 A | 5/1989 | Maher et al. | |

(Continued)

FOREIGN PATENT DOCUMENTS

| | | |
|---|---|---|
| CN | 101648053 A | 2/2010 |
| DE | 3405630 C1 | 6/1985 |

(Continued)

OTHER PUBLICATIONS

Bohotin, C., Scholsem, M., Bohotin, V., Franzen, R. and Schoenen, J., "Vagus Nerve Stimulation Attenuates Hear-and Formalin-Induced Pain in Rats", Neuroscience Letters, 2003, vol. 351, pp. 79-82.

(Continued)

*Primary Examiner* — Rex R Holmes
(74) *Attorney, Agent, or Firm* — Conley Rose, P.C.; Grant Rodolph

(57) ABSTRACT

A method and system for providing electrical stimulation to tissue includes implanting one or more battery-free microtransponders having spiral antennas into tissue. Energy is provided wirelessly to the plurality of microtransponders. Tissue is stimulated using the energy.

3 Claims, 36 Drawing Sheets

U.S. PATENT DOCUMENTS

| | | | |
|---|---|---|---|
| 4,883,067 A | 11/1989 | Knispel et al. | |
| 4,902,987 A | 2/1990 | Albright | |
| 4,932,405 A | 6/1990 | Peeters et al. | |
| 4,977,895 A | 12/1990 | Tannenbaum | |
| 5,192,285 A | 3/1993 | Bolscher | |
| 5,193,539 A * | 3/1993 | Schulman et al. | 607/61 |
| 5,193,540 A | 3/1993 | Schulman et al. | |
| 5,222,494 A | 6/1993 | Baker, Jr. | |
| 5,234,316 A | 8/1993 | Rupprecht | |
| 5,250,026 A | 10/1993 | Ehrlich et al. | |
| 5,265,624 A | 11/1993 | Bowman | |
| 5,279,554 A | 1/1994 | Turley | |
| 5,288,291 A | 2/1994 | Teoh | |
| 5,312,439 A | 5/1994 | Loeb | |
| 5,324,316 A | 6/1994 | Schulman et al. | |
| 5,330,515 A | 7/1994 | Rutecki et al. | |
| 5,335,657 A | 8/1994 | Terry, Jr. et al. | |
| 5,363,858 A | 11/1994 | Farwell | |
| 5,405,367 A | 4/1995 | Schulman et al. | |
| 5,474,082 A | 12/1995 | Junker | |
| 5,559,507 A | 9/1996 | Beigel | |
| 5,571,148 A | 11/1996 | Loeb et al. | |
| 5,593,432 A | 1/1997 | Crowther et al. | |
| 5,662,689 A | 9/1997 | Elsberry et al. | |
| 5,735,887 A | 4/1998 | Barreras, Sr. et al. | |
| 5,741,316 A | 4/1998 | Chen et al. | |
| 5,755,747 A | 5/1998 | Daly et al. | |
| 5,776,170 A | 7/1998 | MacDonald et al. | |
| 5,779,665 A | 7/1998 | Mastrototaro et al. | |
| 5,782,874 A | 7/1998 | Loos | |
| 5,785,680 A | 7/1998 | Niezink et al. | |
| 5,800,458 A | 9/1998 | Wingrove | |
| 5,814,092 A | 9/1998 | King | |
| 5,833,603 A | 11/1998 | Kovacs et al. | |
| 5,833,714 A | 11/1998 | Loeb | |
| 5,871,512 A | 2/1999 | Hemming et al. | |
| 5,899,922 A | 5/1999 | Loos | |
| 5,913,882 A | 6/1999 | King | |
| 5,938,690 A | 8/1999 | Law et al. | |
| 5,945,938 A | 8/1999 | Chia et al. | |
| 5,954,758 A | 9/1999 | Peckham et al. | |
| 5,957,958 A | 9/1999 | Schulman et al. | |
| 5,970,398 A | 10/1999 | Tuttle | |
| 6,009,350 A | 12/1999 | Renken | |
| 6,051,017 A | 4/2000 | Loeb et al. | |
| 6,141,588 A | 10/2000 | Cox et al. | |
| 6,164,284 A | 12/2000 | Schulman et al. | |
| 6,175,764 B1 | 1/2001 | Loeb et al. | |
| 6,181,965 B1 | 1/2001 | Loeb et al. | |
| 6,181,969 B1 | 1/2001 | Gord | |
| 6,185,452 B1 | 2/2001 | Schulman et al. | |
| 6,185,455 B1 | 2/2001 | Loeb et al. | |
| 6,201,980 B1 | 3/2001 | Darrow et al. | |
| 6,208,894 B1 | 3/2001 | Schulman et al. | |
| 6,208,902 B1 | 3/2001 | Boveja | |
| 6,214,032 B1 | 4/2001 | Loeb et al. | |
| 6,221,908 B1 | 4/2001 | Kilgard et al. | |
| 6,240,316 B1 | 5/2001 | Richmond et al. | |
| 6,263,247 B1 | 7/2001 | Mueller et al. | |
| 6,270,472 B1 | 8/2001 | Antaki et al. | |
| 6,308,102 B1 | 10/2001 | Sieracki et al. | |
| 6,339,725 B1 | 1/2002 | Naritoku et al. | |
| 6,345,202 B2 | 2/2002 | Richmond et al. | |
| 6,354,989 B1 | 3/2002 | Nudeshima | |
| 6,366,814 B1 | 4/2002 | Boveja et al. | |
| 6,394,947 B1 | 5/2002 | Leysieffer | |
| 6,409,655 B1 | 6/2002 | Wilson et al. | |
| 6,415,184 B1 | 7/2002 | Ishikawa et al. | |
| 6,430,443 B1 | 8/2002 | Karell | |
| 6,430,444 B1 | 8/2002 | Borza | |
| 6,447,448 B1 | 9/2002 | Ishikawa et al. | |
| 6,456,866 B1 | 9/2002 | Tyler et al. | |
| 6,458,157 B1 | 10/2002 | Suaning | |
| 6,463,328 B1 | 10/2002 | John | |
| 6,480,730 B2 | 11/2002 | Darrow et al. | |
| 6,505,075 B1 | 1/2003 | Weiner | |
| 6,516,808 B2 | 2/2003 | Schulman | |
| 6,546,290 B1 | 4/2003 | Shloznikov | |
| 6,567,689 B2 | 5/2003 | Burbank et al. | |
| 6,572,543 B1 | 6/2003 | Christopherson et al. | |
| 6,582,441 B1 | 6/2003 | He et al. | |
| 6,585,644 B2 | 7/2003 | Lebel et al. | |
| 6,591,139 B2 | 7/2003 | Loftin et al. | |
| 6,592,518 B2 | 7/2003 | Denker et al. | |
| 6,626,676 B2 | 9/2003 | Freer | |
| 6,650,943 B1 | 11/2003 | Whitehurst et al. | |
| 6,658,297 B2 | 12/2003 | Loeb | |
| 6,658,301 B2 | 12/2003 | Loeb et al. | |
| 6,676,675 B2 | 1/2004 | Mallapragada et al. | |
| 6,690,974 B2 | 2/2004 | Archer et al. | |
| 6,695,885 B2 | 2/2004 | Schulman et al. | |
| 6,712,753 B2 | 3/2004 | Manne | |
| 6,721,603 B2 | 4/2004 | Zabara et al. | |
| 6,731,979 B2 | 5/2004 | Mac Donald | |
| 6,733,485 B1 | 5/2004 | Whitehurst et al. | |
| 6,735,474 B1 | 5/2004 | Loeb et al. | |
| 6,735,475 B1 * | 5/2004 | Whitehurst et al. | 607/46 |
| 6,760,626 B1 | 7/2004 | Boveja | |
| 6,788,975 B1 | 9/2004 | Whitehurst et al. | |
| 6,796,935 B1 | 9/2004 | Savino | |
| 6,804,561 B2 | 10/2004 | Stover | |
| 6,829,508 B2 | 12/2004 | Schulman et al. | |
| 6,832,114 B1 | 12/2004 | Whitehurst et al. | |
| 6,836,685 B1 | 12/2004 | Fitz | |
| 6,844,023 B2 | 1/2005 | Schulman et al. | |
| 6,845,267 B2 | 1/2005 | Harrison et al. | |
| 6,855,115 B2 | 2/2005 | Fonseca et al. | |
| 6,871,099 B1 | 3/2005 | Whitehurst et al. | |
| 6,885,888 B2 | 4/2005 | Rezai | |
| 6,895,279 B2 | 5/2005 | Loeb et al. | |
| 6,895,280 B2 | 5/2005 | Meadows et al. | |
| 6,941,171 B2 | 9/2005 | Mann et al. | |
| 6,971,984 B2 | 12/2005 | Ardizzone | |
| 6,974,437 B2 | 12/2005 | Lebel et al. | |
| 6,990,337 B2 | 1/2006 | ONeill et al. | |
| 7,003,352 B1 | 2/2006 | Whitehurst | |
| 7,006,870 B1 | 2/2006 | Whitehurst et al. | |
| 7,006,875 B1 | 2/2006 | Kuzma et al. | |
| 7,013,177 B1 | 3/2006 | Whitehurst et al. | |
| 7,024,247 B2 | 4/2006 | Gliner et al. | |
| 7,027,860 B2 | 4/2006 | Bruninga et al. | |
| 7,054,689 B1 | 5/2006 | Whitehurst et al. | |
| 7,054,691 B1 | 5/2006 | Kuzma et al. | |
| 7,062,330 B1 | 6/2006 | Boveja et al. | |
| 7,076,307 B2 | 7/2006 | Boveja et al. | |
| 7,103,408 B2 | 9/2006 | Haller et al. | |
| 7,107,103 B2 | 9/2006 | Schulman et al. | |
| 7,114,502 B2 | 10/2006 | Schulman et al. | |
| 7,117,034 B2 | 10/2006 | Kronberg | |
| 7,132,173 B2 | 11/2006 | Daulton | |
| 7,146,217 B2 | 12/2006 | Firlik et al. | |
| 7,147,604 B1 | 12/2006 | Allen et al. | |
| 7,149,574 B2 | 12/2006 | Yun et al. | |
| 7,155,279 B2 | 12/2006 | Whitehurst et al. | |
| 7,174,215 B2 | 2/2007 | Bradley | |
| 7,184,837 B2 | 2/2007 | Goetz | |
| 7,187,968 B2 | 3/2007 | Wolf et al. | |
| 7,191,012 B2 | 3/2007 | Boveja et al. | |
| 7,194,007 B1 | 3/2007 | Beadle et al. | |
| 7,209,787 B2 | 4/2007 | DiLorenzo | |
| 7,209,788 B2 | 4/2007 | Nicolelis et al. | |
| 7,209,792 B1 | 4/2007 | Parramon et al. | |
| 7,211,048 B1 | 5/2007 | Najafi et | |
| 7,212,110 B1 | 5/2007 | Martin et | |
| 7,212,866 B1 | 5/2007 | Griffith | |
| 7,221,981 B2 | 5/2007 | Gliner | |
| 7,231,256 B2 | 6/2007 | Wahlstrand et al. | |
| 7,236,822 B2 | 6/2007 | Dobak, III | |
| 7,236,830 B2 | 6/2007 | Gliner | |
| 7,236,831 B2 | 6/2007 | Firlik et al. | |
| 7,256,695 B2 | 8/2007 | Hamel et al. | |
| 7,290,890 B2 | 11/2007 | Yoshida et al. | |
| 7,292,890 B2 | 11/2007 | Whitehurst et al. | |
| 7,299,096 B2 | 11/2007 | Balzer et al. | |
| 7,302,298 B2 | 11/2007 | Lowry et al. | |
| 7,305,268 B2 | 12/2007 | Gliner et al. | |
| 7,324,852 B2 | 1/2008 | Barolat et al. | |

| Patent No. | Date | Name |
|---|---|---|
| 7,328,069 B2 | 2/2008 | Gerber |
| 7,330,756 B2 | 2/2008 | Marnfeldt |
| 7,337,004 B2 | 2/2008 | Classen et al. |
| 7,353,064 B2 | 4/2008 | Gliner et al. |
| 7,359,751 B1 | 4/2008 | Erickson et al. |
| 7,361,135 B2 | 4/2008 | Drobnik et al. |
| 7,369,897 B2 | 5/2008 | Boveja et al. |
| 7,373,204 B2 | 5/2008 | Gelfand et al. |
| 7,384,403 B2 | 6/2008 | Sherman |
| 7,386,348 B2 | 6/2008 | North et al. |
| 7,389,145 B2 | 6/2008 | Kilgore et al. |
| 7,406,105 B2 | 7/2008 | DelMain et al. |
| 7,437,195 B2 | 10/2008 | Policker et al. |
| 7,437,196 B2 | 10/2008 | Wyler et al. |
| 7,463,927 B1 | 12/2008 | Chaouat |
| 7,481,771 B2 | 1/2009 | Fonseca et al. |
| 7,483,747 B2 | 1/2009 | Gliner et al. |
| 7,489,561 B2 | 2/2009 | Armstrong et al. |
| 7,489,966 B2 | 2/2009 | Leinders et al. |
| 7,493,172 B2 | 2/2009 | Whitehurst et al. |
| 7,526,341 B2 | 4/2009 | Goetz et al. |
| 7,529,582 B1 | 5/2009 | DiLorenzo |
| 7,542,804 B2 | 6/2009 | Mandell |
| 7,547,353 B2 | 6/2009 | Reyes et al. |
| 7,555,344 B2 | 6/2009 | Maschino et al. |
| 7,555,345 B2 | 6/2009 | Wahlstrand et al. |
| 7,555,347 B2 | 6/2009 | Loeb |
| 7,558,631 B2 | 7/2009 | Cowan et al. |
| 7,563,279 B2 | 7/2009 | Lasater |
| 7,565,199 B2 | 7/2009 | Sheffield et al. |
| 7,565,200 B2 | 7/2009 | Wyler et al. |
| 7,577,481 B2 | 8/2009 | Firlik et al. |
| 7,590,454 B2 | 9/2009 | Garabedian et al. |
| 7,593,776 B2 | 9/2009 | Loeb et al. |
| 7,596,413 B2 | 9/2009 | Libbus et al. |
| 7,603,174 B2 | 10/2009 | De Ridder |
| 7,603,178 B2 | 10/2009 | North et al. |
| 7,613,519 B2 | 11/2009 | DeRidder |
| 7,613,520 B2 | 11/2009 | DeRidder |
| 7,616,990 B2 | 11/2009 | Chavan et al. |
| 7,630,771 B2 | 12/2009 | Cauller |
| 7,634,317 B2 | 12/2009 | Ben-David et al. |
| 7,636,603 B1 | 12/2009 | Overstreet et al. |
| 7,715,915 B1 | 5/2010 | Ryu et al. |
| 7,765,013 B2 | 7/2010 | Blick et al. |
| 7,769,466 B2 | 8/2010 | Denker et al. |
| 7,786,867 B2 | 8/2010 | Hamel et al. |
| 7,801,615 B2 | 9/2010 | Meadows et al. |
| 7,822,480 B2 | 10/2010 | Park et al. |
| 2001/0016683 A1 | 8/2001 | Darrow et al. |
| 2002/0022872 A1 | 2/2002 | Gielen et al. |
| 2002/0029005 A1 | 3/2002 | Levendowski et al. |
| 2002/0051806 A1 | 5/2002 | Mallapragada et al. |
| 2002/0058853 A1 | 5/2002 | Kaplan |
| 2002/0077672 A1 | 6/2002 | Govari et al. |
| 2002/0193845 A1 | 12/2002 | Greenberg et al. |
| 2003/0004411 A1 | 1/2003 | Govari et al. |
| 2003/0013948 A1 | 1/2003 | Russell |
| 2003/0014091 A1 | 1/2003 | Rastegar et al. |
| 2003/0114899 A1* | 6/2003 | Woods et al. ............ 607/60 |
| 2003/0139677 A1 | 7/2003 | Fonseca et al. |
| 2003/0139783 A1* | 7/2003 | Kilgore et al. ............ 607/49 |
| 2003/0144709 A1 | 7/2003 | Zabara et al. |
| 2003/0171758 A1 | 9/2003 | Gibson et al. |
| 2003/0225331 A1 | 12/2003 | Diederich et al. |
| 2004/0031065 A1 | 2/2004 | Barth |
| 2004/0172075 A1 | 9/2004 | Shafer et al. |
| 2004/0172083 A1 | 9/2004 | Penner |
| 2004/0176831 A1 | 9/2004 | Gliner et al. |
| 2004/0181261 A1 | 9/2004 | Manne |
| 2004/0253209 A1 | 12/2004 | Soykan et al. |
| 2004/0267152 A1 | 12/2004 | Pineda |
| 2005/0015014 A1 | 1/2005 | Fonseca et al. |
| 2005/0021100 A1 | 1/2005 | Tsukamoto et al. |
| 2005/0070974 A1 | 3/2005 | Knudson et al. |
| 2005/0131386 A1 | 6/2005 | Freeman et al. |
| 2005/0137652 A1 | 6/2005 | Cauller et al. |
| 2005/0143789 A1 | 6/2005 | Whitehurst et al. |
| 2005/0209667 A1 | 9/2005 | Erickson et al. |
| 2005/0222641 A1 | 10/2005 | Pless |
| 2005/0245989 A1 | 11/2005 | Davis |
| 2005/0256551 A1 | 11/2005 | Schulman et al. |
| 2005/0258242 A1 | 11/2005 | Zarembo |
| 2006/0058570 A1 | 3/2006 | Rapach et al. |
| 2006/0173263 A1 | 8/2006 | He et al. |
| 2006/0173493 A1 | 8/2006 | Armstrong et al. |
| 2006/0195154 A1 | 8/2006 | Jaax et al. |
| 2006/0206149 A1 | 9/2006 | Yun |
| 2006/0224214 A1 | 10/2006 | Koller et al. |
| 2006/0241354 A1 | 10/2006 | Allen |
| 2006/0247719 A1 | 11/2006 | Maschino et al. |
| 2006/0271110 A1 | 11/2006 | Vernon et al. |
| 2007/0010809 A1 | 1/2007 | Hovda et al. |
| 2007/0021786 A1 | 1/2007 | Parnis et al. |
| 2007/0027486 A1 | 2/2007 | Armstrong |
| 2007/0027504 A1 | 2/2007 | Barrett et al. |
| 2007/0032734 A1 | 2/2007 | Najafi et al. |
| 2007/0077265 A1 | 4/2007 | Klueh et al. |
| 2007/0123938 A1 | 5/2007 | Haller et al. |
| 2007/0179534 A1 | 8/2007 | Firlik et al. |
| 2007/0191908 A1 | 8/2007 | Jacob et al. |
| 2007/0225767 A1 | 9/2007 | Daly et al. |
| 2007/0265172 A1 | 11/2007 | Patel et al. |
| 2007/0265683 A1 | 11/2007 | Ehrlich |
| 2007/0275035 A1 | 11/2007 | Herman et al. |
| 2007/0293908 A1 | 12/2007 | Cowan et al. |
| 2008/0033351 A1 | 2/2008 | Trogden et al. |
| 2008/0033502 A1 | 2/2008 | Harris et al. |
| 2008/0058892 A1 | 3/2008 | Haefner et al. |
| 2008/0065182 A1 | 3/2008 | Strother et al. |
| 2008/0084898 A1 | 4/2008 | Miyaho et al. |
| 2008/0084911 A1 | 4/2008 | Yerlikaya |
| 2008/0084941 A1 | 4/2008 | Mohanty et al. |
| 2008/0084951 A1 | 4/2008 | Chen et al. |
| 2008/0084972 A1 | 4/2008 | Burke et al. |
| 2008/0084986 A1 | 4/2008 | Kumarasamy et al. |
| 2008/0103548 A1 | 5/2008 | Fowler et al. |
| 2008/0109046 A1 | 5/2008 | Lima et al. |
| 2008/0243204 A1 | 10/2008 | Uthman et al. |
| 2008/0259681 A1 | 10/2008 | Branch et al. |
| 2008/0275369 A1 | 11/2008 | Fandriks |
| 2008/0281210 A1 | 11/2008 | Nunez et al. |
| 2008/0281212 A1 | 11/2008 | Nunez et al. |
| 2008/0281368 A1 | 11/2008 | Bulkes et al. |
| 2008/0319506 A1 | 12/2008 | Cauller |
| 2009/0015331 A1 | 1/2009 | Segarra |
| 2009/0024042 A1 | 1/2009 | Nunez et al. |
| 2009/0024189 A1 | 1/2009 | Lee et al. |
| 2009/0030476 A1 | 1/2009 | Hargrove |
| 2009/0049321 A1 | 2/2009 | Balatsos et al. |
| 2009/0132003 A1 | 5/2009 | Borgens et al. |
| 2009/0149918 A1 | 6/2009 | Krulevitch et al. |
| 2009/0157142 A1 | 6/2009 | Cauller |
| 2009/0157145 A1 | 6/2009 | Cauller |
| 2009/0157150 A1 | 6/2009 | Cauller |
| 2009/0157151 A1 | 6/2009 | Cauller et al. |
| 2009/0163889 A1 | 6/2009 | Cauller et al. |
| 2009/0198293 A1 | 8/2009 | Cauller et al. |
| 2009/0209804 A1 | 8/2009 | Seiler et al. |
| 2009/0216115 A1 | 8/2009 | Seiler et al. |
| 2009/0247939 A1 | 10/2009 | Rue et al. |
| 2009/0264813 A1 | 10/2009 | Chang |
| 2009/0292325 A1 | 11/2009 | Cederna et al. |
| 2009/0312594 A1 | 12/2009 | Lamoureux et al. |
| 2010/0003656 A1 | 1/2010 | Kilgard et al. |
| 2010/0004705 A1 | 1/2010 | Kilgard et al. |
| 2010/0004717 A1 | 1/2010 | Kilgard et al. |
| 2010/0022908 A1 | 1/2010 | Cauller |
| 2010/0036211 A1 | 2/2010 | La Rue et al. |
| 2010/0036445 A1 | 2/2010 | Sakai et al. |
| 2010/0057160 A1 | 3/2010 | De Ridder |
| 2010/0063564 A1 | 3/2010 | Libbus et al. |
| 2010/0069992 A1 | 3/2010 | Aghassian et al. |
| 2010/0069994 A1 | 3/2010 | Cauller |
| 2010/0100010 A1 | 4/2010 | Andarawis et al. |
| 2010/0100079 A1 | 4/2010 | Berkcan et al. |
| 2010/0106217 A1 | 4/2010 | Colborn |
| 2010/0125314 A1 | 5/2010 | Bradley et al. |

| | | | |
|---|---|---|---|
| 2010/0137961 | A1 | 6/2010 | Moffitt et al. |
| 2010/0145216 | A1 | 6/2010 | He et al. |
| 2010/0145401 | A1 | 6/2010 | Pastore et al. |
| 2010/0174341 | A1 | 7/2010 | Bolea et al. |
| 2010/0222844 | A1 | 9/2010 | Troosters et al. |
| 2010/0331921 | A1 | 12/2010 | Bornzin et al. |
| 2011/0004266 | A1 | 1/2011 | Sharma |

FOREIGN PATENT DOCUMENTS

| | | |
|---|---|---|
| DE | 2004050616 B3 | 3/2006 |
| DE | 112008001669 T5 | 5/2010 |
| DE | 11208003192 T5 | 10/2010 |
| DE | 11208003194 T5 | 2/2011 |
| DE | 11208003180 T5 | 3/2011 |
| EP | 0247649 A1 | 2/1987 |
| EP | 1575665 A1 | 9/2005 |
| EP | 1719540 A3 | 8/2006 |
| EP | 1785160 A2 | 5/2007 |
| WO | 96/19257 A1 | 6/1996 |
| WO | 98/17628 A2 | 4/1998 |
| WO | 98/43701 A1 | 10/1998 |
| WO | 02/082982 A1 | 10/2002 |
| WO | 03/003791 A1 | 1/2003 |
| WO | 03/015863 A2 | 2/2003 |
| WO | 03/018113 A1 | 3/2003 |
| WO | 03/076010 A1 | 9/2003 |
| WO | 2004060144 A2 | 7/2004 |
| WO | 2005061045 A1 | 7/2005 |
| WO | 2005067792 A1 | 7/2005 |
| WO | 2006020377 A2 | 2/2006 |
| WO | 2006029007 A2 | 3/2006 |
| WO | 2006029257 A2 | 3/2006 |
| WO | 2006091611 A1 | 8/2006 |
| WO | 2007073557 A2 | 6/2007 |
| WO | 2007098202 A3 | 8/2007 |
| WO | 2007106692 A2 | 9/2007 |
| WO | 2007136657 A2 | 11/2007 |
| WO | 2007146213 A2 | 12/2007 |
| WO | 2008103977 A2 | 8/2008 |
| WO | 2008133797 A1 | 11/2008 |
| WO | 2008150348 A1 | 12/2008 |
| WO | 2008151059 A2 | 12/2008 |
| WO | 2009018172 A2 | 2/2009 |
| WO | 2009035515 A1 | 3/2009 |
| WO | 2009070697 A2 | 6/2009 |
| WO | 2009070709 A1 | 6/2009 |
| WO | 2009070715 A2 | 6/2009 |
| WO | 2009070719 A1 | 6/2009 |
| WO | 2009070738 A1 | 6/2009 |
| WO | 2009070705 A1 | 9/2009 |
| WO | 2009110935 A1 | 9/2009 |
| WO | 2009111012 A1 | 9/2009 |
| WO | 2009015104 A2 | 12/2009 |
| WO | 2010002936 A2 | 1/2010 |
| WO | 2010022071 A2 | 2/2010 |
| WO | 2010124321 A1 | 11/2010 |

OTHER PUBLICATIONS

Bohotin, C., Scholsem, M., Multon, S., Martin D., Bohotin, V., Schoenen, J., Vagus Nerve Stimulation in Awake Rats Reduces Formalin-Induced Nociceptive Behavior and Fos-Immunoreactivity in Trigeminal Nucleus Caudalis, Pain 101, 2003, pp. 3-12.

Burridge, J. and Etherington, R., "A Preliminary Clinical Study using RF BION Microstimulators to Facilitate Upper Limb Function in Hemiplegia", Advances in Clinical Neurosciences and Rehabilitation, May/Jun. 2004, vol. 4, pp. 26-27.

Cauller, L. and Lee, J., "In Vivo Tests of Switched-Capacitor Neural Stimulation for Use in Minimally-Invasive Wireless Implants", IEEE International Symposium on Circuits and Systems, 2008, 2 pages.

Chuang, H., "Numerical Computation of Fat Layer Effects on Microwave Near-Field Radiation to the Abdomen of a Full-Scale Human Body Model", IEEE Transactions on Microwave Theory and Techniques, vol. 45, Jan. 1997, pp. 118-125.

Cogan, S., "Neural Stimulation and Recording Electrodes" Annual Review of Biomedical Engineering, vol. 1, 2008, pp. 275-309.

Ghovanloo, M., "A Switched-Capacitor Based Neurostimulating System for Low-Power Wireless Microstimulating Systems", IEEE International Symposium on Circuits and Systems, May 2006, pp. 2197-2220.

Gopalkrishnan, P. and Sluka, K., "Effect of Varying Frequency, Intensity, and Pulse Duration of Transcutaneous Electrical Nerve Stimulation on Primary Hyperalgesia in Inflamed Rats", The American Congress of Rehabilitation Medicine and the American Academy of Physical Medicine and Rehabilitation, vol. 81, Jul. 2000, pp. 984-990.

Goroszeniuk, T., Kothari, S. and Hamann, W., "Subcutaneous Neuromodulating Implant Targeted at the Site of Pain", Regional Anesthesia and Pain Medicine, vol. 31, No. 2, Mar./Apr. 2006, pp. 168-171.

Huang et al., "A 0.5-mW Passive Telemetry IC for Biomedical Applications", IEEE Journal of Solid-State Circuits, vol. 33, No. 7, Jul. 1998, pp. 937-946.

Kilgore, K., Bhadra, N. and Snyder, J., "Treatment of Neuroma Pain Using High Frequency Alternating Current" poster, 1 page.

Kipke, D., Vetter, R., Williams, J., and Hetke, J., "Silicon-Substrate Intracortical Microelectrode Arrays for Long-Term Recording of Neuronal Spike Activity in Cerebral Cortex", IEEE Transactions on Neural Systems and Rehabilitation Engineering, vol. 11, No. 2, Jun. 2003, pp. 151-155.

Li, C., and Bak, A., "Excitability Characteristics of the A- and C-Fibers in a Peripheral Nerve", Experimental Neurology, vol. 50, 1976, pp. 67-79.

Mendlin, A., Martin F.J., A. and Jacobs, B., "Dopaminergic Input is Required for Increases in Serotonin Output Produced by Behavioral Activation: An In Vivo Microdialysis Study in Rat Forebrain", Neuroscience, vol. 93, No. 3, 1999, pp. 897-905.

Millard, R. and Shepherd, R., "A Fully Implantable Stimulator for use in Small Laboratory Animals", Journal of Neuroscience Methods, 2007, pp. 168-177.

Parikh, V., Pomerleau, F., Huettl, P, Gerhardt, G., Sarter, M. and Bruno, J.P., "Rapid Assessment of in Vivo Cholinergic Transmission by Amperometric Detection of Changes in Extracellular Choline Levels", European Journal of Neuroscience, vol. 20, Jul. 12, 2004, pp. 1545-1554.

Rainov, N., Fels, C., Heidecke, V. and Burkert, W., "Epidural Electrical Stimulation of the Motor Cortex in Patients with Facial Neuralgia", Clinical Neurology and Neurosurgery 99, 1997, pp. 205-209.

Saito, Y., Matida. S., Anami, S. Baba, H., Kinbara, A., Horikoshi, G., and Tanaka, J., "Breakdown of Alumina RF Windows", American Institute of Physics, Rev. Sci. Instrum., vol. 60, No. 7, Jul. 1989, pp. 1736-1740.

Sakai, Y., Nishijima, Y., Mikuni, N. and Iwata, N., "An Experimental Model of Hyper-Irritability in The Trigeminal Skin Field of The Rat", Pain, vol. 7, 1979, pp. 147-157.

Sandkuhler, J., Chen, J., Cheng, G. and Randic, M., "Low-Frequency Stimulation of Afferent Aδ-Fibers Induces Long-Term Depression at Primary Afferent Synapses with Substantia Gelatinosa Neurons in the Rat", The Journal of Neuroscience, vol. 17, Issue 16, Aug. 15, 1997, pp. 6473-6491.

Sandkuhler, J., "Understanding LTP in Pain Pathways", Molecular Pain, vol. 3, Issue 9, Apr. 3, 2007, pp. 1-9.

.Sheng, L., Nishiyama, K., Honda, T., Sugiura, M., Yaginuma, H. and Sugiura, Y., "Suppressive Affects of Neiting Acupuncture on Toothache: An Experimental Analysis on Fos Expression Evoked by Tooth Pulp Stimulation in the Trigeminal Subnucleus Pars Caudalis and the Periaqueductal Gray of Rats", Neuroscience Research, vol. 38, 2000, pp. 331-339.

Simpson, J. and Ghovanloo, M., "An Experimental Study of Voltage, Current, and Charge Controlled Stimulation Front-End Circuitry", IEEE International Symposium on Circuits and Systems, May 2007, pp. 325-328.

Simpson, J., Krishnamurthy, G., Feller, G., Murrow, R., and Ghovanloo, M., "A Switched-Capacitor Based Neurostimulating System for Low-Power Head-Mounted Deep Brain Stimulators", NCBIONICS, North Carolina State University, 1 page.

Spinner, R., "Outcomes for Peripheral Entrapment Syndromes", Clinical Neurosurgery, vol. 53, 2006, pp. 285-294.

Tsodyks, M., "Computational neuroscience grand challenges—a humble attempt at future forecast", Frontiers in NeurosciTSODYKS,M., "Computational neurscience grand challenges—a humble attempt at future forecast", Frontiers in Neuroscience, vol. 2, Jul. 2008, pp. 17-18.ence, vol. 2, July. 2008, pp. 17-18.

Vetter, R., et al., Chronic Neural Recording Using Silicon-Substrate Microelectrode Arrays Implanted in Cerebral Cortex, IEEE Transactions on Biomedical Engineering, vol. 51, No. 6, Jun. 2004, pp. 896-904.

Vuckovic, A. and Rijkhoff, N., "Different Pulse Shapes for Selective Large Fibre Block in Sacral Nerve Roots Using a Technique of Anodal Block: An experimental Study" Medical & Biological Engineering & Computing, vol. 42, 2004, pp. 817-824.

Wever, R. and Hemrika, W., "Vanadium Haloperoxidases", Handbook of Metalloproteins, John Wiley & Sons, Ltd. Chichester, 2001, pp. 1416-1428.

EZstimi II Peripheral Nerve Locator and Stimulator, Model ES400, Operator's Manual, Live-Tech, Inc., 2005, 29 pages.

"Multi-Program Neurostimulator", Implant Manual, Medtronic, 2006, 16 pages.

"Stimuplex Nerve Stimulator" brochure, Braun, 4 pages.

Office Action dated Dec. 22, 2010, 11 pages, U.S. Appl. No. 12/323,904, filed Nov. 26, 2008.

Office Action dated Aug. 29, 2011, 70 pages, U.S. Appl. No. 12/323,904, filed Nov. 26, 2008.

Office Action dated Dec. 2, 2010, 9 pages, U.S. Appl. No. 12/323,934, filed Nov. 26, 2008.

Office Action dated Jul. 15, 2011, 36 pages, U.S. Appl. No. 12/323,934, filed Nov. 28, 2008.

Office Action dated Oct. 4, 2010, 11 pages, U.S. Appl. No. 12/323,952, filed Nov. 26, 2008.

Office Action dated Jul. 9, 2010, 18 pages, U.S. Appl. No. 12/323,952, filed Nov. 26, 2008.

Office Action dated Apr. 19, 2011, 43 pages, U.S. Appl. No. 12/323,952, filed Nov. 26, 2008.

Office Action dated Jan. 19, 2011, 11 pages, U.S. Appl. No. 12/323,969, filed Nov. 26, 2008.

Office Action dated Aug. 30, 2010, 5 pages, U.S. Appl. No. 12/323,969, filed Nov. 26, 2008.

Office Action dated Dec. 9, 2010, 7 pages, U.S. Appl. No. 12/324,000, filed Nov. 26, 2008.

Office Action dated Apr. 28, 2011, 8 pages, U.S. Appl. No. 12/324,000, filed Nov. 26, 2008.

Office Action dated Aug. 1, 2011, 9 pages, U.S. Appl. No. 12/324,044, filed Nov. 26, 2008.

Office Action dated Mar. 10, 2011, 10 pages, U.S. Appl. No. 12/485,040, filed Jun. 15, 2009.

Office Action dated May 5, 2011, 8 pages, U.S. Appl. No. 12/485,860, filed Jun. 16, 2009.

Office Action dated Mar. 10, 2011, 10 pages, U.S. Appl. No. 12/485,857, filed Jun. 15, 2009.

Office Action dated Aug. 23, 2011, 4 pages, U.S. Appl. No. 12/624,383, filed Nov. 23, 2009.

Foreign Communication From a Related Counterpart Application—International Search Report, PCT/US2008/068165, dated Dec. 24, 2008, 3 pages.

Foreign Communication From a Related Counterpart Application—International Search Report, PCT/US2008/084898, dated May 26, 2009, 5 pages.

Foreign Communication From a Related Counterpart Application—Written Opinion PCT/US2008/084898 dated May 26, 2009, 10 pages.

Foreign Communication From a Related Counterpart Application—International Search Report, PCT/US2009/049321, dated Feb. 9, 2010, 8 pages.

Foreign Communication From a Related Counterpart Application—Written Opinion, PCT/US2009/049321, dated Feb. 9, 2010, 2 pages.

Foreign Communication From a Related Counterpart Application—Office Action dated Jul. 6, 2010, Australian Application No. 2008329642, 2 pages.

Foreign Communication From a Related Counterpart Application—Office Action dated Jul. 6, 2010, Australian Application No. 2008329648, 2 pages.

Foreign Communication From a Related Counterpart Application—Office Action dated Jul. 6, 2010, Australian Application No. 2008329652, 2 pages.

Foreign Communication From a Related Counterpart Application—Office Action dated Jul. 6, 2010, Australian Application No. 2008329671, 2 pages.

Foreign Communication From a Related Counterpart Application—Office Action dated Jul. 6, 2010, Australian Application No. 2008329716, 2 pages.

Foreign Communication From a Related Counterpart Application—Office Action dated Jul. 6, 2010, Australian Application No. 2008329724, 2 pages.

Foreign Communication From a Related Counterpart Application—Office Action dated Jul. 6, 2010, Australian Application No. 2008352005, 2 pages.

Foreign Communication from a Related Counterpart Application—Office Action dated Apr. 13, 2011, German Application No. 112008003184.3.

Cauller, Lawrence J.; U.S. Appl. No. 12/611,105; Title: "Short—Pulse Neural Stimulation Systems, Devices and Methods"; Filing Date: Nov. 18, 2009; Specification 10 pgs.; 3 Drawing Sheets (Figs. 1-7).

Cauller, Lawrence J.; U.S. Appl. No. 12/611,110; Title: "Parasthesia Using Short-Pulsed Neural Stimulation Systems, Devices and Methods"; Filing Date: Nov. 2, 2009; Specification 10 pages; 3 Drawing Sheets (Figs. 1-7).

Mokwa et al., "Micro-Transponder Systems for Medical Applications", IEEE Transactions on Instrumentation and Measurement, vol. 50, No. 6, Dec. 2001, pp. 1551-1555.

Nair, S.G. and Gudelsky, G.A., "Effect of a Serotonin Depleting Regimen of 3, 4-Methylenedioxymethamphetamine (MDMA) on the Subsequent Stimulation of Acetylcholine Release in the Rat Prefrontal Cortex", Elsevier Brain Research Bulletin 69, Jan. 23, 2006, pp. 382-387.

Arthur, D.W. et al., "Improvements in Critical Dosimetric Endpoints Using the Contura Multilumen Ballon Breast Brachytherapy Catheter to Deliver Accelerated Partial Breast Irradiation: Preliminary Dosimetric Findings of a Phase IV Trial," Int. J. Radiation Oncology Biol. Phys., vol. 79, No. 1, 2011, pp. 26-33.

Atluri, S. et al., "Design of a Wideband Power-Efficient Inductive Wireless Link for Implantable Biomedical Devices Using Multiple Carriers," Proceedings of the International IEEE EMBS Conference on Neural Engineering Arlington, Virginia, Mar. 16-19, 2005, http://www.ece.ncsu.edu/erl/html2/papers/ghovanloo/2005/ghovanloo_2005_atluri.pdf.

Asgarian, F. et al., "Wireless Telemetry for Implantable Biomedical Microsystems," Integrated Circuits and Systems (ICAS) Lab., Department of Electrical and Computer Eng., K.N. Toosi University of Technology, www.intechopen.com/download/pdf/pdfs_id/12899.

Avitall, B. et al., "Physics and Engineering of Transcatheter Cardiac Tissue Ablation," Journal of the American College of Cardiology, vol. 22, No. 3, Sep. 1993, pp. 921-932.

Cavalcanti, A. et al., "Nanorobot for Treatment of Patients with Artery Occlusion," Proceedings of Virtual Concept, 2006, 10 pages.

Chaimanonart, N. et al., "Adaptive RF Power for Wireless Implantable Bio-Sensing Network to Monitor Untethered Laboratory Animal Real-Time Biological Signals," IEEE Sensors, Oct. 2008, pp. 1241-1244, Abstract.

Chandrakasan, AP et al., "Ultra-Power Electronics for Biomedical Applications", Annual Rev. Biomed. Eng., 2008, Abstract.

Cheung, K.C., "Implantable Microscale Neural Interfaces," Biomed Microdevices, Dec. 2007, pp. 923-938, Abstract.

Citro, R. et al., "Intracardiac Echocardiography to Guide Transseptal Catheterization for Radiofrequency Catheter Ablation of Left-Sided Accessory Pathways: two case reports," Cardiovascular Ultrasound, 2004, 7 pages.

Fotopoulou, K. et al., "Wireless Powering of Implanted Sensors Using RF Inductive Coupling," 5th IEEE Conference on Sensors, Oct. 2006, pp. 765-768, Abstract.

George, M.S. et al., "Vagus Nerve Stimulation: A New Tool for Brain Research and Therapy," Biol Psychiatry, 2000, pp. 287-295. http://www.ncbi.nlm.nih.gov/pubmed/10686263.

Gimsa, J. et al., "Choosing Electrodes for Deep Brain Stimulation Experiments—Electrochemical Considerations," J Neurosci. Methods, Mar. 30, 2005, Abstract.

Hijazi, N. et al., "Wireless Power and Data Transmission System for a Micro Implantable Intraocular Vision Aid," Biomed Tech (Berl), 2002; 47 Suppl 1 Pt1:174-5, Abstract.

Kim, S. et al., "Influence of System Integration and Packaging for a Wireless Neural Interface on its Wireless Powering Performance," 30th Annual International Conference of the IEEE Engineering in Medicine and Biology Society, Aug. 2008, pp. 3182-3185, Abstract.

Loeb, G.E. et al., "RF-Powered BIONs for Stimulation and Sensing," 26th Annual International Conference of the IEEE Engineering in Medicine and Biology Society, 2004, vol. 2, p. 4182, Abstract.

Lu, Hm et al., "MEMS-Based Inductively Coupled RFID Transponder for Implantable Wireless Sensor Applications," IEEE Transactions on Magnetics, vol. 43, No. 6, Jun. 2007, pp. 2412-2414.

Mokwa et al., "Intraocular Epiretinal Prosthesis to Restore Vision in Blind Humans," 30th Annual International Conference of the IEEE Engineering in Medicine and Biology Society, Aug. 2008, p. 5790, Abstract.

Mouine, J. et al., "A Completely Programmable and Very Flexible Implantable Pain Controller," Proc. of the 22nd Annual Intern Conference of the IEEE, vol. 2, 2000, pp. 1104-1107, Abstract.

Mounaim, F. et al., "Miniature Implantable System Dedicated to Bi-Channel Selective Neurostimulation," IEEE International Symposium on Circuits and Systems, 2007, pp. 2072-2075, Abstract.

Myers, F.B. et al., "A Wideband Wireless Neural Stimulation Platform for High-Density Microelectrode Arrays," 28th Annual International Conference of the IEEE Engineering in Medicine and Biology Society, Aug. 30, 2006, pp. 4404-4407, Abstract.

Papazoglou, C. et al., "Endoluminal Grafting: The Arizona Heart Institute Experience," International Congress VIII on Endovascular Interventions, Breaking Barriers, Scottsdale, Arizona, Feb. 12-16, 1995, pp. 89-129.

Peters, T.K. et al., "The Evolution Strategy-A Search Strategy Used in Individual Optimization of Electrica Therapeutic Carotid Sinus Nerve Stimulation," IEEE Transactions on Biomedical Engineering, vol. 36, Issue 7, pp. 668-675, Abstract http://ieeexplore.ieee.org/search/srchabstract.jsp?tp=&arnumber=32098&queryText%3D%28Implant+And+induction%29+AND+%28antenna+OR+coil%29+AND+%28t%29%26searchWit, Abstract, 1989.

Sawan, M., "Medical Microsystems for the Recovery of Vital Neural Functions," ncku.edu.tw polystim neurotechnologies Tianan, Taiwan, http://www.google.com/url?sa=t&source=web&cd=1&ved=0CBcQFjAA&url=http%3A%2F%2Ford.ncku.edu.tw%2Fezfiles%2F3%2F1003%2Fimg%2F467%2F20080911_ppt.pdei=elayTZeNO-Ls0gHW7IHCCw&usg=AFQjCNE8HVhol0Y63ztvd1sxK8-8aDdLAw&sig2=c7qWn1zQ2QUrwRMDvC53Gw.

Sawan, M., "Wireless Smart Implants Dedicated to Multichannel Monitoring and Microstimulation," IEEE/ACS International Conference on Pervasive Services, Jul. 2004, pp. 21-26, Abstract.

Schwiebert, L. et al., "Research Challenges in Wireless Networks of Biomedical Sensors," Disclosing for maximizing signal distance/minimizing power with multiple implant arrays in section 5.1, pp. 159-161, 2001.

Shabou, S. et al., "The RF Circuit Design for Magnetic Power Transmission Dedicated to Cochlear Prosthesis," 12th IEEE International Conference on Electronics, Circuits and Systems, 2005, pp. 1-4, Abstract.

Shepherd, RD et al., "Electrical Stimulation of the Auditory Nerve: II. Effect of Stimulus Waveshape on Single Fibre Response Properties," Hear Res., vol. 130, Apr. 1999, pp. 171-188, Abstract.

Sit, Ji-Jon et al., "A Low-Power Blocking-Capacitor-Free Charge-Balanced Electrode-Stimulator Chip with Less Than 6 nA DC Error for 1-mA Full-Scale Stimulation," IEEE Transactions on Biomedical Circuits and Systems, vol. 1, No. 3, Sep. 2007, pp. 172-183.

Suaning, G.J. et al., "CMOS Neurostimulation ASIC with 100 Channels, Scaleable Output, and Bidirectional Radio-Frequency," Biomedical Engineering, IEEE Transactions on Biomedical Engineering, vol. 48, Issue 2, pp. 248-260, Abstact, 2001.

Van Wieringen A. et al., "Effects of waveform Shape on Human Sensitivity to Electrical Stimulation of the Inner Ear," Hear Res., Feb. 2005, Abstract.

Venkataraman, S. et al., "RF-Front End for Wireless Powered Neural Applications," 51st Midwest Symposium Circuits and Systems, Aug. 2008, pp. 682-685, Abstract.

Wise, K.D. et al., "Wireless implantable Microsystems: High-Density Electronic Interfaces to the Nervous System," Proceedings of the IEEE, vol. 92, Issue 1, Jan. 2004, pp. 76-97, Abstract.

Xing et al., "Research Progress of Subrentinal Implant Based on Electronic Stimulation," Engineering in Medicine and Biology Society, 2005, pp. 1289-1292, Abstract http://ieeexplore.iee.org/search/srchabstract.jsp?queryText=%28Implant%20And%20induction%29%20AND%20%28antenna%20OR%20coil%29%20AND%20%28transfer%20OR%20relay%29%20AND%20%28multiple%20OR%20plural%20OR%20array%29%20AND%20%28medic*%20OR%20surg*%20OR%2.

Yazdandoost, KY et al., "An Antenna for Medical Implant Communications System," European Microwave Conference, 2007, pp. 968-971, Abstract.

Yekeh, K. et al., "Wireless Communications for Body Implanted Medical Device," Asia-Pacific Microwave Conference, 2007, pp. 1-4, Abstract.

Yoon, "A dual spiral antenna for Ultra-wideband capsule endoscope system," Department of Electronics and Electronic Engineering, Yonsei University Seoul, http://sciencestage.com/d/5302029/a-dual-spiral-antenna-for-ultra-widegand-capsule-endoscope-system.html, Abstract, Mar. 2008.

Zhang, YI et al., "Episodic phrenic-Inhibitory Vagus Nerve Stimulation Paradoxically Induces Phrenic Long-Term Facilitation in Rats," J Physiol., Sep. 15, 2003, pp. 981-991. Linghttp://www.ncbi.nlm.nih.gov/pmc/articles/PMC2343284.

Office Action dated Sep. 26, 2011, 17 pages, U.S. Appl. No. 12/324,000, filed Nov. 26, 2008.

Foreign Communication From a Related Counterpart Application—International Search Report, PCT/US2010/058737 dated Aug. 31, 2011, 7 pages.

Foreign Communication From a Related Counterpart Application—Written Opinion PCT/US2010/058737 dated Aug. 31, 2011, 8 pages.

Foreign Communication from a Related Counterpart Application—Office Action dated Jun. 15, 2011, German Application No. 112008003183.5.

Clark, et al., "Enhanced Recognition Memory Following Vagus Nerve Stimulation in Human Subjects," Nature Neuroscience, vol. 2, No. 1, Jan. 1999, pp. 94-98.

Dimyan, M.A. et al, "Neuroplasticity in the Context of Motor Rehabilitation After Stroke," Nat. Rev. Neurol. Feb. 2011, Review. http://www.nature.com/nrneurol/journal/v7/n2/abs/nrneurol.2010.200.htm?http://www.ncbi.nlm.nih.gov/pubmed/21243015.

Laskovski, A. et al., "Wireless Power Technology for Biomedical Implants," University of Newcastle, Australia, www.intechopen.com/download/pdf/pdfs_id/8797, Oct. 2009.

Popovic, D.B. et al., "Electrical Stimulation as a Means for Achieving Recovery of Function in Stoke Patients," NeuroRehabilitation, vol. 1, 2009, pp. 45-58. Abstract http://www.ncbi.nlm.nih.gov/pubmed/19713618.

Sharma, N. et al., "Electrical Stimulation and Testosterone Differentially Enhance Expression of Regeneration-Associated Genes," Exp Neurol., vol. 1, May 2010, pp. 183-191, Abstract.

Sooksood, K., et al., "Recent Advances in Charge Balancing for Functional Electrical Stimulation", Conf. Proc. IEEE Eng. Med. Biol. Soc., Nov. 13, 2009, Abstract.

Sooksood, K., et al., "An Experimental Study on Passive Charge Balancing," Adv. Radio Sci., vol. 7, 2009, pp. 197-200.

Van Greevenbroek, B., "The Development of Neuro-Prosthetic Devices," Feb. 10, 2011, http://www.google.com/url?sa=t&source=web&cd=17&ved=0CH4QFjAQ&url=http%3A%2F%2Figitur-archive.library.uu.nl%2Fstudent-theses%2F2011-0210-200413%2520development%2520of%252Neuro-Prosthetic%2520Devices%2520(Pdf%2520af).pdf%ei=rUeuTeTMN6W60QGt1bWq.

Office Action dated Oct. 25, 2011, 15 pages, U.S. Appl. No. 12/485,040, filed Jun. 15, 2009.
Office Action dated Jan. 3, 2012, 9 pages, U.S. Appl. No. 12/485,860, filed Jun. 16, 2009.
Office Action dated Jun. 5, 2012, 38 pages, U.S. Appl. No. 12/485,860, filed Jun. 16, 2009.

Office Action dated Oct. 26, 2011, 11 pages, U.S. Appl. No. 12/485,857, filed Jun. 15, 2009.
Office Action dated Oct. 28, 2011, 17 pages, U.S. Appl. No. 12/558,734, filed Sep. 14, 2009.

* cited by examiner

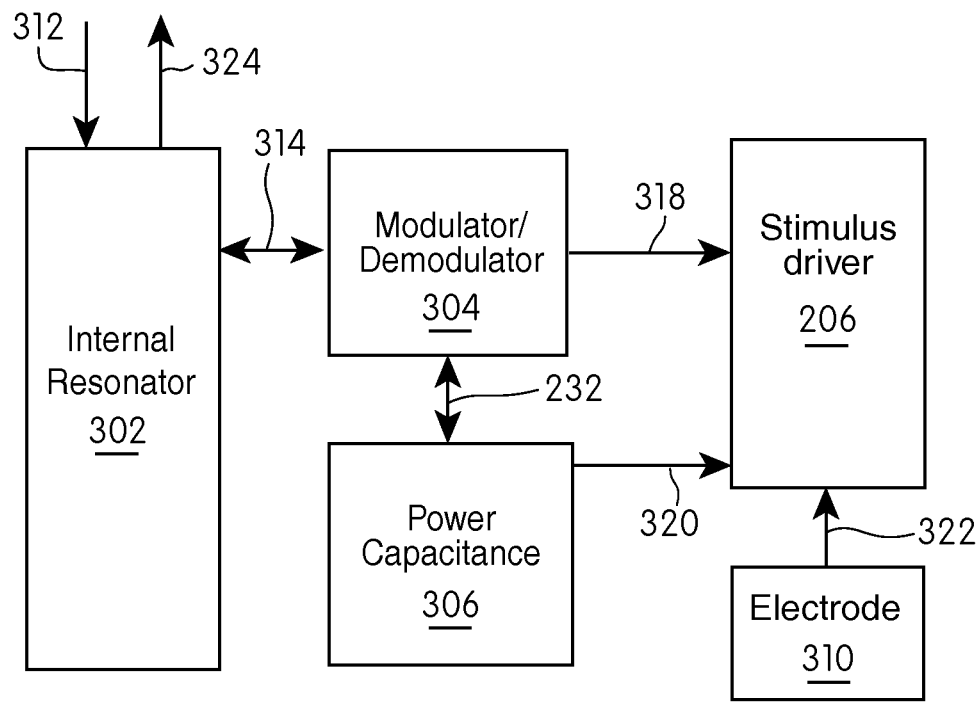
Fig. 3

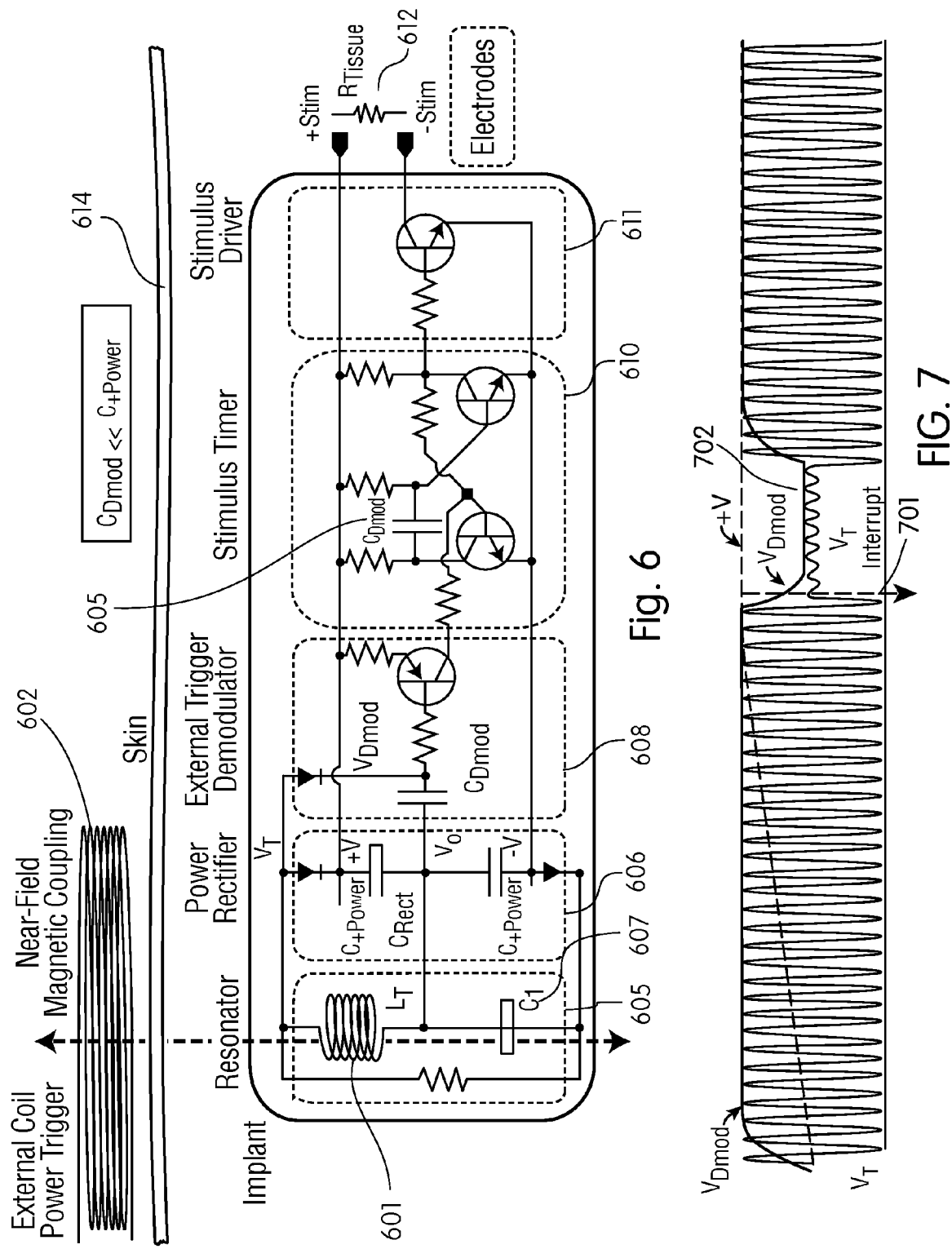

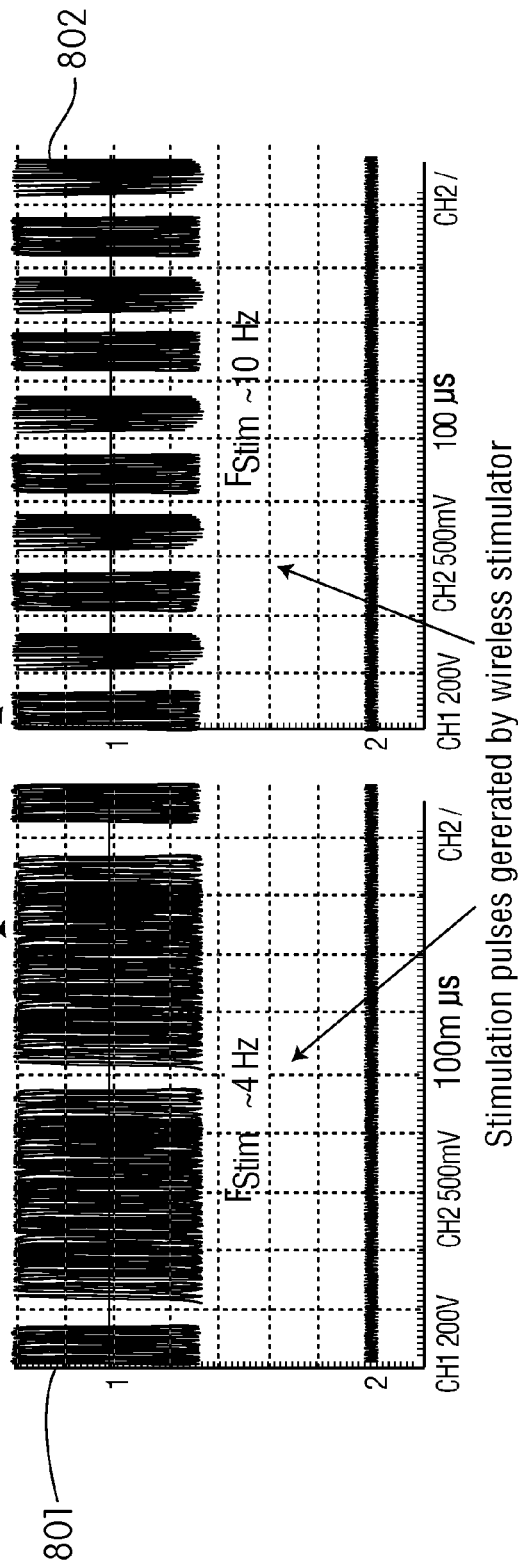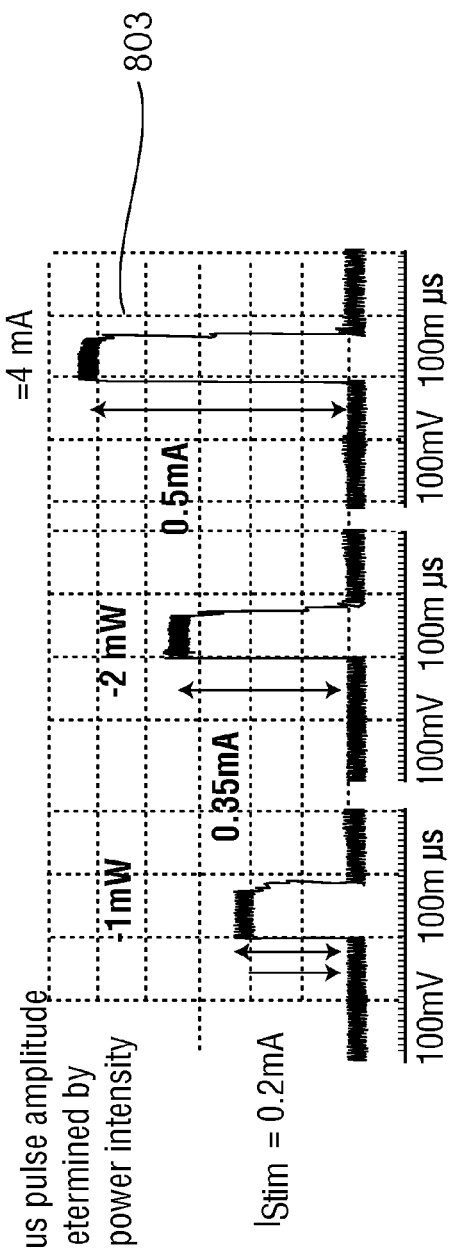
FIG. 8

IMPLANTABLE TRANSPONDER SYSTEMS AND METHODS

CROSS-REFERENCE TO OTHER APPLICATION

Priority is claimed from provisional application Ser. No. 60/990,278 filed Nov. 26, 2007, which is hereby incorporated by reference.

BACKGROUND

The present application relates to implantable peripheral nerve stimulation and sensor systems and more particularly to implantable microtransponders with identified reply.

BRIEF DESCRIPTION OF THE DRAWINGS

The disclosed inventions will be described with reference to the accompanying drawings, which show important sample embodiments of the invention and which are incorporated in the specification hereof by reference, wherein:

FIG. 3 is a block diagram depicting a data reply microtransponder in accordance with an embodiment;

FIG. 6 is a circuit diagram of a external trigger microtransponder in accordance with an embodiment;

FIG. 7 is a chart of the demodulation of an external interrupt trigger signal by differential filtering in accordance with an embodiment;

FIG. 8 includes graphs summarizing of microtransponder operation in accordance with an embodiment;

DETAILED DESCRIPTION OF SAMPLE EMBODIMENTS

Figure 1:
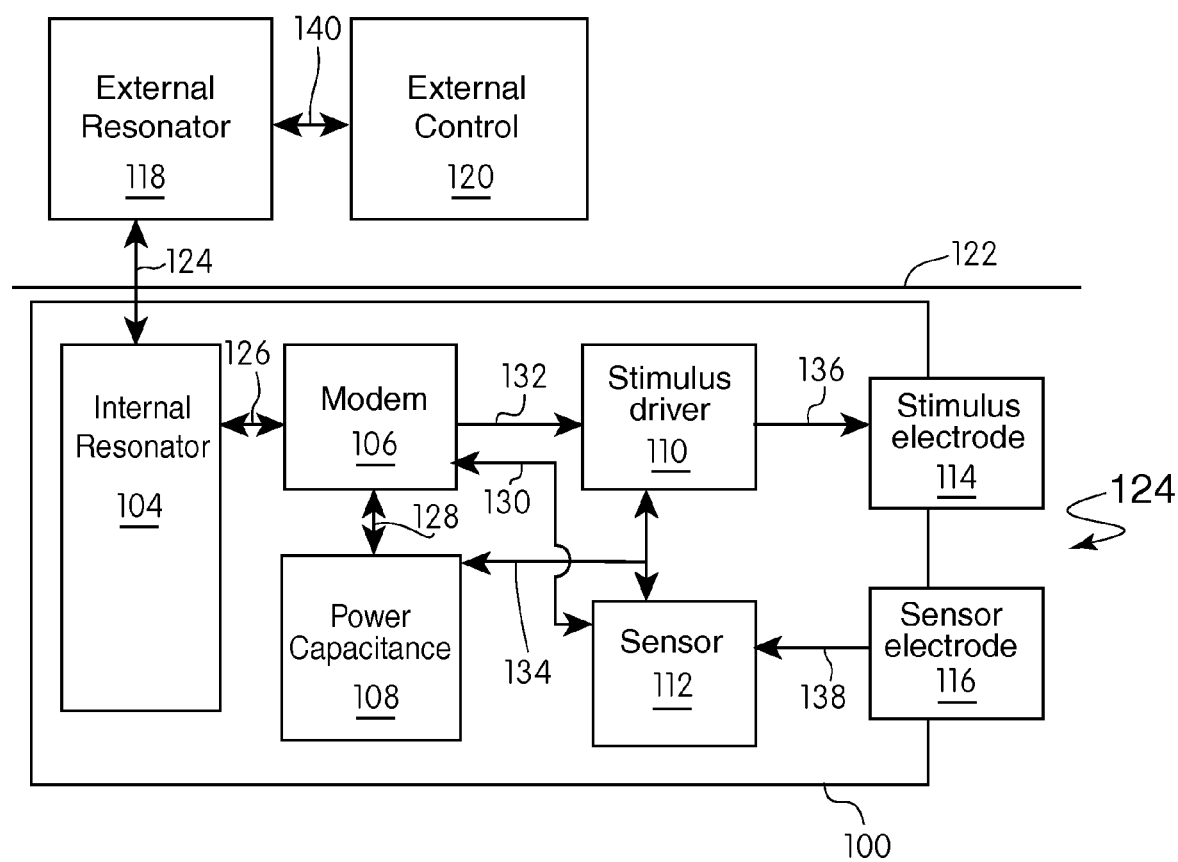
FIG. 1 is a block diagram depicting a reply microtransponder in accordance with an embodiment.

Note that the points discussed below may reflect the hindsight gained from the disclosed inventions, and are not necessarily admitted to be prior art.

A variety of medical conditions involve disorders of the neurological system within the human body. Such conditions may include paralysis due to spinal cord injury, cerebral palsy, polio, sensory loss, sleep apnea, acute pain and so forth. One characterizing feature of these disorders may be, for example, the inability of the brain to neurologically communicate with neurological systems dispersed throughout the body. This may be due to physical disconnections within the neurological system of the body, and/or to chemical imbalances that can alter the ability of the neurological system to receive and transmit electrical signals, such as those propagating between neurons.

Advances in the medical field have produced techniques aimed at restoring or rehabilitating neurological deficiencies leading to some of the above-mentioned conditions. However, such techniques are typically aimed at treating the central nervous system and therefore are quite invasive. These techniques include, for example, implanting devices, such as electrodes, into the brain and physically connecting those devices via wires to external system adapted to send and receive signals to and from the implanted devices. While beneficial, the incorporation of foreign matter into the human body usually presents various physiological complications, including surgical wounds and infection, rendering these techniques very challenging to implement.

The present application discloses new approaches to methods and systems for providing electrical stimulation to tissue includes implanting one or more battery-free microtransponders having spiral antennas into tissue. Energy is provided wirelessly to the plurality of microtransponders. Tissue is stimulated using the energy.

The disclosed innovations, in various embodiments, provide one or more of at least the following advantages. However, not all of these advantages result from every one of the innovations disclosed, and this list of advantages does not limit the various claimed inventions.

External power source and control
Minimally invasive stimulation units

The unprecedented miniaturization minimally invasive biomedical implants made possible with this wireless microtransponder technology would enable novel forms of distributed stimulation or high resolution sensing using micro-implants so small that implantation densities of 100 per square inch of skin are feasible. The microtransponders may operate without implanted batteries. Microtransponders communicate information and may be powered without wire connections. Additionally, microtransponders may be powered without wire connections that pass through the patient's skin or organ layers. The microtransponders may receive energy and information and may transmit energy and information using the flux of an electromagnetic fields between internal inductance coils within the microtransponders and external inductance coils placed above the surface of the overlying skin.

Power and modulated signals may be communicated wirelessly using the near-field magnetic coupling between two coils of conductive material. The coils of conductive material exhibit an inductance which in conjunction with a capacitance forms an LC resonator that may be tuned to resonate at specific frequencies. Two coils will communicate most efficiently when they are tuned to the same or related frequencies. Harmonic relationships between specified frequencies make it possible for different, harmonically related, frequencies to transfer power effectively, allowing coils of significantly different size to communicate with a suitable efficiency.

Recognizing this relationship between frequencies, references to tuning a pair of coils to the "same frequency" may include tuning the pair of coils to harmonically related frequencies. By energizing a first coil at a given frequency, an electromagnetic field is generated. By placing a second coil in the electromagnetic field, current is generated in the second coil. When the resonant frequencies of the coils are the same or of a harmonically related frequency, the generated current is maximized. Generated current may be typically stored in a capacitor and may be used to energize system elements.

With reference to FIG. 1, a block diagram depicts a microtransponder 100 in accordance with an embodiment. The microtransponder 100 may be implanted in tissue 124 beneath a layer of skin 122. The microtransponder 100 may be used to sense neural activity in the tissue 124 and communicate data to an external control 120 in response. The microtransponder 100 may be used to provide electrical stimulation to the tissue 124 in response to a signal from an external control 120. The electrodes 114 and 116 may be designed to enhance the electrical interface between the electrodes 114 and 116 and neurons of peripheral nerves.

The microtransponder 100 may wirelessly interact with other systems. The microtransponder 100 may interact via direct electrical connection with other systems. Typically, the microtransponder 100 interacts wirelessly with an external control system 120 including an external resonator 118. The microtransponder 100 may communicate via a direct electrical connection with other microtransponders (not shown) implanted within the body.

The microtransponder 100 enables delivery of electrical signals to peripheral nerves. These signals may be configured to stimulate peripheral nerves distributed throughout subcutaneous tissue 124. The microtransponder 100 enables the detection of electrical signals in peripheral nerves. The detected electrical signals may be indicative of neural spike signals.

Microtransponder 100 includes an internal resonator 104. The internal resonator 104 might be connected to a modulator-demodulator 106, to modulate information onto outgoing signals and/or retrieve information from incoming signals. The modulator-demodulator 106 may modulate or demodulate identification signals. The modulator-demodulator 106 may demodulate trigger signals. The modulator-demodulator 106 may receive signals from an impulse sensor 112. The modulator-demodulator 106 may provide trigger signals or other data to a stimulus driver 110. The impulse sensor 112 may be connected to a sensor electrode 116. The impulse sensor 112 may generate a signal when a current is detected at the sensor electrode 116. The stimulus driver 110 may be connected to stimulus electrodes 114. The stimulus driver 110 typically generates a stimulation voltage between the stimulus electrodes 114 when a trigger signal is received.

The internal resonator 104 provides energy to a power storage capacitance 108, which stores power received by the internal resonator 104. The power capacitance 108 may provide power 134 to the other components, including the stimulus driver 110, the impulse sensor 112 and the modem 106.

In operation, an external control 120, typically a computer or other programmed signal source, may provide commands 140 regarding sensing or stimulation for the microtransponder 100. The commands 140 are provided to an external resonator 118 and may initiate stimulation cycles, poll the devices, or otherwise interact with the microtransponder 100. The external resonator 118 is tuned to resonate at the same frequency, or a related frequency, as the internal resonator 104. Signal 126 are generated by the external resonator 118, resonated at the tuned frequency. The signal 126 may be a power signal without any modulated data. The signal 126 may be a power signal including modulated data, where the modulated data typically reflects commands 140 provided by the external control 120 such as identification information or addresses. It should be recognized that a power signal without modulated data may communicate timing data, such as a trigger signal, in the presentation or timing of the power signal.

The internal resonator 104 receives signals 126 from the external resonator 118. The internal resonator 104 provides a received signal 126 to the modulator-demodulator (modem) 106. The modem 106 may demodulate instructions 132 from the received signal. Demodulated instructions 132 may be provided to the stimulus driver 110. The modem 106 may pass the power signal 128 to the power capacitance 108. The power capacitance 108 may store the power signal 128. The power capacitance 108 may provide power to the stimulus driver 110. The power capacitance 108 may provide power to the impulse sensor 112. The stimulus driver 110 may provide a stimulus signal 136 to the stimulus electrode 114. The stimulus driver 110 may provide a stimulus signal 136 to the stimulus electrode 114 in response to an instruction 132. The stimulus driver 110 may provide a stimulus signal 136 to the stimulus electrode 114 in response to a power signal 134.

The modem 106 may provide an instruction 130 to impulse sensor 112. When an impulse is sensed in the tissue 124, the sensor electrode sends an impulse signal 138 to impulse sensor 112. The impulse sensor 112 sends a sensed impulse signal 130 to the modem 106. In response to the sensed impulse signal 112, the modem 116 may modulate an identification signal 126 onto a power signal 128. The internal resonator 104 generates a communication signal 124 including a modulated identification signal 126. The external resonator 118 receives the communication signal 124. Data 140 is provided to the external control 120.

Figure 2:
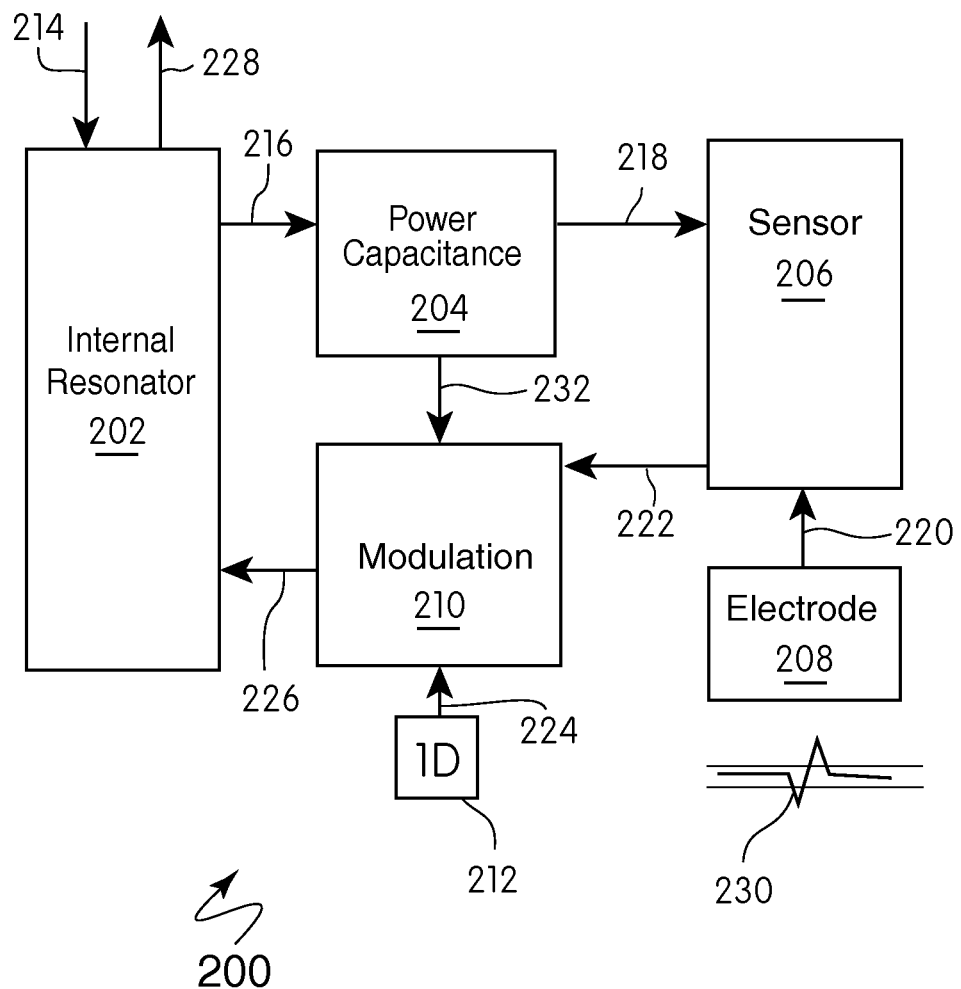
FIG. 2 is a block diagram depicting an identification reply microtransponder in accordance with an embodiment.

With reference to FIG. 2, a block diagram depicts a sensing microtransponder 200, in accordance with an embodiment. An internal resonator 202 receives an operation signal 214, where the operation signal 214 has been transmitted inductively by an external resonator (not shown). The operation signal 214 may include instructions, commands, address data or any other suitable data. The internal resonator 202 provides a power signal 216 to a power capacitance 204. The power capacitance 204 may subsequently provide power 218 to an impulse sensor 206, a modem 210, or any appropriate electrical component. The impulse sensor 206 is connected to a sensor electrode 208 placed proximate to peripheral nerve tissue 230. When an impulse passes through the peripheral nerve tissue 230, a charge is generated on the sensor electrode 208. The sensor electrode 208 provides a signal 220 to the impulse sensor 206. The impulse sensor 206 provides a signal to an identification modulator 210. The identification modulator 210 receives a power signal 232 from the power capacitance 204. The identification modulator 210 generates a modulated identification signal 226 using identification data 212. The internal resonator 202 generates a communication signal 228. An external resonator (not shown) receives the communication signal 228.

With reference to FIG. 3, a block diagram depicts a microtransponder 300 including data reply in accordance with an embodiment. An internal resonator 302 receives an operation signal 312 from an external resonator (not shown). The operation signal 312 may include data, such as identification information, addressing, commands, instruction or other suitable data. The internal resonator 302 provides a received signal to a modem 304. The internal resonator 302 provides a power signal 316 to a power capacitance 306. The modem 304 demodulates data 318 that has been modulated on the received signal 314. The data 318, typically a trigger signal, is provided to the stimulus driver 308. The stimulus driver 308 receives a power signal from a power capacitance 306. The stimulus driver 308 provides stimulation energy 322 to a stimulation electrode 310 in response to receiving the trigger signal 318. The modem 304 receives power 316 from the power capacitance 306. Modem 304 generates a data reply signal 314 in response to data 318. The internal resonator 302 generates a communication signal 324. An external resonator (not shown) receives the communication signal 324.

Figure 4:
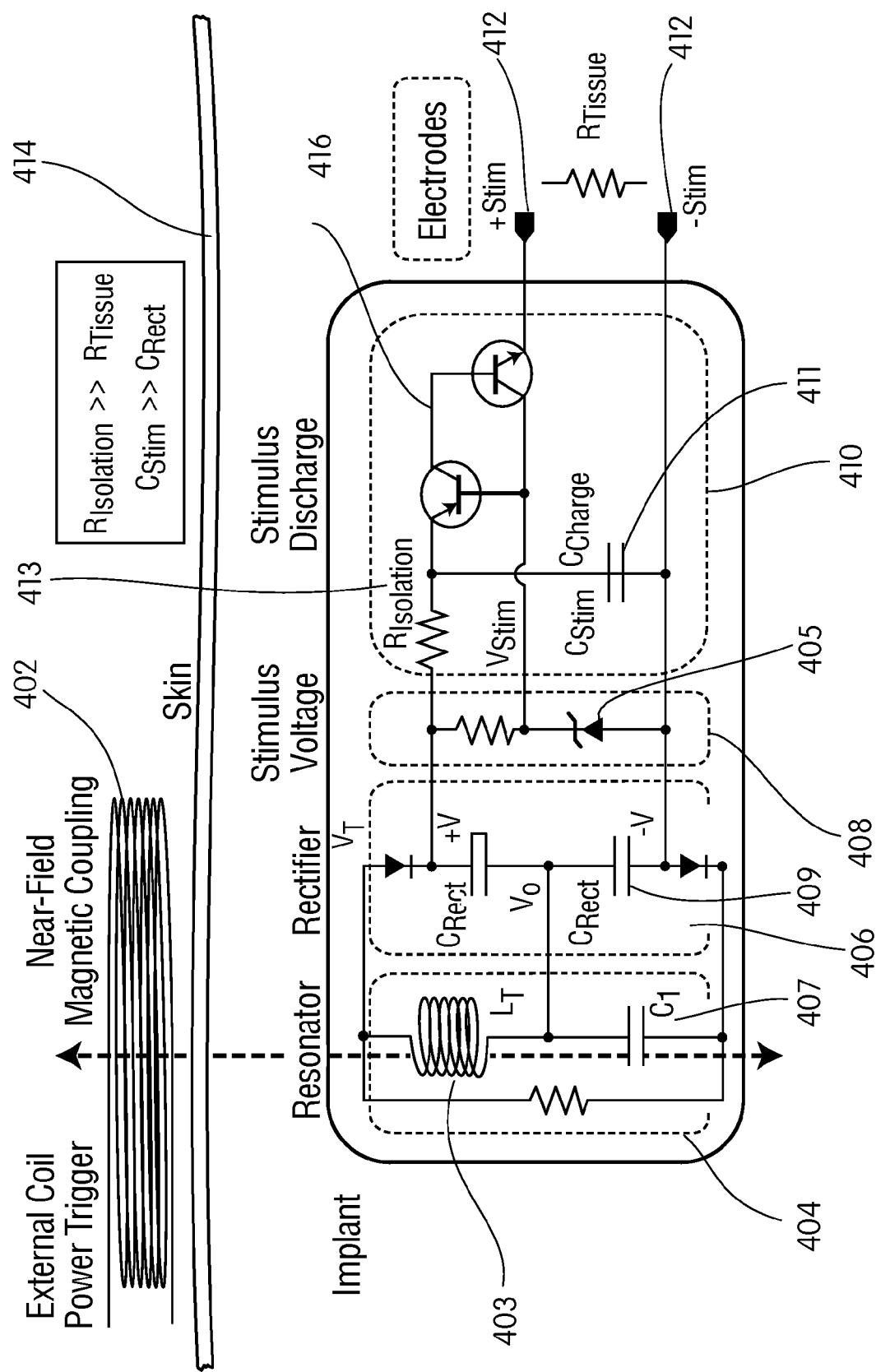
FIG. 4 is a circuit diagram depicting an asynchronous stimulation microtransponder in accordance with an embodiment.

With reference to FIG. 4, a circuit diagram depicts a wireless microtransponder having independent auto-triggering operation, in accordance with one embodiment. As shown by the circuit diagram, the auto-triggering microtransponder includes a resonator element 404, a rectifier element 406, a stimulus voltage element 408, a stimulus discharger element 410, and one or more electrodes 412. The resonator element 404 includes a coil (LT) component 403 that is coupled to a capacitor (CT) component 407. The resonator element 404 is configured to oscillate at a precise frequency that depends upon the values of the coil component 403 and capacitor component 407.

The resonator element 404 is coupled to the rectifier element 406 which is in turn coupled to the stimulus voltage element 408 and the stimulus discharger element 410. The rectifier element 406 and the stimulus voltage element 408 are both coupled in parallel to capacitors 409. In addition, the stimulus discharger element 410 is coupled to electrodes 412, thereby electrically connecting the stimulus discharger element 410 to neural conduction tissue, such as axons. It should be appreciated that in certain embodiments, a voltage booster component may be inserted immediately after, to the rectifier element 406 to boost the supply voltage available for stimulation and operation of the integrated electronics beyond the limits generated by the miniaturized LC resonant tank circuit. This voltage booster can enable electro stimulation and other microtransponder operations using the smallest possible LC components which may generate relatively small voltages (<0.5V). Examples of high efficiency voltage boosters include charge pumps and switching boosters using low-threshold Schottky diodes. However, it should be understood that any appropriate conventional high efficiency voltage booster may be utilized in this capacity.

In this circuit configuration, the auto-triggering microtransponder 400 can employ a bistable silicon switch 416 to oscillate between the charging phase that builds up a charge (Vcharge) on the stimulus capacitor 411 and the discharge phase that can be triggered when the charge (Vcharge) reaches the desired stimulation voltage (Vstim). The discharge phase begins with closing the switch 418 and discharging the capacitor through the stimulus electrodes 412. A single resistor 413 is used to regulate the stimulus frequency by limiting the charging rate of the stimulus capacitor 411. The breakdown voltage of a zener diode 405 is configured to set the desired stimulus voltage (Vstim). When Vcharge is equal to Vstim, the switch 416 closes, closing switch 418 and discharging the capacitor 411 into the electrodes 412. The electrodes 412 may be formed of gold, a platinum iridium alloy or any other suitable material. Switches 416 and 418 may typically be bipolar devices, field-effect transistors, or any other suitable device.

The stimulus peak amplitude and duration are largely determined by the effective tissue resistance, independent of the applied power intensity. Effective tissue resistance may vary depending on the type of tissue being stimulated, for example, skin, muscle, fat, etc. However, increasing the power may increase the stimulation frequency by reducing the time required to charge the stimulation capacitor 411 to the stimulus voltage Vstim.

The auto-triggering microtransponder 400 operates without timing signals from the power source 402 and auto-triggers repetitive stimulation independently. As a result, the stimulation generated by a plurality of such auto-triggering microtransponders 400 would be asynchronous in phase and somewhat variable in frequency from one stimulator to another depending upon the effective transponder voltage induced by each transponder. Such asynchronous stimulation may evoke the sort of disordered pins and needles or tingling sensations of parasthesias that are associated with stimulation methods that most effectively block pain signals.

Figure 5:
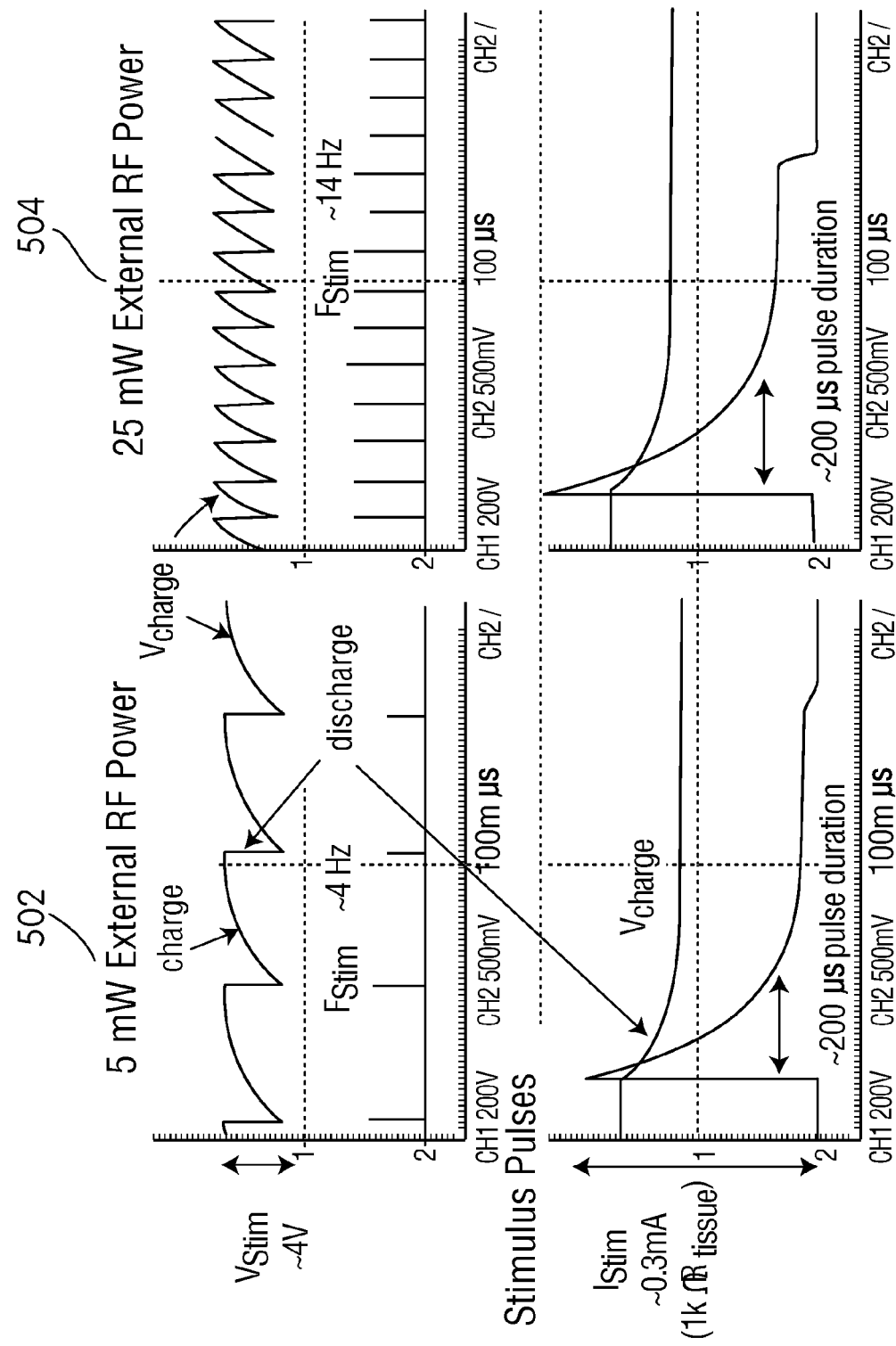
FIG. 5 includes graphs summarizing the variance of stimulus frequency, current amplitudes and stimulus pulse duration in accordance with an embodiment.

FIG. 5 presents several graphs that illustrate variations of wireless microtransponder stimulus frequencies stimulus current peak amplitudes and stimulus pulse durations vary under different device settings and external RF power input conditions, in accordance with an embodiment.

In the first graph 502, the external RF power input is set at 5 milliwatts resulting in a stimulus frequency of 4 Hertz. As discussed previously, the stimulus frequency is a function of transmitted power as the received power directly affects the time it takes to charge a stimulus capacitor to the stimulus voltage (Vstim). This direct relationship between RF power and stimulus frequency is clearly shown in graph 502, where the external RF power is ramped up to 25 milliwatts, which results in a significant increase in stimulus frequency to 14 Hz. It should be understood, however, that these are just examples of the affect of RF power input settings on stimulus frequency. In practice, the effects of the RF power input setting on stimulus frequency may be magnified or diminished depending on the particular application, for example, depth of implantation, proximity to interfering body structures such as bones, organs, etc. and device settings.

While RF intensity controls stimulus frequency, the stimulus voltage (Vstim) is typically controlled by the transponder zener diode element. The effect of stimulus voltage upon the stimulus current peak amplitude and pulse duration is further determined by the resistive properties of the tissue surrounding the microtransponder.

FIG. 6 is an illustration of a circuit diagram for a wireless microtransponder 600 with an external trigger signal demodulator element 608 to synchronize the stimuli delivered with a plurality of other wireless microtransponders, in accordance with an embodiment. As depicted, herein, the wireless transponder design of FIG. 5 is modified to include an external trigger signal demodulator element 608 so that the stimulus discharge can be synchronized by a trigger signal from an external RF power field.

The modified circuit includes a resonator element 604, a rectifier element 606, an external trigger demodulator element 608, a stimulus timer element 610, a stimulus driver element 611, and one or more electrodes 612. The resonator element 604 includes a coil component (LT) 601 that is coupled to a capacitor component (CT) 607. The resonator element 604 is configured to oscillate at a determined frequency depending on the value of the LC components LT 601 and CT 607.

The resonator element 604 is coupled to a rectifier element 606, which is in turn coupled to the external trigger demodulator element 608, the stimulus timer element 610 and the stimulus driver element 611. The rectifier element 607 and the stimulus timer element 608 are both coupled in parallel to power capacitors (Cpower) 609. In addition, the stimulus driver element 611 is coupled to electrodes 612, typically formed of gold or a platinum iridium alloy, thereby electrically connecting the stimulus driver element 611 to neural conduction tissue, such as axons.

It should be appreciated that, in certain embodiments, a standard voltage booster component (not shown) can be inserted immediately after the rectifier element 606 to boost the supply voltage available for stimulation and operation of integrated electronics beyond the limits generated by the miniaturized LC resonant tank circuit. A voltage booster may enable electro-stimulation and other microtransponder operations using the smallest possible LC components, which may generate relatively small voltages, for example, less than 0.5 Volts. Examples of typical high efficiency voltage boosters include charge pumps and switching boosters using low-threshold Schottky diodes. However, it should be understood that any suitable type of conventional high efficiency voltage booster may be utilized in this capacity.

As show in FIG. 7, the external synchronization-trigger circuit configuration of FIG. 6 may employ a differential filtering method to separate the trigger signal, consisting of a sudden power interruption 701, from the slower drop in transponder power voltage 702 during the interruption. In particular, the circuit configuration of FIG. 6 may utilize a separate capacitor (CDur) 605 in the stimulus timer element 610, to set the stimulus duration using a mono-stable multi-vibrator. Stimulus intensity can be controlled externally by the intensity of the applied RF power field generated by the external FR power coil 602. As the RF power field is modulated, the timing and frequency of stimuli from each of the microtransponders under the RF power coil 602 are synchronized externally.

Using the external synchronization-trigger circuit configuration of FIG. 6, the degree of spatio-temporal control of complex stimulus patterns is essentially unlimited. In certain embodiments, the circuit configuration of the external synchronization-trigger circuit can be further modified so that it is configured to demodulate the unique identity code of each microtransponder. This essentially permits the independent control of each microtransponder via RF signals. This added capability can provide a method to mediate the spatio-temporal dynamics necessary to restore natural sensations with artificial limbs or enable new sensory modalities, for example feeling infrared images, etc.

FIG. 8 presents several graphs that summarize the results from tests of a wireless microtransponder (with an external interrupt trigger de-modulator element) under different device settings and external RF power input conditions, in accordance with one embodiment. In the first graph 801, the external RF power coil modulates the RF power field to communicate a first trigger signal setting, which results in a stimulus frequency of 2 Hz. As discussed previously, the stimulus frequency is controlled by a trigger signal created when the RF power coil modulates the RF power field. The stimulus frequency is therefore directly related to the RF power field modulation frequency as shown in the second graph 802, where the stimulus frequency equals 10 Hz.

Whereas the stimulus frequency is controlled by external RF power field modulation settings, the stimulus current peak amplitude is controlled by the RF power intensity setting, as shown in the third graph 803. That is, the stimulus current peak amplitude is directly related to the RF power intensity setting. For example, an RF power intensity setting of 1 mW produces a stimulus current peak amplitude of 0.2 mA, a RF power intensity setting of 2 mW produces a stimulus current peak amplitude of 0.35 mA, and a RF power intensity setting of 4 mW produces a stimulus current peak amplitude of 0.5 mA. It should be understood, however, that these are just examples of how RF power intensity setting affects stimulus current peak amplitude. In practice, the effects of the RF power intensity setting on stimulus current peak amplitude may be magnified or diminished depending on the particular application (e.g., depth of implantation, proximity to interfering body structures such as bone, etc.) and device settings.

Whereas the stimulus frequency is controlled by an external RF power field modulation settings, the stimulus current peak amplitude is controlled by the RF power intensity setting as shown in the third graph 803. That is, the stimulus current peak amplitude is directly related to the RF power intensity setting. For examples, an RF power intensity setting of 1 milliwatts produces a stimulus current peak amplitude of 0.2 milliamps, an RF power intensity setting of 2 milliwatts produces a stimulus current peak amplitude of 0.35 milliamps, and an RF power intensity setting of 4 milliwatts produces a stimulus current peak amplitude of 0.5 milliamps. It should be understood, however, that these are just examples of how RF power intensity settings affect stimulus current peak amplitude. In practice, the effects of the RF power intensity setting on stimulus current peak amplitude may be magnified or diminished depending on the particular application, for example, the depth of implantation, proximity to interfering body structures such as bones, etc., and device settings.

Figure 9:
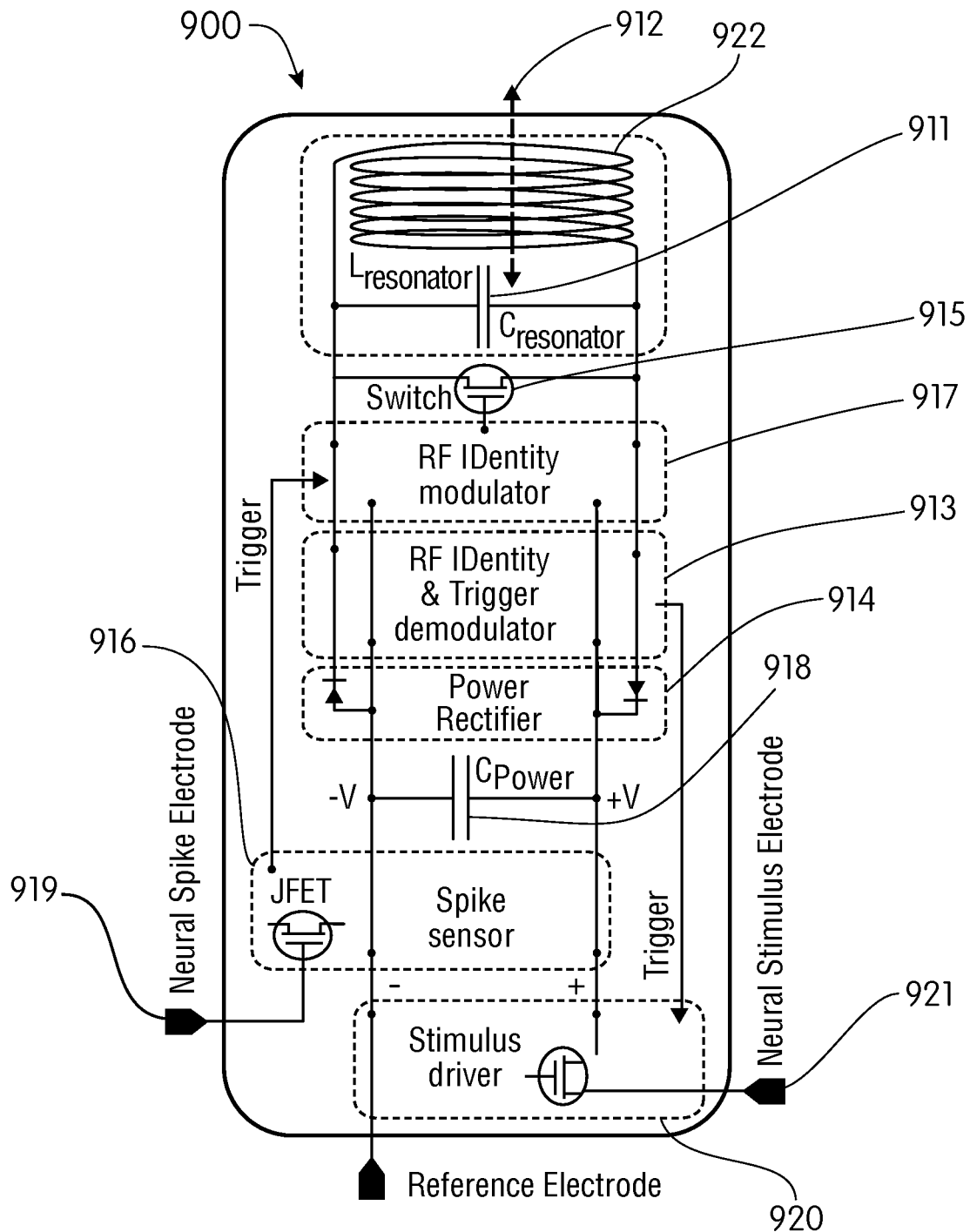
FIG. 9 is a circuit diagram of a microtransponder in accordance with an embodiment.

With reference to FIG. 9, a block diagram depicts a microtransponder 900 in accordance with an embodiment. The microtransponder 900 includes electrical components adapted to electrically interface with neurons of peripheral nerves. The microtransponder 900 includes electrical components that enable the microtransponder 900 to wirelessly interact with systems external to the microtransponder 900. These systems may include other transponders implanted within the body. These systems may include external coils. These systems may include a receiver.

The wireless capability of the microtransponder 900 enables the delivery of electrical signals to the peripheral nerve tissue. The wireless capability of the microtransponder 900 enables communication in response to sensed signals in the peripheral nerve tissue. These may include signals indicative of neural spike signals. These may include signals configured to stimulate peripheral nerves distributed throughout the subcutaneous tissue.

The microtransponder 900 includes coils 922 coiled about a central axis 912. The coil 922 is coupled in parallel to a capacitor 911 and to an RF identity modulator 917 via switch 915. The RF identity modulator 917 is coupled to an RF identity and trigger demodulator 913, which in turn is coupled to a rectifier 914. The rectifier 914 and the spike sensor 916 are both coupled in parallel to a capacitor 918. In addition, the spike sensor 916 is coupled to a neural spike electrode 919, thereby electrically connecting the spike sensor 916 to neural transmission tissue, such as neurons. Similarly, the neural stimulus electrode 921 also connects the stimulus driver 920 to neural conduction tissue such as axons.

The spike sensor 916 is made up of one or more junction field effect transistors (JFET). As will be appreciated by those skilled in the art, the JFET may include MOSFETS or any other suitable device. The sensors, drivers and other electronic components described in the present application may be fabricated using standard small scale or very large scale integration (VLSI) methods.

Further, the spike sensor 916 is coupled to the RF identity modulator 917, which is adapted to modulate an incoming/carrier RF signal in response to neural spike signal detected by the spike sensor 916. In an embodiment, the neural electrodes such as the neural spike electrode 919 and the neural stimulus electrode 921 to which the spike sensor 916 and the stimulus driver 920 are connected, respectively, may be bundled and configured to interface with neural conduction (axon) portion of a peripheral nerve.

The microtransponder may operate as an autonomous wireless unit, capable of detecting spike signals generated by peripheral nerves and relaying such signals to external receivers for further processing. It should be understood that the microtransponder performs such operations while being powered by external RF electromagnetic signals. The above-mentioned capabilities are facilitated by the fact that magnetic fields are not readily attenuated by human tissue. This enables the RF electromagnetic signals to sufficiently penetrate the human body so that signals can be received and/or transmitted by the microtransponder. In other words, the micro-coils 922 are adapted to magnetically interact with the RF field whose magnetic flux fluctuates within the space encompassed by the coils 922. By virtue of being inductors, the coils 922 convert the fluctuations of the magnetic flux of the external RF field into alternating electrical currents, flowing within the coils 922 and the microtransponder 900. The alternating current is routed, for example, via the coils 922 into the rectifier 914, which is adapted to convert the alternating current into direct current. The direct current may then be used to charge the capacitor 918 thereby creating a potential difference across the JFET of the sensor trigger 916.

In an exemplary embodiment, a gate of the spike sensor JFET 916 may be coupled via the neural spike electrode 919 to the neural transmission tissue, such as neurons. The gate of the spike sensor JFET 16 may be chosen to have a threshold voltage that is within a voltage range of those signals produced by the neural axons. In this manner, during spike phases of the neural axons, the gate of the spike sensor JFET 916 becomes open, thereby closing the circuit 910.

Once the circuit 910 closes, the external RF electromagnetic field generates an LC response in the coupled inductor 922 and capacitor 918, which then resonate with the external RF electromagnetic field with its resonance matching the modulating frequency of the RF electromagnetic field.

The LC characteristic of the circuit 910, as well as the threshold voltage of the gate of spike sensor JFET 916 can be chosen to determine a unique modulation within the coupled inductor 922 and capacitor 918 thereby providing a desired ID signal for the microtransponder. Accordingly, the spike sensor JFET 916 provides the RF identity modulator 917 with a trigger signal for generating desired RF signals. The ID signal may indicate the nature of the neural activity in the vicinity of the microtransponder as well as the location of the neural activity within the body.

It should be appreciated that the RF capabilities render the microtransponder 900 a passive device which reacts to incoming carrier RF signals. That is, the microtransponder 900 does not actively emit any signals but rather reflects and/or scatters the electromagnetic signals of the carrier RF wave to provide signals having specific modulation. In so doing, the microtransponder 900 draws power from the carrier RF wave for powering the electrical components therein.

While the above mentioned components illustrated in FIG. 9 may be used to receive signals form the microtransponder in response to spike signals generated by peripheral nerves, other components of the microtransponder 900 may include components for stimulating the peripheral nerves using the external RF signals. For example, the RF signals received by the coils 922 may be converted to electrical signals, via the RF identity and trigger demodulator 913, so as for providing sufficient current and voltage for stimulating the peripheral nerves. Hence, the RF identity and trigger demodulator 913 derives power from an RF carrier signal for powering the stimulus driver 920, which delivers electrical signals suitable for stimulating neural conduction tissue, such as axons. This may be used to treat nerves that are damaged or that are otherwise physiologically deficient.

It should be understood that, in certain embodiments, the minimum size for the microtransponders may be limited by the size of the micro-coil responsible for power induction, and secondarily by the size of the capacitors necessary for tuning power storage and timing. In fact, micro-coils less than 1 millimeter in diameter and just a few micrometers thick can provide sufficient wireless power to operate the complex micro-electronics that can be manufactured on integrated circuit chips that are typically much smaller than these coils. Combining the sophisticated functionality of micro-electronic chips with the wireless performance of these micro-coils creates the smallest possible, minimally invasive implants, in the form of tiny flecks as small as 0.1 mm thick and 1 mm wide. These size and power advantages make it possible to add relatively complex digital electronics to the smallest, least invasive micro-transponder implant.

FIG. 9 is a functional schematic of a complete microtransponder for sensing and/or stimulating neural activity, in accordance with one embodiment. The circuit is designed for dependent triggering operation (synchronous stimulation). The circuit 900 includes electrical components adapted to electrically interface with neurons of peripheral nerves. The circuit 900 further includes electrical components which enable the microtransponder to wirelessly interact with systems external to the microtransponder. Such systems may include other transponders implanted within the body or external coils and/or a receiver. The wireless capabilities of the circuit 900 enable the delivery of electrical signals to and/or from the peripheral nerves. These include electrical signals indicative of neural spike signals and/or signals configured to stimulate peripheral nerves distributed throughout the subcutaneous tissue.

Accordingly, the circuit 900 includes the micro-coil 922 coiled about a central axis 912. The micro-coil 922 is coupled in parallel to a capacitor 911 and to an RF identity modulator 917 via a switch 915. The RF identity modulator 917 is coupled to an RF identity and trigger demodulator 913, which in turn is coupled to a rectifier 914. The rectifier 914 is coupled to a spike sensor trigger 916 and to a stimulus driver 920. The rectifier 914 and the spike sensor 916 are both coupled in parallel to a capacitor 918. In addition, the spike sensor 916 is coupled to a neural spike electrode 919, thereby electrically connecting the spike sensor 916 to neural transmission tissue (neurons). Similarly, the neural stimulus electrode 921 also connects the stimulus driver 920 to neural conduction tissue (axons). The spike sensor 916 is made up of one or more junction field effect transistors (JFET). As will be appreciated by those of ordinary skilled in the art, the JFET may include metal oxide semiconductors field effect transistors (MOSFETS).

The sensors, drivers, and other electronic components described in the present application can be fabricated using standard small scale or very large scale integration (VLSI) methods. Further, the spike sensor 916 is coupled to the RF identity modulator 917, which is adapted to modulate an incoming/carrier RF signal in response to neural spike signals detected by the spike sensor 916. In one embodiment, the neural electrodes (i.e., neural spike electrode 919 and neural stimulus electrode 921) to which the spike sensor 916 and the stimulus driver 920 are connected, respectively, can be bundled and configured to interface with neural conduction (axon) portion of a peripheral nerve.

One configuration of the above components, as depicted by FIG. 9, enables the microtransponder to operate as an autonomous wireless unit, capable of detecting spike signals generated by peripheral nerves, and relaying such signals to external receivers for further processing. It should be understood that the microtransponder performs such operations while being powered by external RF electromagnetic signals. The above-mentioned capabilities are facilitated by the fact that magnetic fields are not readily attenuated by human tissue. This enables the RF electromagnetic signals to sufficiently penetrate the human body so that signals can be received and/or transmitted by the microtransponder. In other words, the micro-coil 922 is designed and configured to magnetically interact with the RF field whose magnetic flux fluctuates within the space encompassed by the micro-coil 922. By virtue of being inductors, the micro-coils 922 convert the fluctuations of the magnetic flux of the external RF field into alternating electrical currents, flowing within the micro-coil 922 and the circuit 910. The alternating current is routed, for example, into the rectifier 914, which converts the alternating current into direct current. The direct current may then be used to charge the capacitor 918, thereby creating a potential difference across the JFET of the spike sensor 916.

In an exemplary embodiment, a gate of the spike sensor 916 JFET may be coupled via the neural spike electrode 919 to the neural transmission tissue (neurons). The gate of the spike sensor 916 JFET may be chosen to have a threshold voltage that is within a voltage range of those signals produced by the neural axons. In this manner, during spike phases of the neural axons, the gate of the spike sensor 916 becomes open, thereby closing the circuit 910. Once the circuit 910 closes, the external RF electromagnetic field generates an LC response in the coupled inductor 922 and capacitor 918, which then resonate with the external RF electromagnetic field, with its resonance matching the modulating frequency of the RF electromagnetic field. The LC characteristic of the circuit 910, as well as the threshold voltage of the gate of spike sensor 916 JFET, can be chosen to determine a unique modulation within the coupled micro-coil (i.e. inductor) 922 and capacitor 918, thereby providing a identifying signal for the microtransponder. Accordingly, the spike sensor 16 JFET provides the RF identity modulator 917 with a unique trigger signal for generating desired RF signals. The identity signal may indicate the nature of the neural activity in the vicinity of the microtransponder, as well as the location of the neural activity within the body as derived from the specific identified microtransponder position.

It should be appreciated that the RF capabilities, as discussed above with respect to the circuit 910, can render the microtransponder a passive device which reacts to incoming carrier RF signals. That is, the circuit 910 does not actively emit any signals, but rather reflects and/or scatters the electromagnetic signals of the carrier RF wave to provide signals having specific modulation. In so doing, the circuit 910 draws power from a carrier radio frequency (RF) wave to power the electrical components forming the circuit 910.

While the above-mentioned components illustrated in FIG. 9 may be used to receive signals from the microtransponder in response to spike signals generated by peripheral nerves, other components of circuit 910 of the microtransponder may include components for stimulating the peripheral nerves using the external RF signals. For example, the RF signals received by the micro-coil 922 may be converted to electrical signals, via the RF identity and trigger demodulator 913, so as to provide sufficient current and voltage for stimulating the peripheral nerves. Hence, the RF identity and trigger demodulator 913 derives power from an RF carrier signal for powering the stimulus driver 920, which delivers electrical signals suitable for stimulating neural conduction tissue (axons). This may be used to treat nerves that are damaged or that are otherwise physiologically deficient. Because of the nature of the identifying signal, a microtransponder can be selectively activated to provide electrostimulation.

It should be understood that, in certain embodiments, the minimum size for the microtransponders may be limited by the size of the micro-coil responsible for power induction, and secondarily by the size of the capacitors necessary for tuning power storage and timing. Therefore, micro-coil designs that minimize the complex integrated circuits can be fabricated to an extremely small size (such as less than 1 micron) and ultra-low power technology. The size and power advantages make it possible to add relatively complex digital electronics to the smallest transponder.

Figure 10:
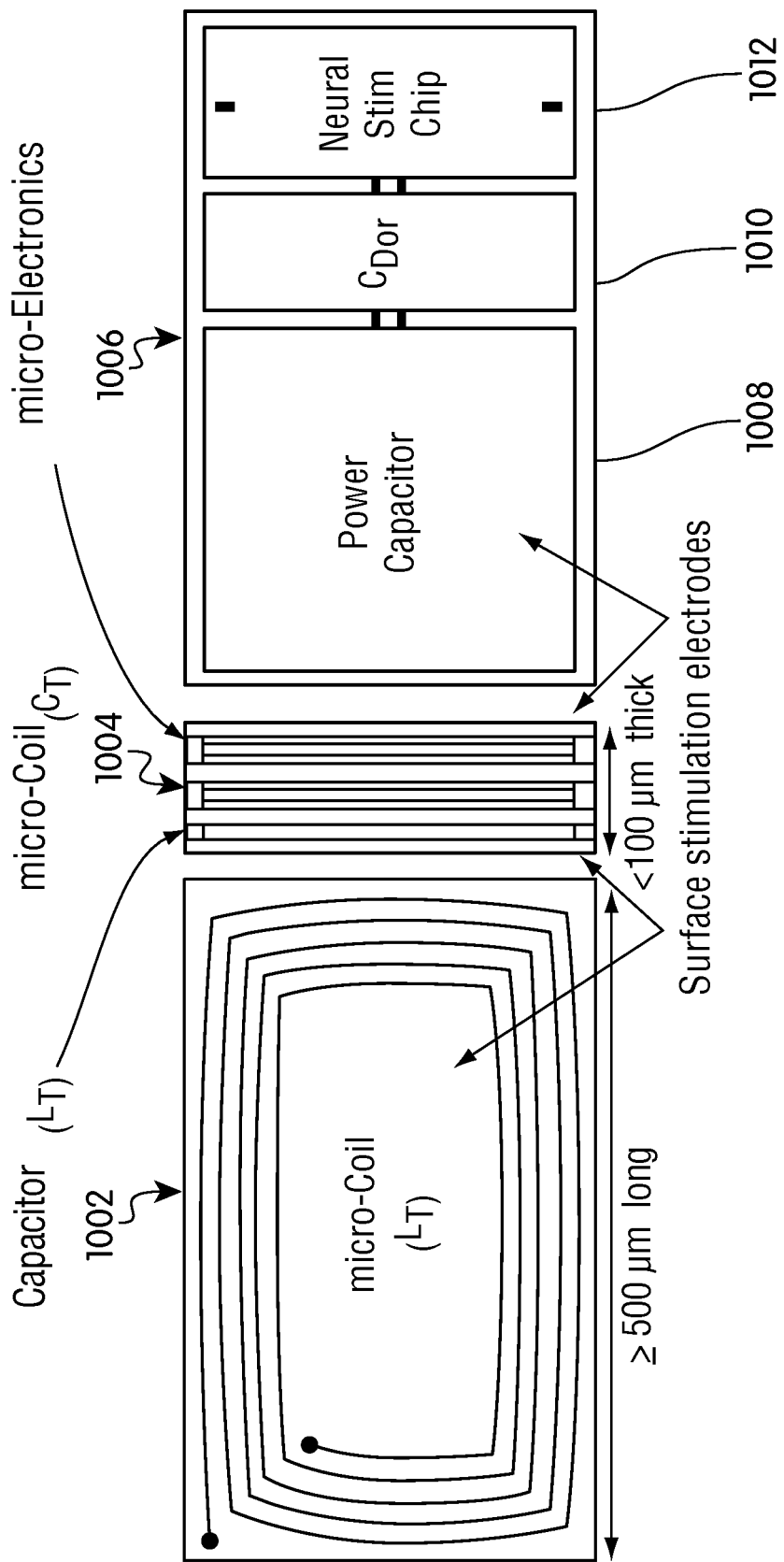
FIG. 10 is an illustration of a laminar spiral micro-foil in accordance with an embodiment.

FIG. 10 is an illustration of a laminar spiral micro-foil used in the construction of a microtransponder platform for stimulating neural activity, in accordance with one embodiment. The spiral antenna may be a flat spiral antenna, a two-layered spiral antenna, a split-spiral antenna or any other suitable configuration. As depicted, herein, the microtransponder includes a laminar spiral micro-coil (LT) 1002 coupled to a capacitor (CT) 1004 which in turn is coupled to a microelectronics chip 1006. The micro-electronics chip 1006 includes a power capacitor element 1008 coupled to a capacitor (CDUR) element 1010, which in turn is coupled to a neural stimulation chip element 1012.

In an exemplary embodiment of the microtransponder platform, the micro-coil is no more than 500 micrometers long by 500 micrometers wide and the combined thickness of the laminar spiral micro-coil (LT) 1002, capacitor (CT) 1004 and micro-electronics chip 1006 is no more than 100 micrometers.

Figure 11:
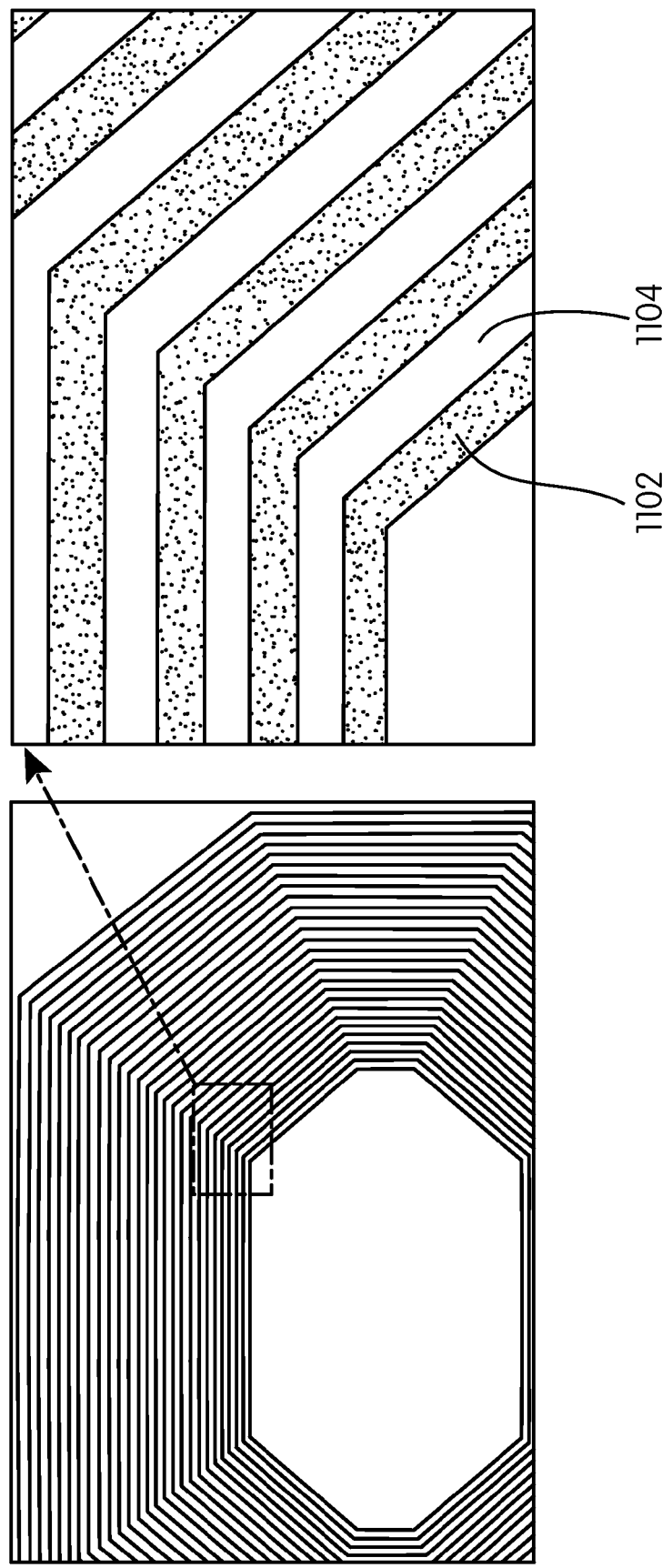
FIG. 11 is an illustration of a gold laminar spiral micro-foil in accordance with an embodiment.

FIG. 11 is an illustration of a gold laminar spiral micro-coil electroplated onto a substrate, in accordance with one embodiment. As depicted in the photo-micrographs, gold conductor lines are initially electroplated in a tight spiral pattern onto a non-reactive substrate (e.g., glass, silicon, etc.) In one embodiment, the gold laminar spiral micro-coil can include gold conductor lines 1102 that are about 10 micrometers wide and the spacing 1104 between the conductor lines set at about 10 micrometers. In another embodiment, the gold laminar spiral micro-coil can include gold conductor lines 1102 that are about 20 micrometers wide and the spacing 1104 between the conductor lines set at about 20 micrometers. It should be understood, however, that the widths of the gold conductor line 1102 and line spacing 1104 between them can be set to any value as long as the resulting micro-coil can produce the desired induced current for the desired application.

In certain embodiments, once the gold spiral micro-coil has been electroplated onto the substrate, a polymer-based layer is spun on top of the micro-coils to provide a layer of protection against corrosion and decay once implanted. Long term studies of animals with SU-8 implants have verified the biocompatibility of SU-8 plastic by demonstrating that these SU-8 implants remain functional without signs of tissue reaction or material degradation for the duration of the studies. Therefore, typically, the polymer-based layer is comprised of an SU-8 or equivalent type of plastic having a thickness of approximately 30 micrometers.

Figure 12:
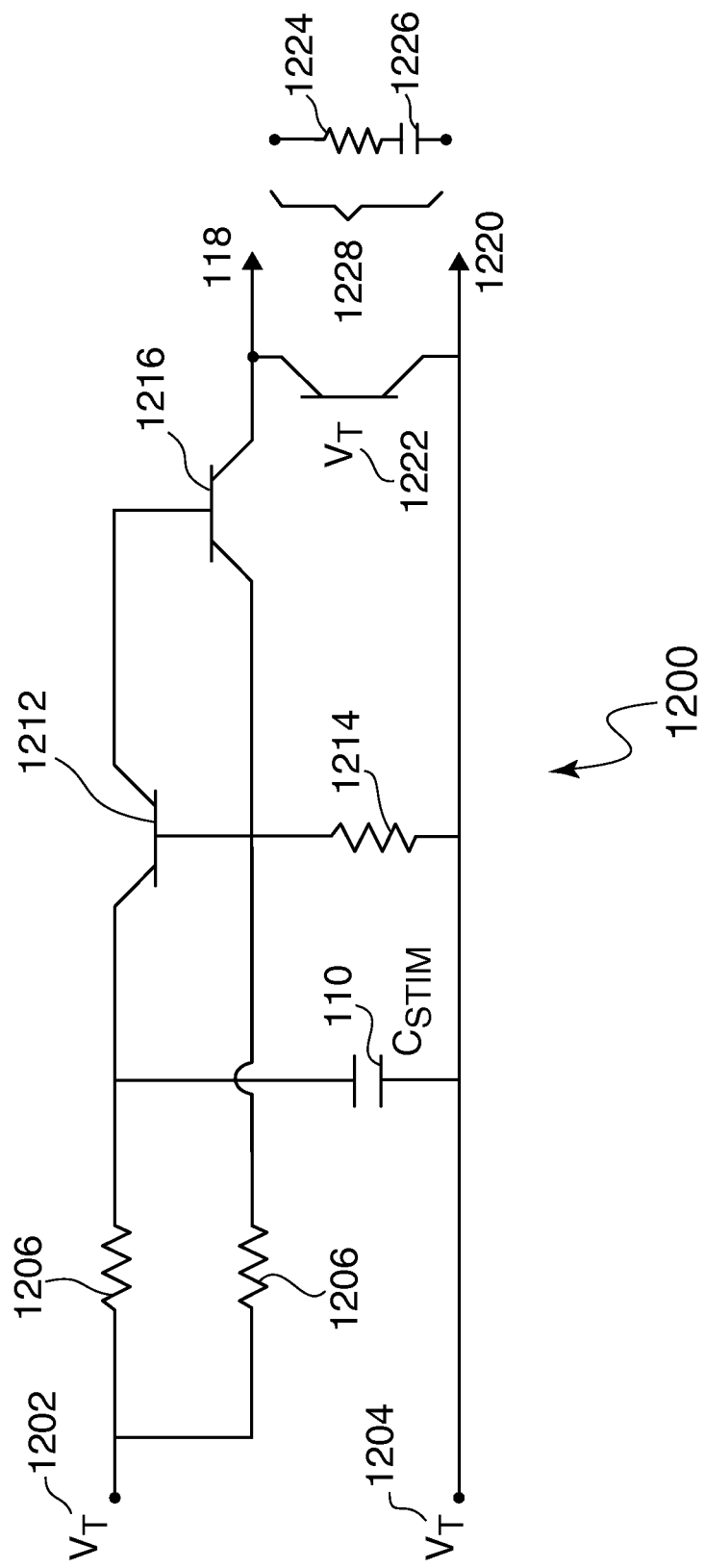
FIG. 12 is a circuit diagram depicting a depolarizing microtransponder driver circuit, in accordance with an embodiment.

With reference to FIG. 12, a schematic diagram depicts a depolarizing microtransponder driver circuit 1200 in accordance with an embodiment. An oscillating trigger voltage (VT and −VT) may be applied between the input nodes 1202 and 1204 of the driver circuit 1200. An auto-triggering microtransponder may employ a bi-stable switch 1212 to oscillate between the charging phase that builds up a charge on the stimulus capacitor CSTIM 1210 and the discharge phase that can be triggered when the charge reaches the desired voltage and closes the switch 1212 to discharge the capacitor 1210 through stimulus electrodes 1218 and 1220.

A resistor 1206 regulates the stimulus frequency by limiting the charging rate. The stimulus peak and amplitude are largely determined by the effective tissue resistance 1228, modeled with a resistance 1224 and a capacitance 1226. As such, the stimulus is generally independent of the applied RF power intensity. On the other hand, increasing the RF power may increase the stimulation frequency by reducing the time it takes to charge up to the stimulus voltage.

When a stimulation signal is applied to living tissue at frequencies higher than two hertz, the tissue typically becomes polarized, exhibiting an inherent capacitance 1226 by storing a persistent electrical charge. In order to reduce the polarization effect, a depolarization switch 1222 is connected between the electrodes 1218 and 1220. The gate terminal of the depolarization switch 1222 is connected to the oscillating trigger voltage VT, so that once each cycle, the depolarization switch shorts the electrodes 1218 and 1220 and reduces the charge stored in the inherent tissue capacitance 1226. The timing of the depolarization switch 122 permits the stimulation pulse to be substantially discharged before the depolarization switch 122 closes and shorts the electrodes 118 and 120. Similarly, the depolarization switch 122 is timed to open before a subsequent stimulation pulse arrives. The timing of the depolarization switch 122 may be generated relative to the timing of the stimulation pulse, The timing may be accomplished using digital delays, analog delays, clocks, logic devices or any other suitable timing mechanism.

A simple zener diode component may be included in a stimulator circuit as presented in FIG. 1. Asynchronous stimulations can be accomplished using the zener diode to accomplish voltage levels for auto-triggering.

Figure 13:
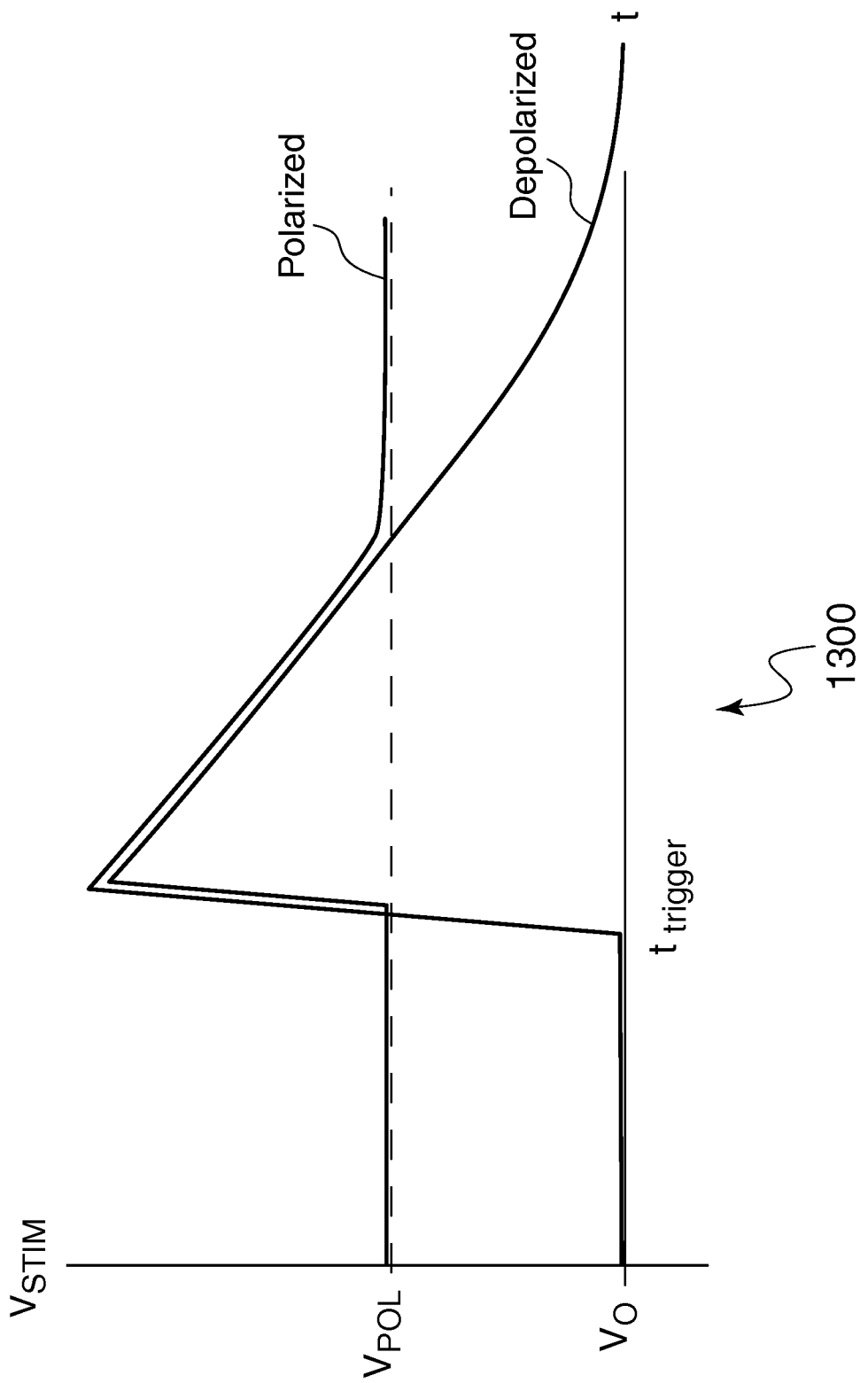
FIG. 13 is a graph depicting a stimulus voltage in accordance with an embodiment.

With reference to FIG. 13, a graph depicts an exemplary stimulus discharge in accordance with an embodiment. When a trigger signal is received, the stimulus capacitor discharges current between the electrodes. Depending on the tissue resistance, the voltage quickly returns to a rest voltage level at approximately the initial voltage level. When the frequency of the trigger signal is increased, a polarization effect causes the rest voltage to rise to a polarization voltage above the initial voltage. With a depolarization switch between the electrodes, each trigger signal causes the rest voltage to be re-established and lowered to about the initial voltage level.

Figure 14:
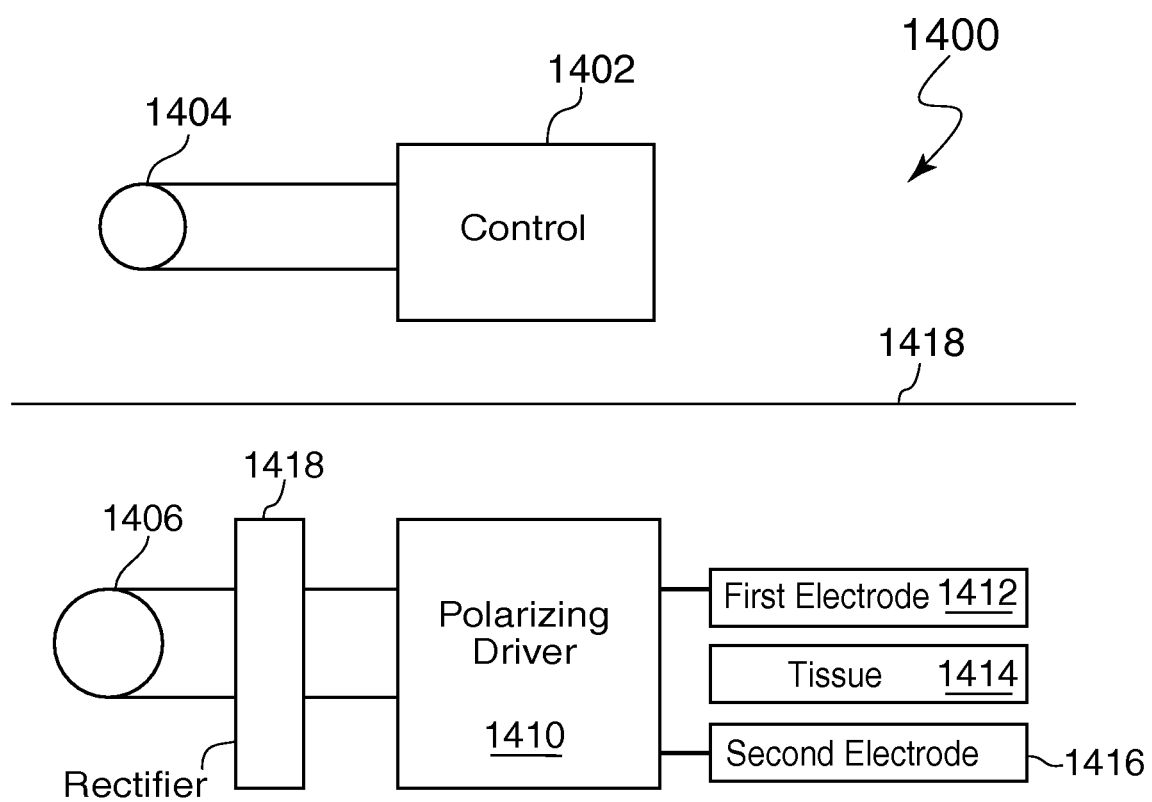
FIG. 14 is a block diagram depicting a microtransponder system, in accordance with an embodiment.

With reference to FIG. 14, a block diagram depicts a depolarizing microtransponder system 1400 in accordance with an embodiment. A control component energizes an external resonator element 1404 positioned externally relative to an organic layer boundary 1418. Energized, the external resonator element 1404 resonates energy at a resonant frequency, such as a selected RF. Internal resonator element 1406, positioned internally relative to an organic layer boundary 1418, is tuned to resonate at the same resonant frequency, or a harmonically related resonant frequency as the external resonator element 1404. Energized by the resonating energy, the internal resonator element 1406 generates pulses of energy rectified by a rectifier 1418. The energy may typically be stored and produced subject to timing controls or other forms of control. The energy is provided to the depolarizing driver 1410. A first electrode 1412 is polarized relative to a second electrode 1416 so that current is drawn through the tissue 1414 being stimulated, proximate to the electrode 1412 and 1416. The first electrode 1412 is polarized relative to the second electrode 1416 in the opposite polarization to draw an oppositely directed current through the tissue 1414, depolarizing the tissue 1414. The electrodes 1412 and 1416 may be typically made of gold or a platinum iridium alloy, or any other suitable material.

Figure 15:
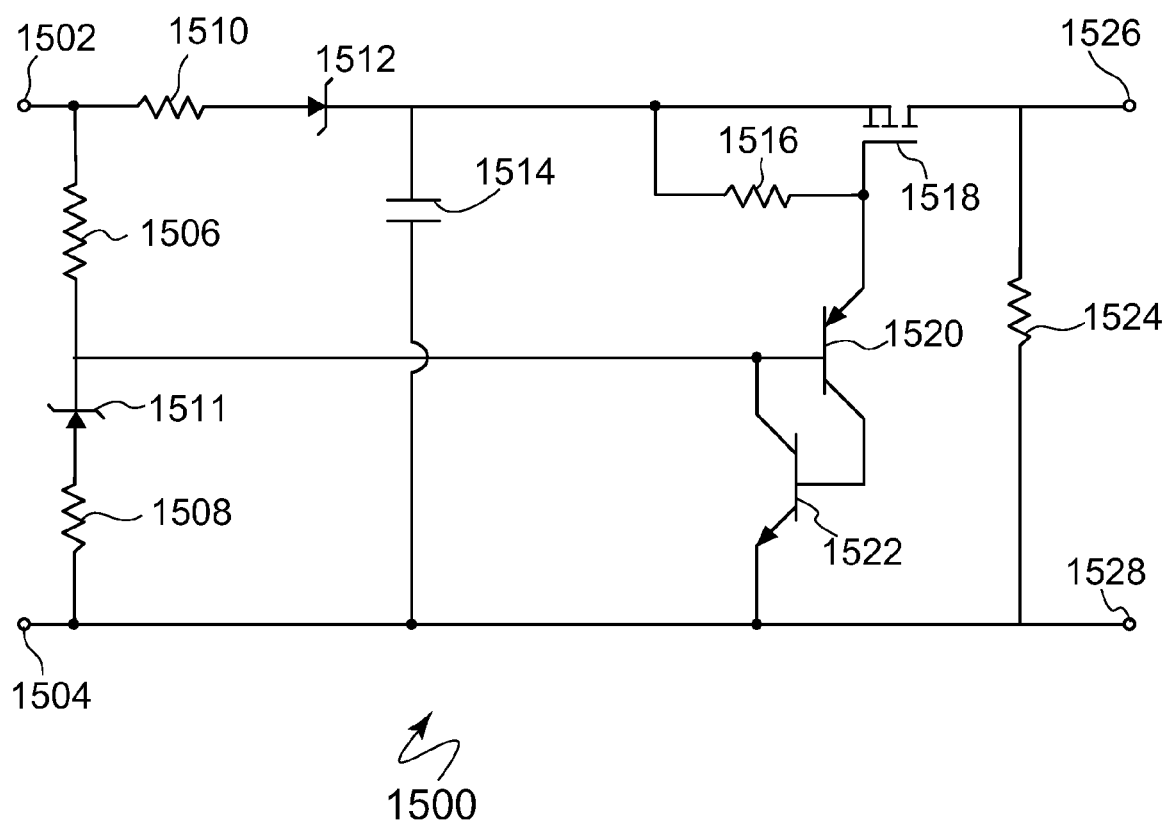
FIG. 15 is a circuit diagram depicting a driver circuit, in accordance with an embodiment.

With reference to FIG. 15, a circuit diagram depicts a depolarization driver circuit 1500, in accordance with an embodiment. A trigger signal is applied between electrodes 1502 and 1504. A charge capacitance 1514 is charged on the charge capacitance 1514. Schottky diode 1512 prevents the backflow of stimulus charge during the trigger phase. The charge rate is regulated by resistances 1510, 1506 and 1508. Resistances 1506 and 1508 form a voltage divider so that a portion of the trigger signal operate the bipolar switches 1520 and 1522. The trigger signal closes CMOS 1518 through resistance 1516, connecting the pulse between electrodes 1526 and 1528. A depolarization resistance 1524 is connected between the electrodes 1526 and 1528 to balance the charge stored in the tissue between the electrodes 1526 and 1528 between pulses. The specific breakdown voltage of the optional Zener diode 1511 provides for auto-triggering setting the upper limit of the voltage divider, at which point the bipolar switches are triggered by any further increase in the stimulus voltage. In addition to providing this auto-triggering feature for the purpose of asynchronous stimulation, the particular breakdown voltage of this Zener diode 1511 sets the maximum stimulus voltage. Otherwise the stimulus voltage is a function of the RF power level reaching the transponder from the external reader coil when the stimulus is triggered.

Figure 16:
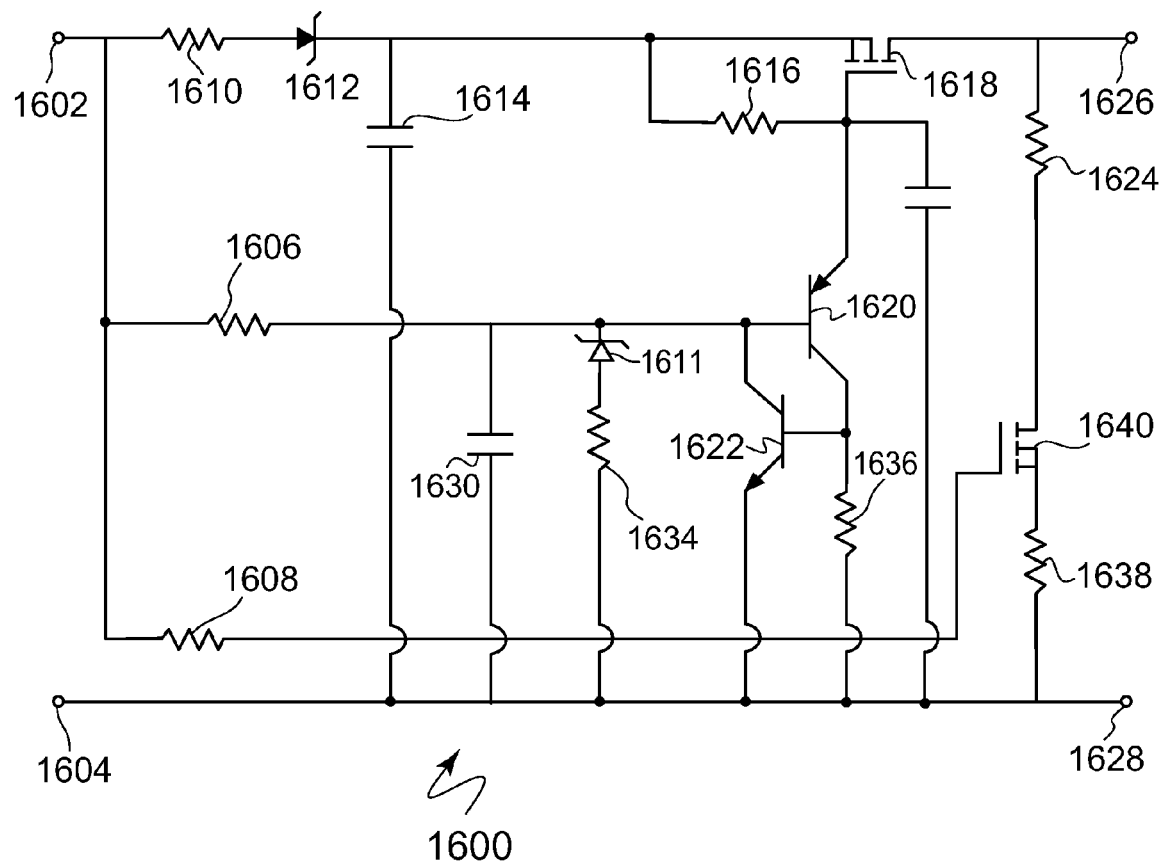
FIG. 16 is a circuit diagram depicting a driver circuit, in accordance with an embodiment.

With reference to FIG. 16, a circuit diagram depicts a depolarization driver circuit 1600, in accordance with an embodiment. A trigger signal is applied between electrodes 1602 and 1604. A charge capacitance 1614 is charged on the charge capacitance 1614. Schottky diode 1612 prevents the backflow of stimulus charge during the trigger phase. The charge rate is regulated by resistances 1610, 1606, 1634 and 1608. Resistances 1606 and 1608 form a voltage divider so that a portion of the trigger signal operate the bipolar switches 1620 and 1622. The trigger signal closes CMOS 1618 through resistance 1616, connecting the pulse between electrodes 1626 and 1628. Depolarization resistances 1624 and 1638 are connected to a depolarization CMOS 1640 between the electrodes 1626 and 1628 to balance the charge stored in the tissue between the electrodes 1626 and 1628 between pulses. The specific breakdown voltage of the optional Zener diode 1611 provides for auto-triggering setting the upper limit of the voltage divider, at which point the bipolar switches are triggered by any further increase in the stimulus voltage. In addition to providing this auto-triggering feature for the purpose of asynchronous stimulation, the particular breakdown voltage of this Zener diode 1611 sets the maximum stimulus voltage. Otherwise the stimulus voltage is a function of the RF power level reaching the transponder from the external reader coil when the stimulus is triggered.

Figure 17:
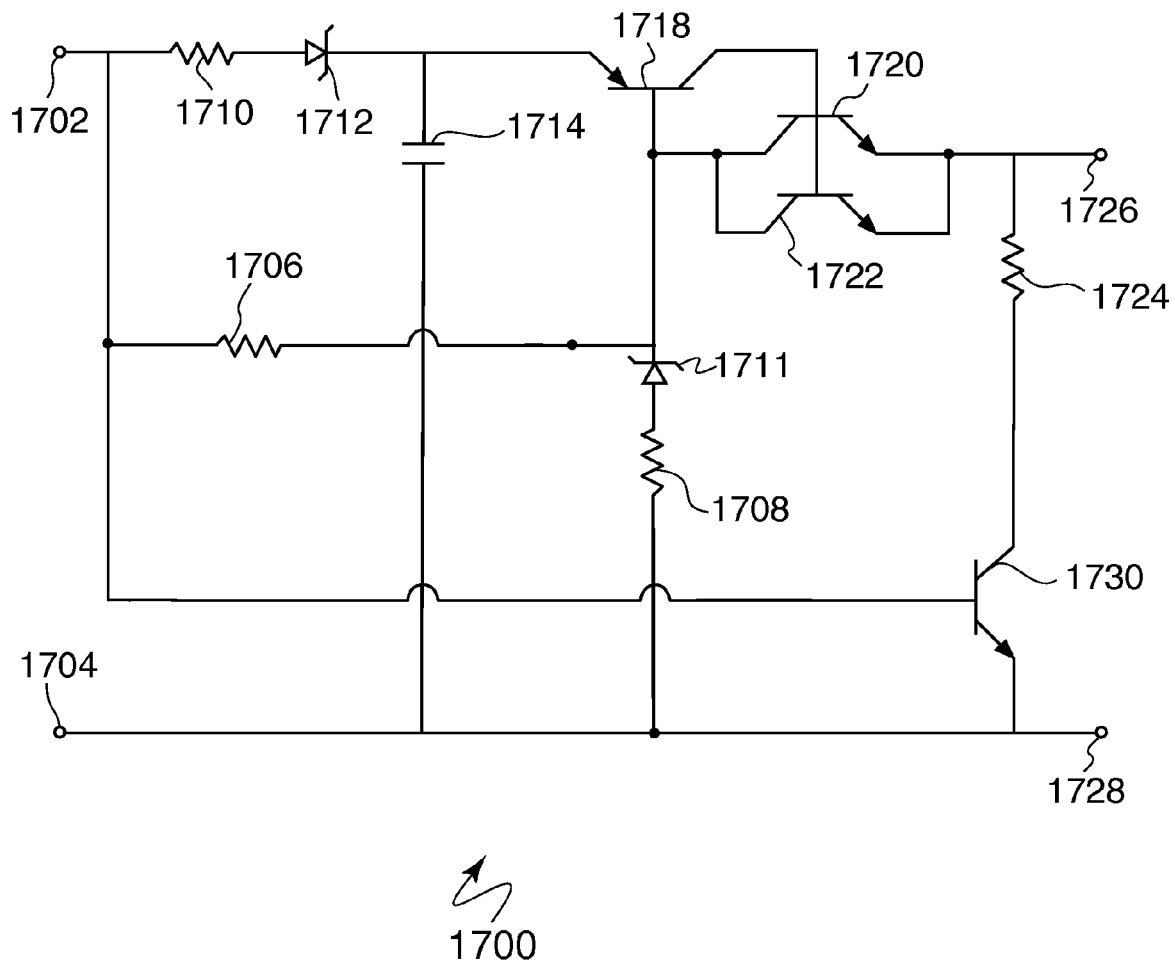
FIG. 17 is a circuit diagram depicting a driver circuit, in accordance with an embodiment.

With reference to FIG. 17, a circuit diagram depicts a depolarization driver circuit 1700, in accordance with an embodiment. A trigger signal is applied between electrodes 1702 and 1704. A charge capacitance 1714 is charged on the charge capacitance 1714. Schottky diode 1712 prevents the backflow of stimulus charge during the trigger phase. The charge rate is regulated by resistances 1710, 1706 and 1708. Resistances 1706 and 1708 form a voltage divider so that a portion of the trigger signal operate the bipolar switches 1720 and 1722. The trigger signal closes switch 1718 through resistance 1716, connecting the pulse between electrodes 1726 and 1728. A depolarization resistance 1724 is connected to a bipolar switch 1730 between the electrodes 1726 and 1728 to balance the charge stored in the tissue between the electrodes 1726 and 1728 between pulses. The specific breakdown voltage of the optional Zener diode 1711 provides for auto-triggering setting the upper limit of the voltage divider, at which point the bipolar switches are triggered by any further increase in the stimulus voltage. In addition to providing this auto-triggering feature for the purpose of asynchronous stimulation, the particular breakdown voltage of this Zener diode 1711 sets the maximum stimulus voltage. Otherwise the stimulus voltage is a function of the RF power level reaching the transponder from the external reader coil when the stimulus is triggered.

Figure 18:
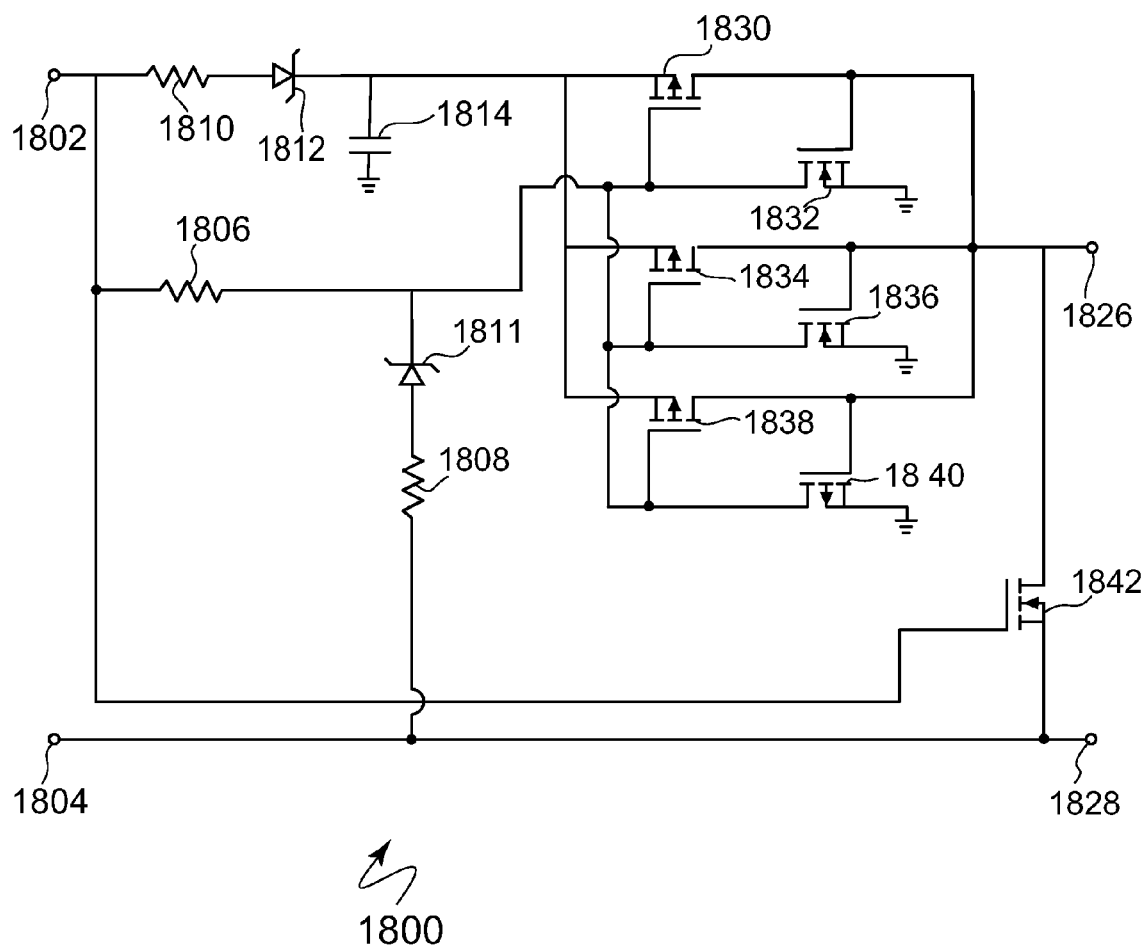
FIG. 18 is a circuit diagram depicting a driver circuit, in accordance with an embodiment.

With reference to FIG. 18A, a circuit diagram depicts a depolarization driver circuit 1800, in accordance with an embodiment. A trigger signal is applied between electrodes 1802 and 1804. A charge capacitance 1814 is charged on the charge capacitance 1814. Schottky diode 1812 prevents the backflow of stimulus charge during the trigger phase. The charge rate is regulated by resistances 1810, 1806 and 1808. Resistances 1806 and 1808 form a voltage divider so that a portion of the trigger signal operate the CMOS switches 1830, 1832, 1834, 1836, 1838 and 1840. The trigger signal closes CMOS 1830, 1834 and 1836 connecting the pulse between electrodes 1826 and 1828. A depolarization CMOS 1842 is connected between the electrodes 1826 and 1828 to balance the charge stored in the tissue between the electrodes 1826 and 1828 between pulses. The specific breakdown voltage of the optional Zener diode 1811 provides for auto-triggering setting the upper limit of the voltage divider, at which point the bipolar switches are triggered by any further increase in the stimulus voltage. In addition to providing this auto-triggering feature for the purpose of asynchronous stimulation, the particular breakdown voltage of this Zener diode 1811 sets the maximum stimulus voltage. Otherwise the stimulus voltage is a function of the RF power level reaching the transponder from the external reader coil when the stimulus is triggered.

Figure 35:
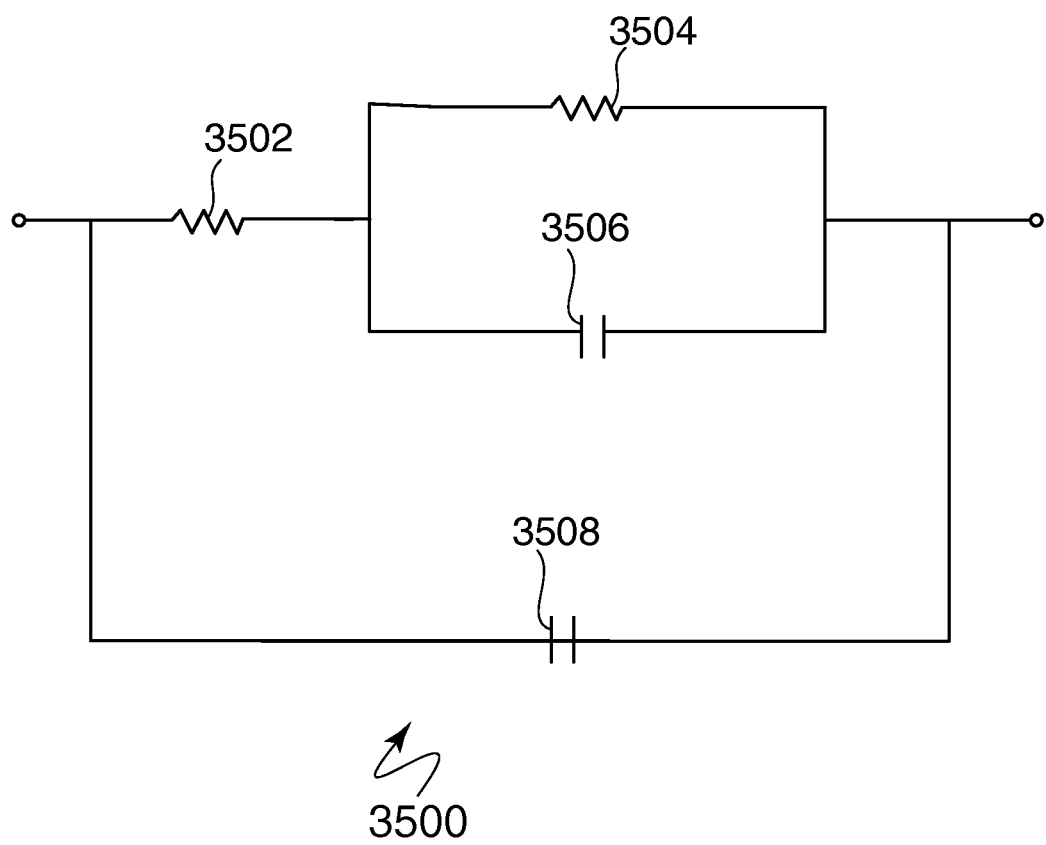
FIG. 35 is a circuit diagram depicting a tissue model.

With reference to FIG. 35, a circuit diagram depicts a tissue model. Depolarization becomes important because the tissue behaves as a non-linear load that can be modeled as shown. A resistance 3502 is in series with a resistance 3504 in parallel with a capacitance 3506. This arrangement is parallel to a second capacitance 3508. The capacitances 3506 and 3508 result in charge being stored in the circuit when an intermittent signal is applied, as happens in the tissue being stimulated by intermittent stimulation signals.

Figure 19A:
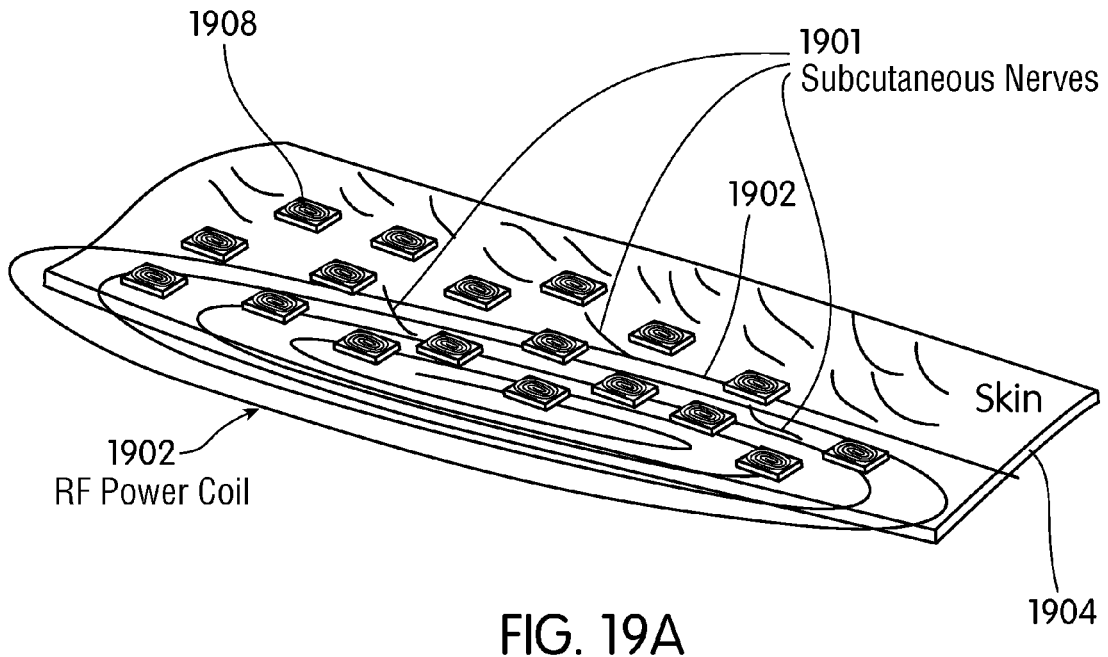
FIG. 19A is an illustration of a deployment of a plurality of wireless microtransponders distributed throughout subcutaneous vascular beds and terminal nerve fields consistent with the present innovations.

FIG. 19A is an illustration of a deployment of a plurality of wireless microtransponders distributed throughout subcutaneous vascular beds and terminal nerve fields, in accordance with one embodiment. As depicted, a plurality of independent wireless microtransponders 1908 are implanted subcutaneously in a spread pattern under the skin 1904 over the area that is affected by the chronic pain. Each microtransponder is positioned proximate to and/or interfaced with a branch of the subcutaneous sensory nerves 1901 to provide electrostimulation of those nerves. In one embodiment, only synchronous microtransponders are deployed. In another embodiment only asynchronous microtransponders are deployed. In yet another embodiment a combination of synchronous and asynchronous microtransponders are deployed.

After the deployment of the microtransponders, electrostimulation can be applied by positioning a RF power coil 1902 proximate to the location where the microtransponders are implanted. The parameters for effective electrostimulation may depend upon several factors, including: the size of the nerve or nerve fiber being stimulated, the effective electrode/nerve interface contact, the conductivity of the tissue matrix, and the geometric configuration of the stimulating fields. While clinical and empirical studies have determined a general range of suitable electrical stimulation parameters for conventional electrode techniques, the parameters for microscale stimulation of widely distributed fields of sensory nerve fibers are likely to differ significantly with respect to both stimulus current intensities and the subjective sensory experience evoked by that stimulation.

Parameters for effective repetitive impulse stimulation using conventional electrode techniques are typically reported with amplitudes ranging from up to about 10 V (or up to about 1 mA) lasting up to about 1 millisecond repeated up to about 100 pulses/s for periods lasting several seconds to a few minutes at a time. In an exemplary embodiment effective repetitive impulse stimulation can be achieved with an amplitude of less than 100 µA and stimulation pulses lasting less than 100 µs.

Figure 19B:
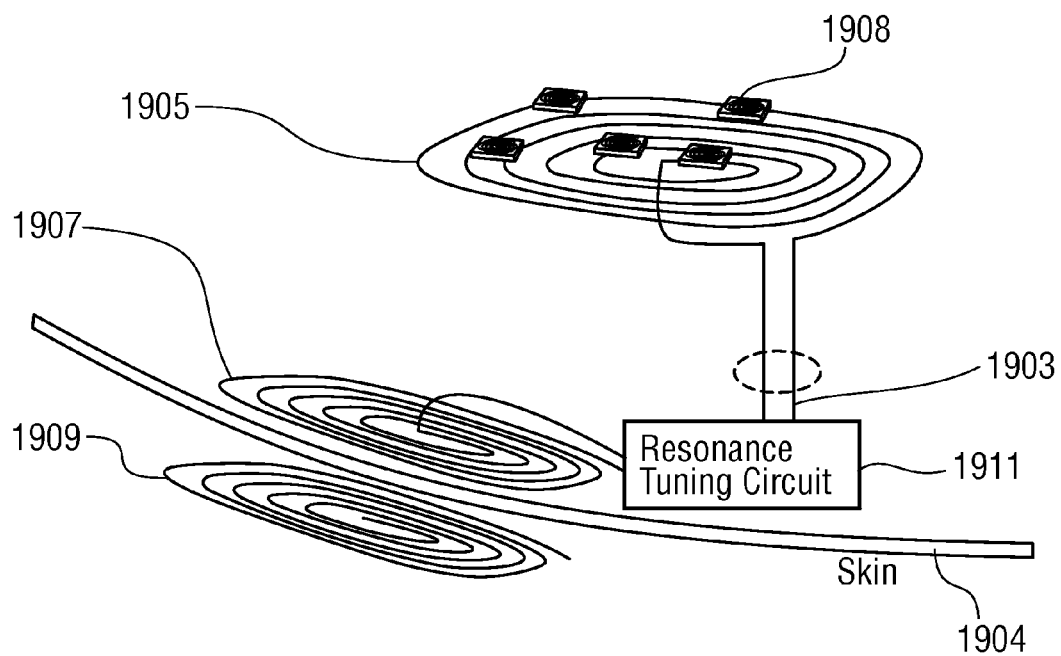
FIG. 19B is an illustration of a deployment of wireless microtransponders to enable coupling with deep microtransponder implants consistent with the present innovations.

FIG. 19B is an illustration of a deployment of wireless microtransponders to enable coupling with deep microtransponder implants, in accordance with one embodiment. As shown herein, two simple electrical wires 1903 lead from the subdermal/subcutaneous coil 1907 to the deeper site where a field of micro-transponders 1908 are implanted. Threading the wires 1903 through the interstitial spaces between muscles and skin involves routine minimally invasive surgical procedures as simple as passing the lead through hypodermic tubing, similar to routine endoscopic methods involving catheters. The minimal risks of such interstitial wires 1903 are widely accepted A deep coil 1905 is implanted to couple with the deeply implanted field of micro-transponders 1908 located near deep targets of micro-stimulation, such as deep peripheral nerves, muscles or organs such as the bladder or stomach as needed to treat a variety of clinical applications. The deep coil 1905 is tuned to extend the resonance of the external coil 1909 to the immediate vicinity of the implanted micro-transponders 1908 for maximal coupling efficiency. In addition to extending the effective range of the micro-transponder 1908 implants, the deep coil 1905 also provides another wireless link that can preserve the integrity of any further protective barrier around the target site. For instance, the deep coil 1905 can activate micro-transponders 1908 embedded within a peripheral nerve without damaging the epineurium that protects the sensitive intraneural tissues. To ensure optimal tuning of the transfer coils (e.g., the subdermal coil 1907) a variable capacitor or other tuning elements in a resonance tuning circuit 1911 are added to the subdermal coil 1907 where it can be implanted with minimal risk of tissue damage.

Figure 19C:
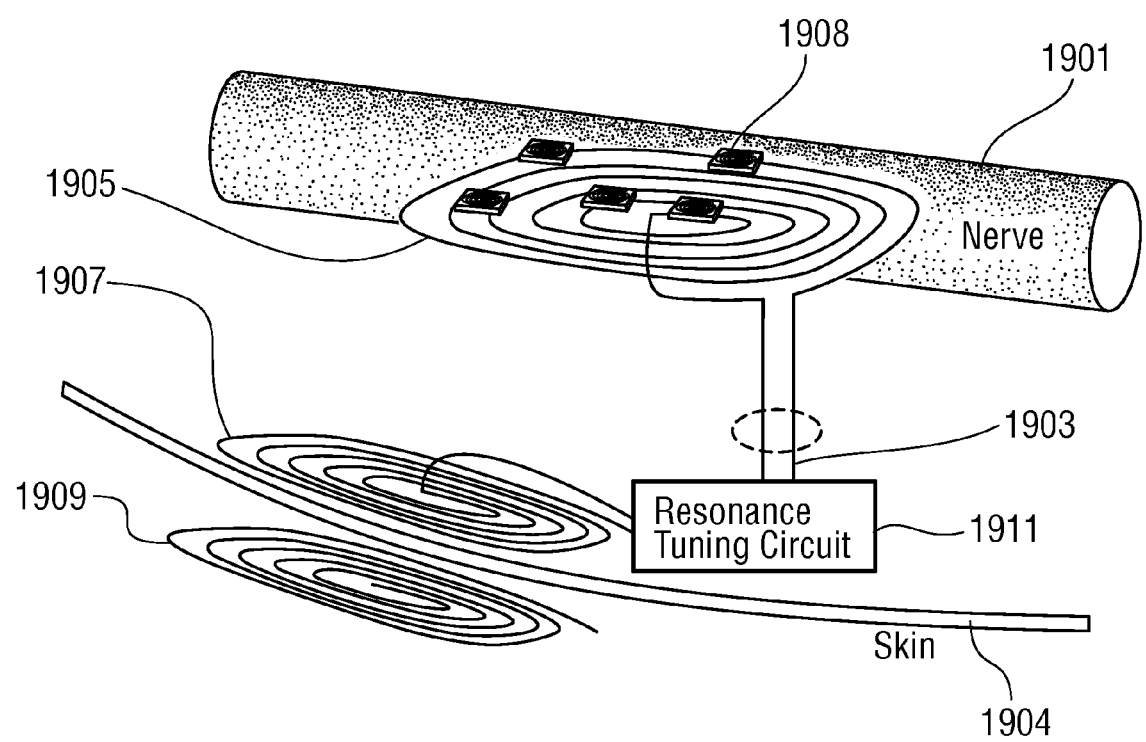
FIG. 19C is an illustration of a deployment of wireless microtransponders to enable coupling with deep neural microtransponder implants consistent with the present innovations.

FIG. 19C is an illustration of a deployment of wireless microtransponders to enable coupling with deep neural microtransponder implants, in accordance with one embodiment. As shown herein, an extraneural interface coil 1905 positioned proximate to (or interfaced with) a nerve fiber or cell cluster 1901 is interconnected to a subcutaneous relay coil 1907 by a simple pair of leads 1903 that mediate all the signals and power necessary to operate micro-transponders 1908 implanted anywhere in the body, beyond the direct effective range of any external coil 1909 (e.g., epidermal coil, etc.). In addition to extending the effective range of the micro-transponder 1908 implants, the deep coil 1905 also provides another wireless link that can preserve the integrity of any further protective barrier around the target site. For instance, the deep coil 1905 can activate micro-transponders 1908 embedded within a peripheral nerve without damaging the epineurium that protects the sensitive intraneural tissues. In certain embodiments, the subdermal relay coil 1907 is tuned to the external coil 1909 and implanted immediately under the external coil 1909 just below the surface of the skin 1904 for maximum near-field wireless magnetic coupling. This allows the RF waves generated by the external coil 1909 to penetrate the body without long-term damage to the skin 1904 and the risk of infection. In other embodiments, the subdermal relay coil 1907 is tuned to the external coil 1909 and implanted deeper in the tissue subcutaneously.

Figure 20:
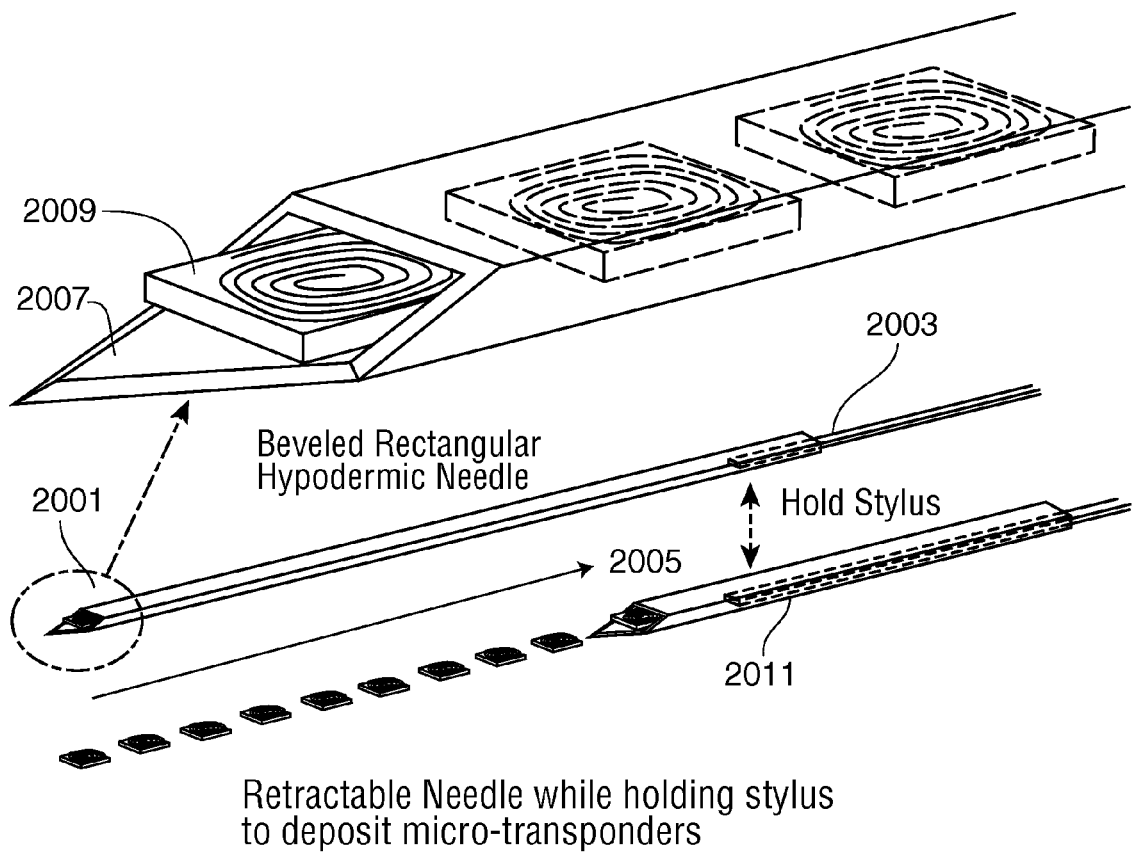
FIG. 20 shows an expanded view of an example of a microtransponder bio-delivery system.

FIG. 20 shows an example injection system 2000 comprising a loaded cannula 2005, stylet 2003 that can push through the cannula 2005. To safely insert a microstimulator/microtransponder to a body location cannula 2005 is designed to be in square and small diameter as the introducer with tapered dilator that does not have sharp edges. The front tip 2001 of Cannula 2005 may include an extruded edge 2007 that guides loaded micro-transponders 2009 into a target body location where the placement of microtransponders or array of microtransponders will likely be a drop-down placement. Microtransponders are deposited while pushing through stylet 2003 and retracting the needle/cannula 2005.

Cannula 2005 may also have the ability to retrieve a micro device array immediately or during the next 8-10 days, without a cut-down or reinserting another.

FIG. 20 is an illustration of how wireless microtransponders can be implanted using a beveled rectangular hypodermic needle, in accordance with one embodiment. As shown, the needle 2005 is curved to conform to the transverse cervical curvature (bevel concave) and without further dissection is passed transversely in the subcutaneous space across the base of the affected peripheral nerve tissue. Rapid insertion usually negates the need for even a short active general anesthetic once the surgeon becomes familiar with the technique. Following the placement of the microtransponders 2009 into the needle 2005, the needle 2005 is carefully withdrawn and the electrode placement and configuration is evaluated using intraoperative testing. Electrostimulation is applied using a temporary RF transmitter placed proximate to the location where the microtransponders 1003 are implanted, so the patient can report on the stimulation location, intensity, and overall sensation.

Figure 21:
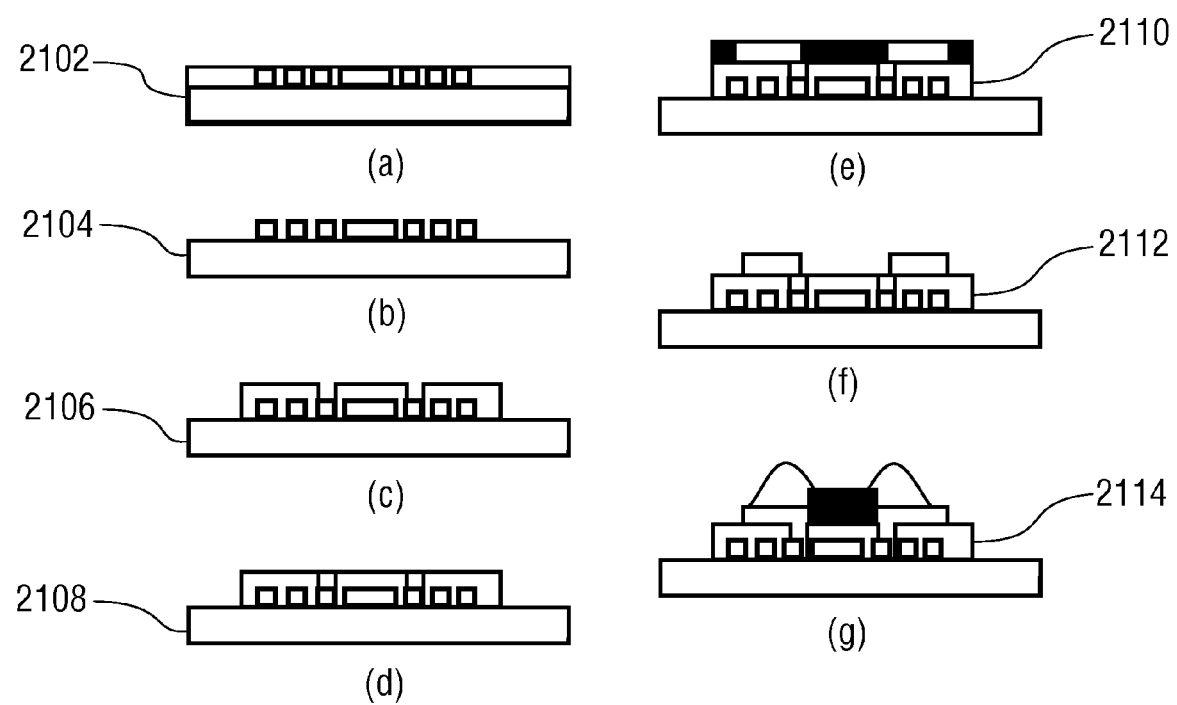
FIG. 21 is an illustration of a fabrication sequence for spiral type wireless microtransponders consistent with the present innovations.

FIG. 21 is an illustration of a fabrication sequence for spiral type wireless microtransponders, in accordance with one embodiment. At step 2102, a layer of gold spiral coil is electroplated onto a substrate (typically a Pyrex® based material, but other materials may also be used as long as they are compatible with the conducting material used for the spiral coil and the particular application that the resulting microtransponder will be applied to). Electroplated gold is used as the conductor material due to its high conductivity, resistance to oxidation, and proven ability to be implanted in biological tissue for long periods of time. It should be appreciated, however, that other conducting materials can also be used as long as the material exhibits the conductivity and oxidation resistance characteristics required by the particular application that the microtransponders would be applied to. Typically, the gold spiral coil conductors have a thickness of between approximately 5 µm to approximately 25 µm.

In one embodiment, the gold spiral coil takes on a first configuration where the gold conductor is approximately 10 µm wide and there is approximately 10 µm spacing between the windings. In another embodiment, the gold spiral coil takes on a second configuration where the gold conductor is approximately 20 µm wide and there is approximately 20 µm spacing between the windings. As will be apparent to one of ordinary skill in the art, however, the scope of the present invention is not limited to just these example gold spiral coil configurations, but rather encompasses any combination of conductor widths and winding spacing that are appropriate for the particular application that the coil is applied to.

In step 2104, the first layer of photoresist and the seed layer are removed. In one embodiment, the photoresist layer is removed using a conventional liquid resist stripper to chemically alter the photoresist so that it no longer adheres to the substrate. In another embodiment, the photoresist is removed using a plasma ashing process.

In step 2106, an isolation layer of SU-8 photo resist is spun and patterned to entirely cover each spiral inductor. Typically, the SU-8 layer has a thickness of approximately 30 µm. In step 2108, a top seed layer is deposited on top of the SU-8 isolation layer using a conventional physical vapor deposition (PVD) process such as sputtering. In step 2110, a top layer of positive photoresist coating is patterned onto the top see layer and the SU-8 isolation layer, and in step 2112, a layer of platinum is applied using a conventional electroplating process. In step 2114, a chip capacitor and a RFID chip are attached to the platinum conducting layer using epoxy and making electrical connections by wire bonding. In certain embodiments, the capacitor has a capacitance rating value of up to 10,000 picofarad (pF).

It is possible to implant such small microtransponders by simply injecting them into the subcutaneous tissue. Using local anesthesia at the injection site, the patient may be positioned laterally or prone depending on the incision entry point. The subcutaneous tissues immediately lateral to the incision are undermined sharply to accept a loop of electrode created after placement and tunneling to prevent electrode migration. A Tuohy needle is gently curved to conform to the transverse posterior cervical curvature (bevel concave) and without further dissection is passed transversely in the subcutaneous space across the base of the affected peripheral nerves. Rapid needle insertion usually obviates the need for even a short acting general anesthetic once the surgeon becomes facile with the technique. Following placement of the electrode into the Tuohy needle, the needle is withdrawn and the electrode placement and configuration is evaluated using intraoperative testing.

After lead placement, stimulation is applied using a temporary RF transmitter to various select electrode combinations enabling the patient to report on the table the stimulation location, intensity and overall sensation. Based on prior experience with wired transponders, most patients should report an immediate stimulation in the selected peripheral nerve distribution with voltage settings from 1 to 4 volts with midrange pulse widths and frequencies. A report of burning pain or muscle pulling should alert the surgeon the electrode is probably placed either too close to the fascia or intramuscularly.

An exemplary microtransponder array preferably is an array of joined microtransponders. The joined array is made from or coated with biocompatible material that is sufficiently strong to hold the microtransponders and remain intact during surgical explanation. An advantage of the joined array is that removal of the array is simpler than unjoined microtransponders, which would be more difficult to locate and individually extract from the integrated mass of adhered tissues. The concept is flexible, as the array may comprise a joined array of any type of implanted medical devices.

The joined array can be made from several types of biocompatible materials. Exemplary synthetic materials suitable for the removable array include silicone elastomers, or silicone hydrogels, and plastics such as SU-8, or parylene-C. Removable arrays may also be constructed using long-lasting biodegradable polymers including natural materials such as protein-based polymers like gelatin, silk or collagen, and sugar-based poly-saccharides like cellulose or agarose. Other suitable biodegradable polymers have been developed specifically for implant construction including poly-glycolic acids (PGA) and poly-lactic acids (PLA). Such construction materials offer a range of strengths, durability and tissue adhesion properties suitable for a variety of specific implant applications. Furthermore, the surface of any array material may be enhanced to promote specific biological properties such as cell/protein adhesion and tissue reactions by coating the implant with a variety of materials widely employed for this purpose including formulations of PEG (polyethylene glycol) such as PEG-PLA, and commercial products such as Greatbatch Biomimetic Coating (U.S. Pat. No. 6,759,388 B1), and Medtronics' Trillium Biosurface.

Biocompatibility of the array is very important. The linked array can include a coating in the form of a monolayer or thin layer of biocompatible material. Advantages that coatings offer include the ability to link proteins to the coating. The linked proteins can limit what cell types can adhere to the array. The coating can prevent protein adsorption, and it does not significantly increase size of the device.

3-D porous materials are meant to encourage cell ingrowth and organization. The 3-D porous material can act as a buffer between the tissue and microtransponders to prevent reaction micromotion. The potential benefits for implant/tissue integration must be balanced against the addition risks associated with increasing the overall size of the implant with the additional risks associated with increasing the overall size of the implant with the addition of such 3-D materials.

The visibility of the implant may be enhanced by adding brightly colored dyes to the construction materials thereby facilitating visual location of the array within surrounding tissue in case it must be removed. This can include a marker dye incorporated onto, or into, the device globally. A preferred embodiment would employ a fluorescent dye that becomes visible when exposed to appropriate light sources because it offers the advantage of maximum luminescence to such a level that implants may be visible through the skin.

Figure 22:
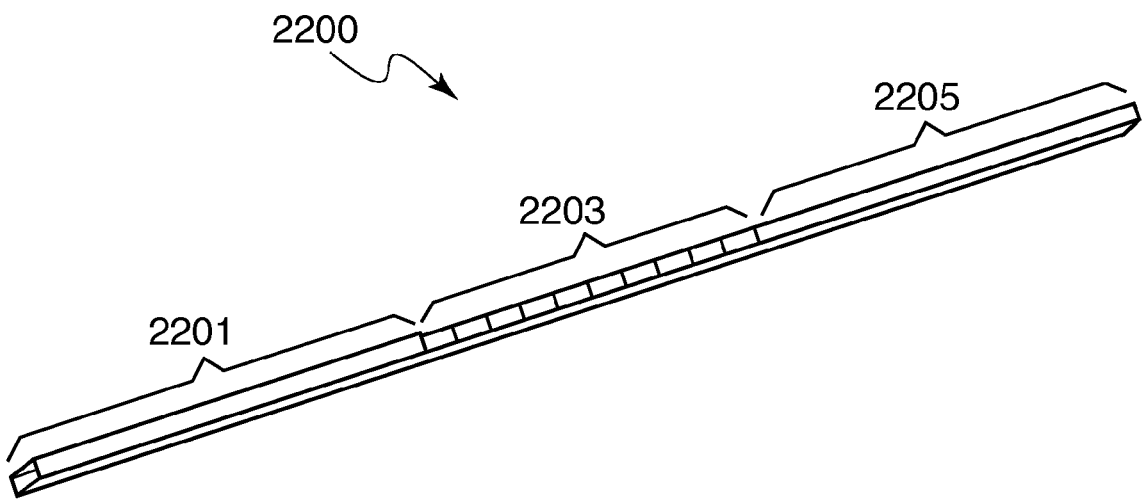
FIG. 22 shows an example of loading a hypodermic cannula with micro-transponder array during manufacturing process.
Figure 23:
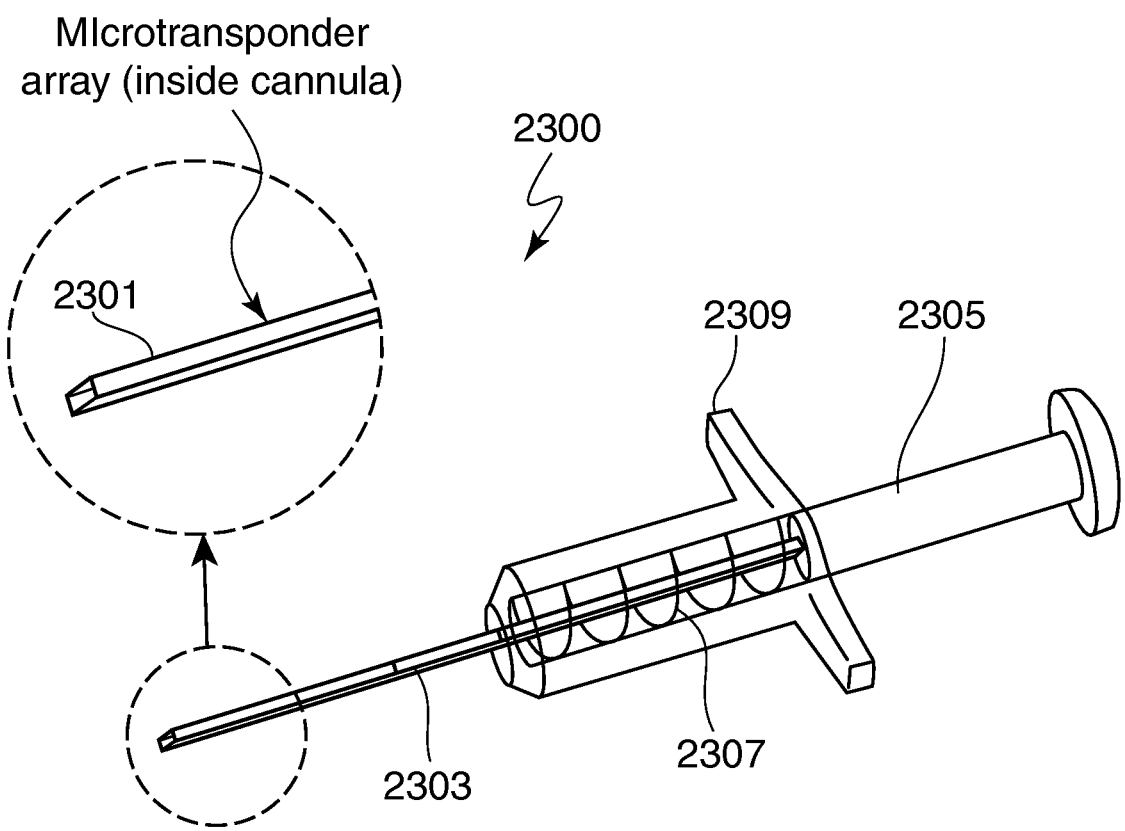
FIG. 23 shows an example of a micro-transponder ejection system.

The array of microtransponders is loaded into the injection system during the manufacturing process. FIG. 22 shows an example of pre-loading micro-transponder array 2203 into Cannula 2201 with or without the attachment of stylet 2205. FIG. 23 shows another example of pre-packaged injection system which has a stylet 2303 attached to syringe-like device where a handle holder 2309, a spring 2307 and a handle 2305 for injection. The whole package is sterilized. Preloaded delivery system may be disposable and used only once. After the manufacturing process is completed, the array 2301 will be ready for implantation after removal from the packaging.

The internal compression spring 2307 will keep the injection system from accidentally dispensing the array during shipment and handling. A needle cap may be used to prevent accidental dispensing and sharps protection.

Figure 24:
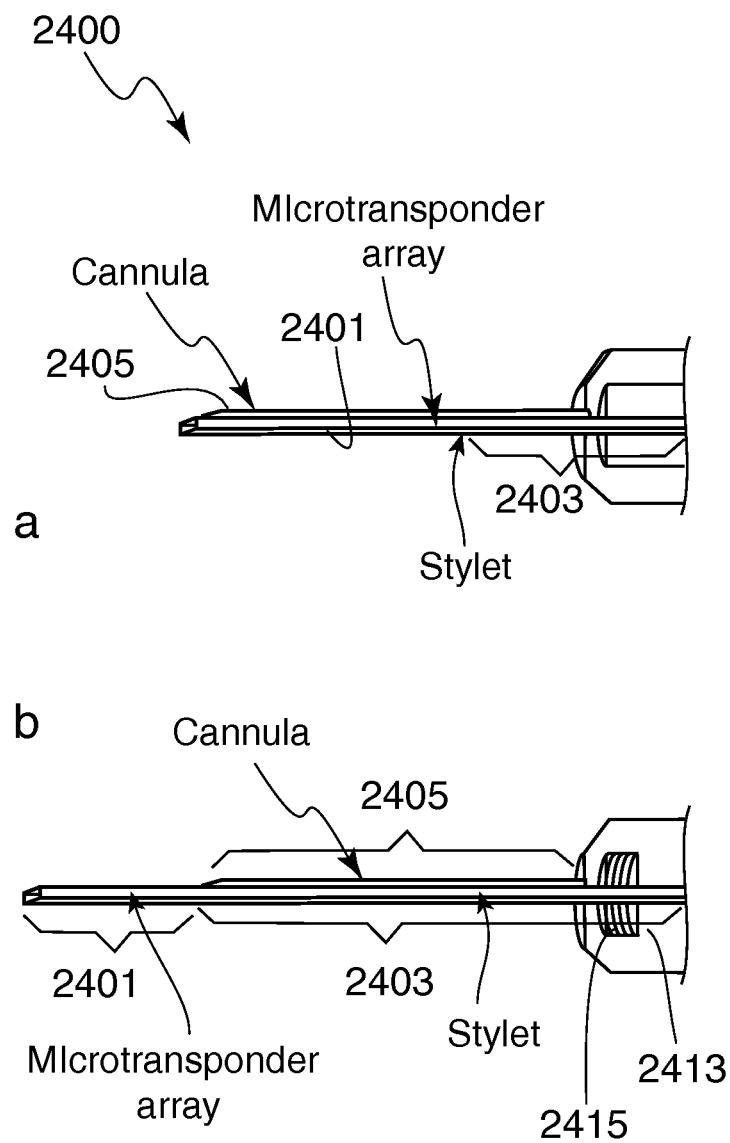
FIG. 24(a) shows a cross-sectional view of an example of micro-transponder implantation process.
FIG. 24(b) shows a cross-sectional view of a micro-transponder ejection system immediately after an implantation process.
Figure 25:
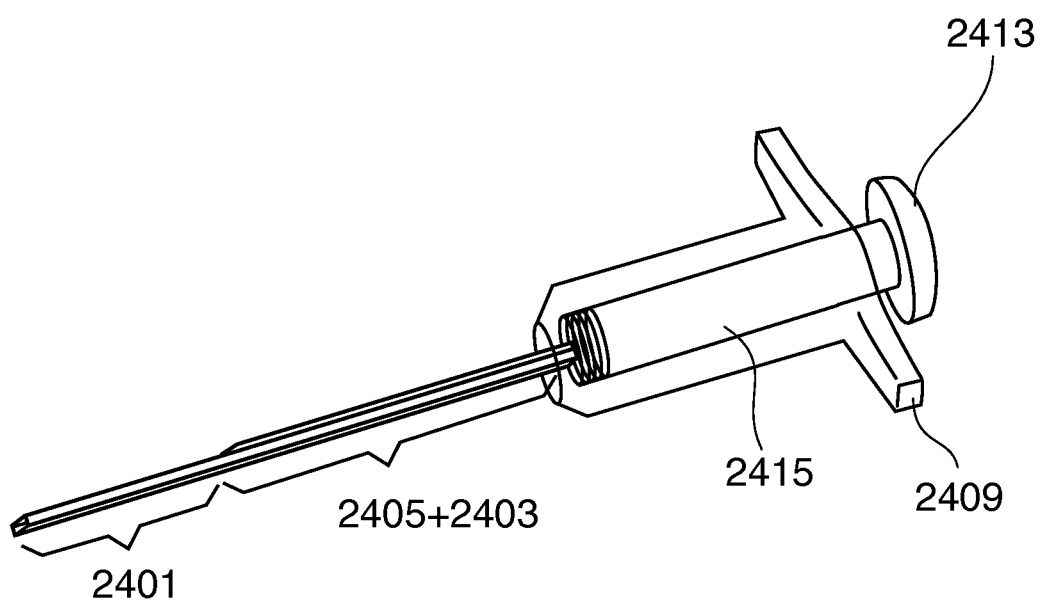
FIG. 25 shows an example of a micro-transponder ejection system immediately after ejection.

FIG. 24(*a*) shows a preloaded injection system with a relaxed spring. FIG. 24(*b*) shows that after inserting the needle/cannula 2405 into the tissue, handle 2413 is pushed compressing the spring 2415 and stylet 2403 and pushing microtransponder array 2401 into the tissue. After the injection into the tissue, handle holder 2409 is used to retract cannula 2405, leaving the injection array in the tissue. FIG. 25 shows an example look of the injection system immediately after the micro-transponder ejection.

Materials for the construction of the injection system are biocompatible, for example the cannula and stylet can be stainless steel and the handle and the handle holder can be acrylonitrile butadiene styrene (ABS), polycarbonate, or polyurethane. The stylet may also be made of bio-compatible plastics. Sterilization can be Conducted and verified according to standard GMP procedure required by FDA for the intended production environment and processes and purposes.

During pre-loading process, the cannula and stylet may need to be fabricated from custom extruded material, so that there is limited space between the array and the walls of the cannula. A biocompatible lubrication material, such as polyethylene glycol (PEG), may be used to reduce the friction between the array and the cannula.

The foreign body response (FBR) is one of the primary modes of failure for electrical implants. Generally this response is triggered by absorbance and denaturation of proteins on the implanted substrate, followed by activation of neutrophils and macrophages. Macrophages that are unable to phagocytose the implant begin fusing to form foreign body giant cells, which release free radicals that may damage the implanted device. Often this is followed by the formation of a fibrous or glial scar which encapsulates the device and segregates it from the target tissue.

It has been shown that both porous scaffold materials and non-fouling coating can reduce the host FBR. A multitude of unique materials and designs have been tested for this purpose. It is desirable to not only reduce the FBR, but also to encourage intimate contact between the implanted devices and target tissues. The primary drawback with previous strategies encouraging tissue integration with implants, is that they can only be removed by excision of actual tissue. This application discloses a novel design to both encourage tissue integration and facilitate removal of devices in the event of failure, patient paranoia, or completion of therapy.

Figure 26:
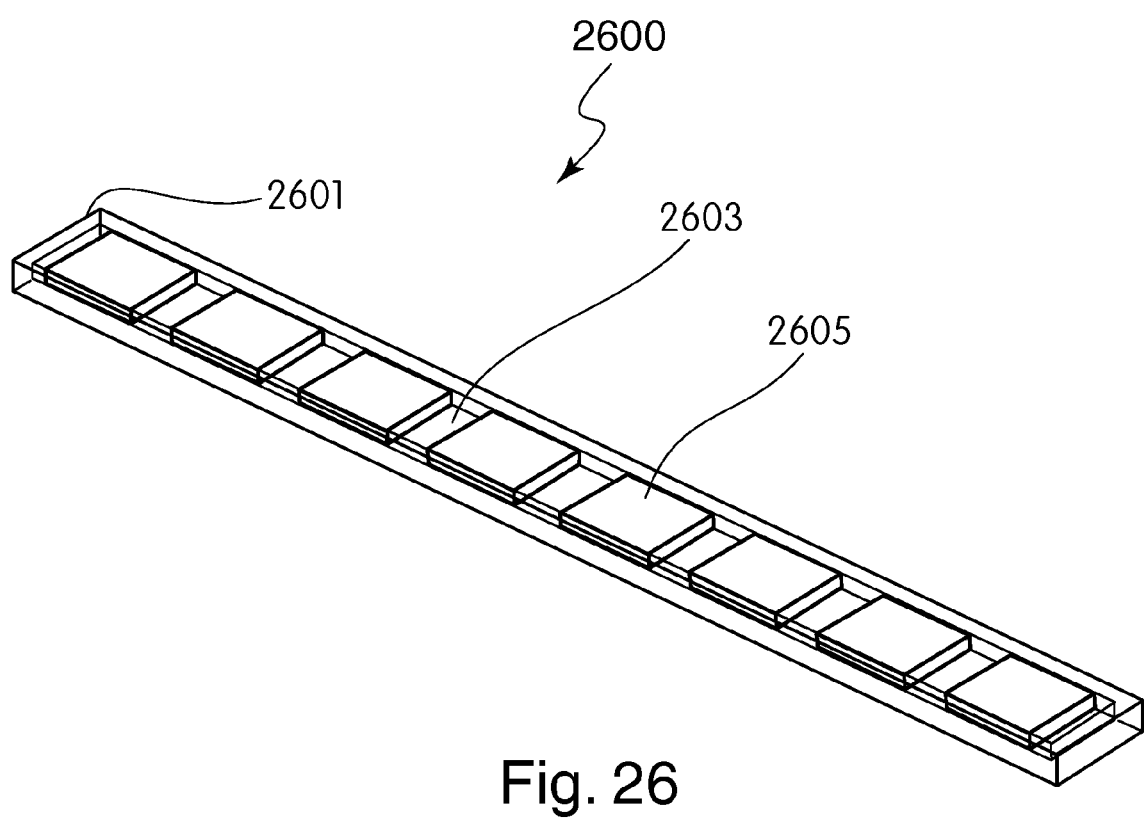
FIG. 26 shows an example of a micro-transponder array.
Figure 27A:
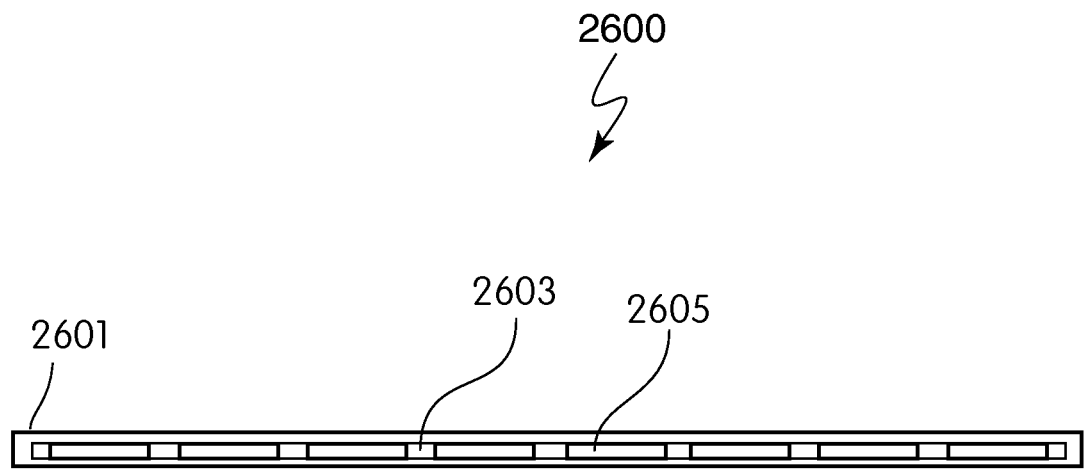
FIG. 27(a) shows a side view of the micro-transponder array of FIG. 26.
Figure 27B:
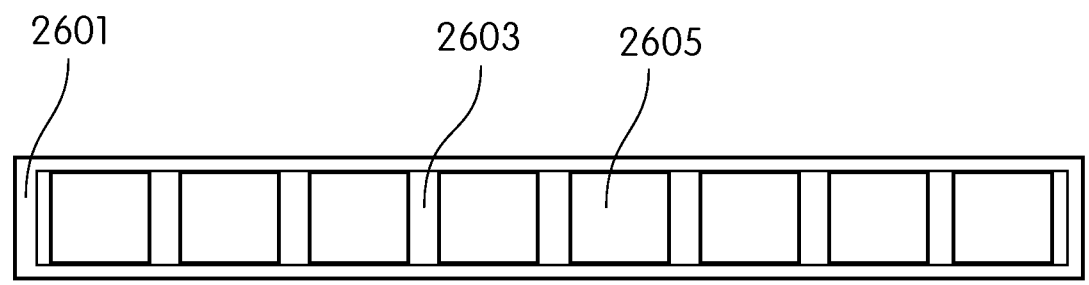
FIG. 27(b) shows a plan view of the micro-transponder array of FIG. 26.

To accomplish this end, as shown in FIGS. 26 and 27, a plurality of individual microtransponders 2605 can be linked together to form an array and a core strip 2603 by a durable non-fouling material, for example, SU8 with the surface coated with a lubricating, protein adsorption preventing, "stealth" material. The core strip is then embedded within a porous scaffold 2601. The core material will be fabricated from a material (or coated with) that will minimize adhesion with the scaffold and in-growing tissue. Biocompatible material that will encourage growth of surrounding tissue up to the implanted devices and exposed SU8 is used for the scaffold which is designed in a manner to both minimize FBR and encourage the penetration of endothelial cells and neurites. By separating the tissue integrating scaffolding from the solid core, removal of the actual devices can be carried out simply by making an incision to expose the end of the core, grasping it, and then sliding it out from the scaffolding.

Figure 28:
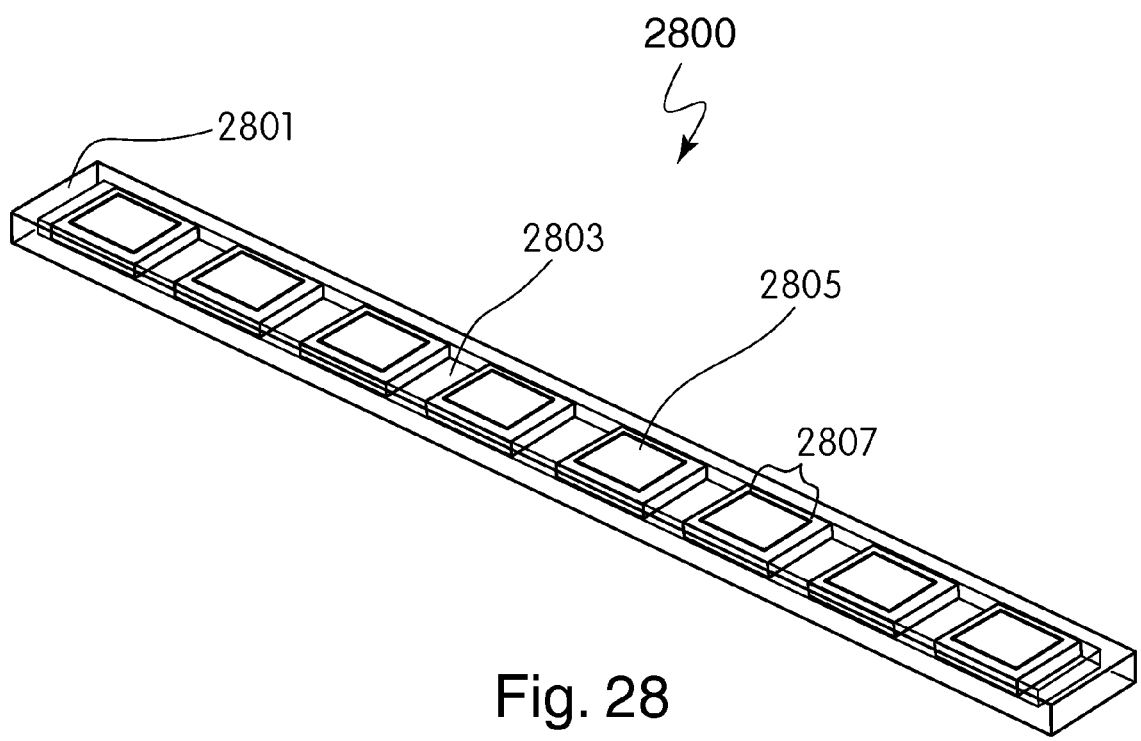
FIG. 28 shows another example of a micro-transponder array.
Figure 29A:
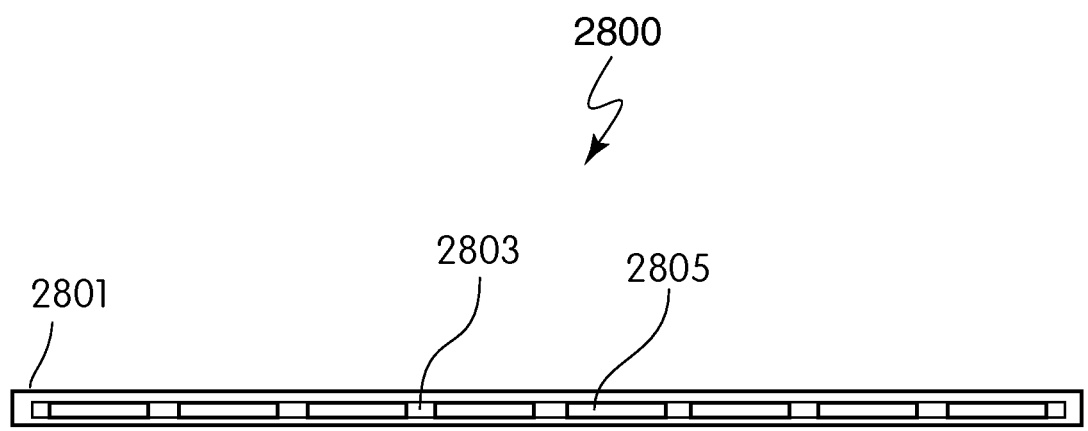
FIG. 29(a) shows a side view of the micro-transponder array of FIG. 28.
Figure 29B:
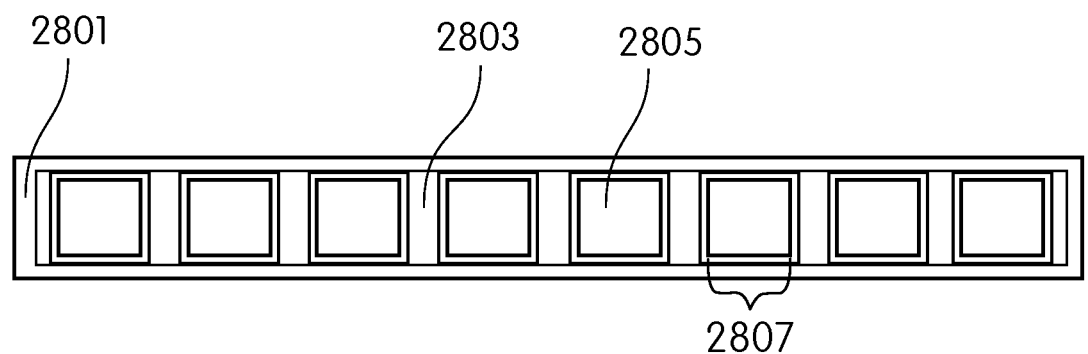
FIG. 29(b) shows a plan view of the micro-transponder array of FIG. 28.

Another embodiment of the micro-transponder array is shown in FIGS. 28 and 29. The core strip 2803 is a strong strip containing an embedded array of individual microtransponders, where the superior and inferior electrodes of microtransponders are exposed through "windows" 807. Electrode surfaces and strip may be coated with a lubricious, protein adsorption preventing, "stealth" material. The core strip is then embedded within a porous scaffold/matrix 2801 that the scaffolding will extend into the "windows." Other durable and more flexible material than SU8 can be used, and embedded microtransponders can be better protected. Electrodes of micro-transponders 2805 can be totally isolated from proteins/tissues, but still affect ions in solution.

Figure 30:
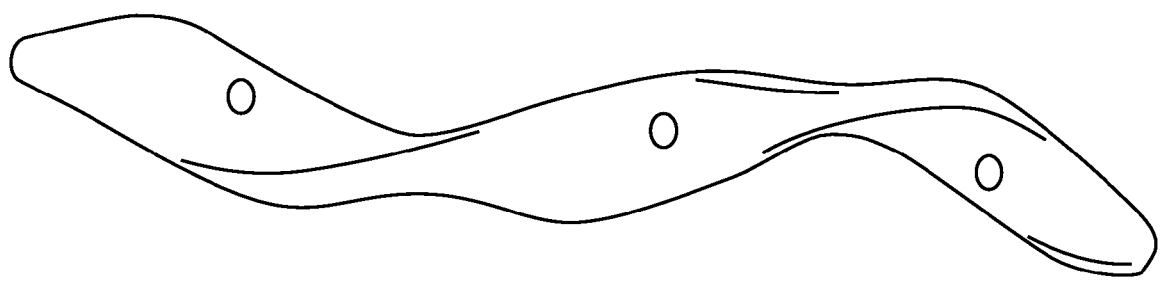
FIG. 30 shows a sectional view of another embodiment of a micro-transponder array.

Other designs suited to applications such as vagus nerve stimulation (which may be applied to peripheral nerves in general) may also be adopted and accommodated. A design shown in FIG. 30 that consists of a flexible helix containing exposed microtransponders on the inner surface, arranged in a manner such that all coils lay parallel to the overlying skin. The array of microtransponders may have linked electrodes so that they function as a single stimulator, to maximize stimulation around the entire periphery of the nerve. Sizes of microtransponders can be formed square form-factors of sizes (microns) such as 500×500; 1000×1000; 2000×2000, in rectangular form-factors of sizes (microns) such as 200×500; 250×750; 250×1000.

Figure 31:
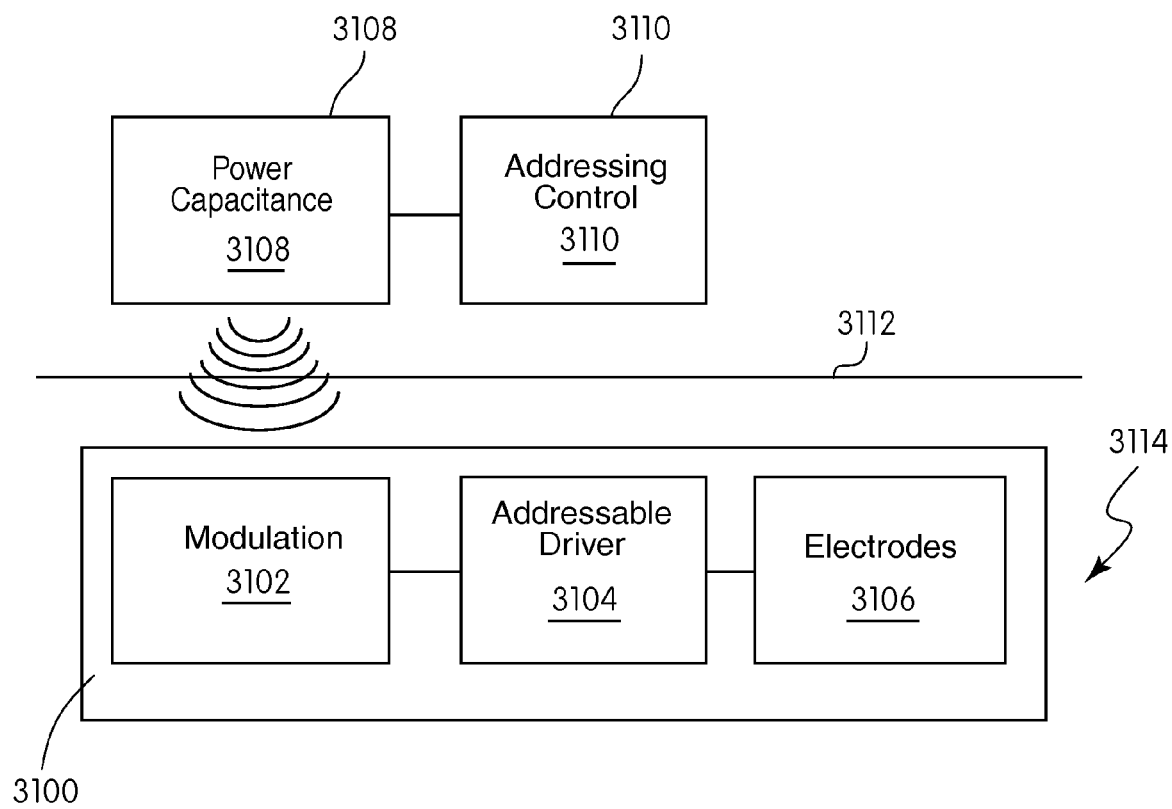
FIG. 31 is a block diagram showing an addressable transponder system, in accordance with an embodiment.

With reference to FIG. 31, a block diagram depicts an individually addressable wireless micro-transponder 3100, in accordance with an embodiment. The individually addressable wireless micro-transponder 3100 may typically include a resonant receiver 3102. The resonant receiver 3102 may be an inductance-capacitance (LC) circuit such as a tank circuit. The resonant receiver 3102 may be connected to an addressable driver 3104. The addressable driver 3104 may receive power, instructions and/or address information from the resonant receiver 3102. The addressable driver 3104 may receive instructions and/or address information from an external source other the resonant receiver 3102. In accordance with the address information received by the addressable driver 3104, the addressable driver 3104 may deliver an electrical current through the electrodes 3106. The passage of electrical current between the electrodes 3106 stimulates the tissue 3114 proximate to the electrodes 3106.

In accordance with an embodiment, the individually addressable wireless micro-transponder 3100 is embedded in human tissue 3114 beneath a layer of skin 3112. A resonant power source 3108 may be tuned to resonate electromagnetic energy at a frequency that generates power in the resonant receiver 3102 of the individually addressable wireless micro-transponder 3100. An addressing control module 3110 may be communicatively connected to the resonant power source 3108 and may provide addressed instructions to the resonant power source 3108 for relay to the resonant receiver 3102. Addressing control 3110 may communicate directly with the addressable driver.

Figure 32:
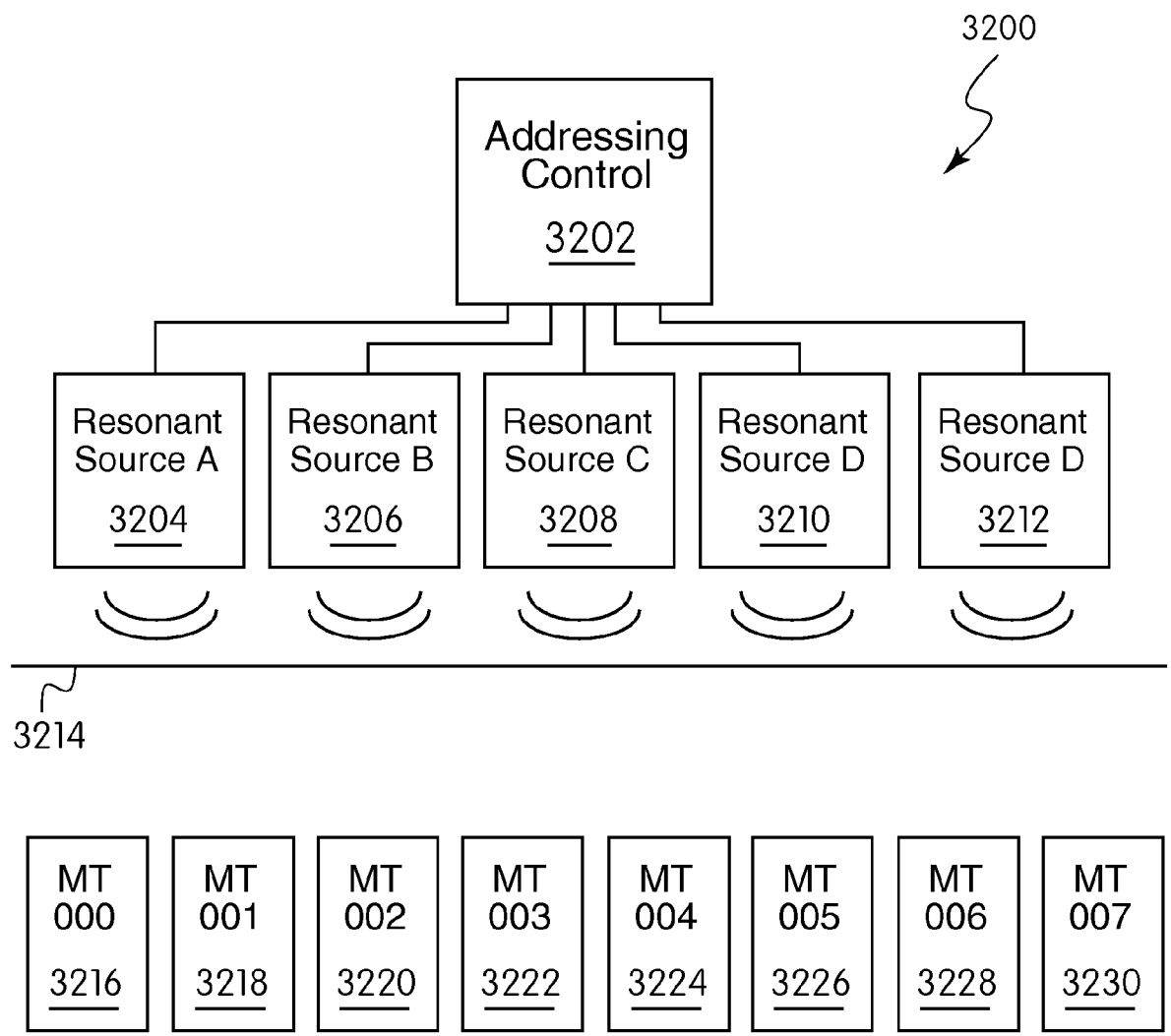
FIG. 32 is a block diagram showing an addressable transponder system, in accordance with an embodiment.

With reference to FIG. 32, a block diagram depicts an addressable wireless micro-transponder system 3200 in accordance with an embodiment. An addressing control module 3202 determines instructions for each of the implanted micro-transponders 3216, 3218, 3220, 3222, 3224, 3226, 3228 and 3230. The instructions in conjunction with the appropriate micro-transponder addresses are communicated to one or several resonant sources 3204, 3206, 3208, 3210 and 3212 in proximity to the addressed micro-transponders 3216, 3218, 3220, 3222, 3224, 3226, 3228 and 3230. For example, the addressing control module 3202 determines to send a stimulation pulse from micro-transponder 3222, having an address=003. The addressing control module 3202 may send an instruction for resonant source C 3208 to provide a signal including the address=003. Although micro-transponders 3220 and 3224 may be sufficiently proximate to the activated resonant source C 3208, only the micro-transponder 3222 having an address=3 will generate the stimulation pulse.

Figure 33:
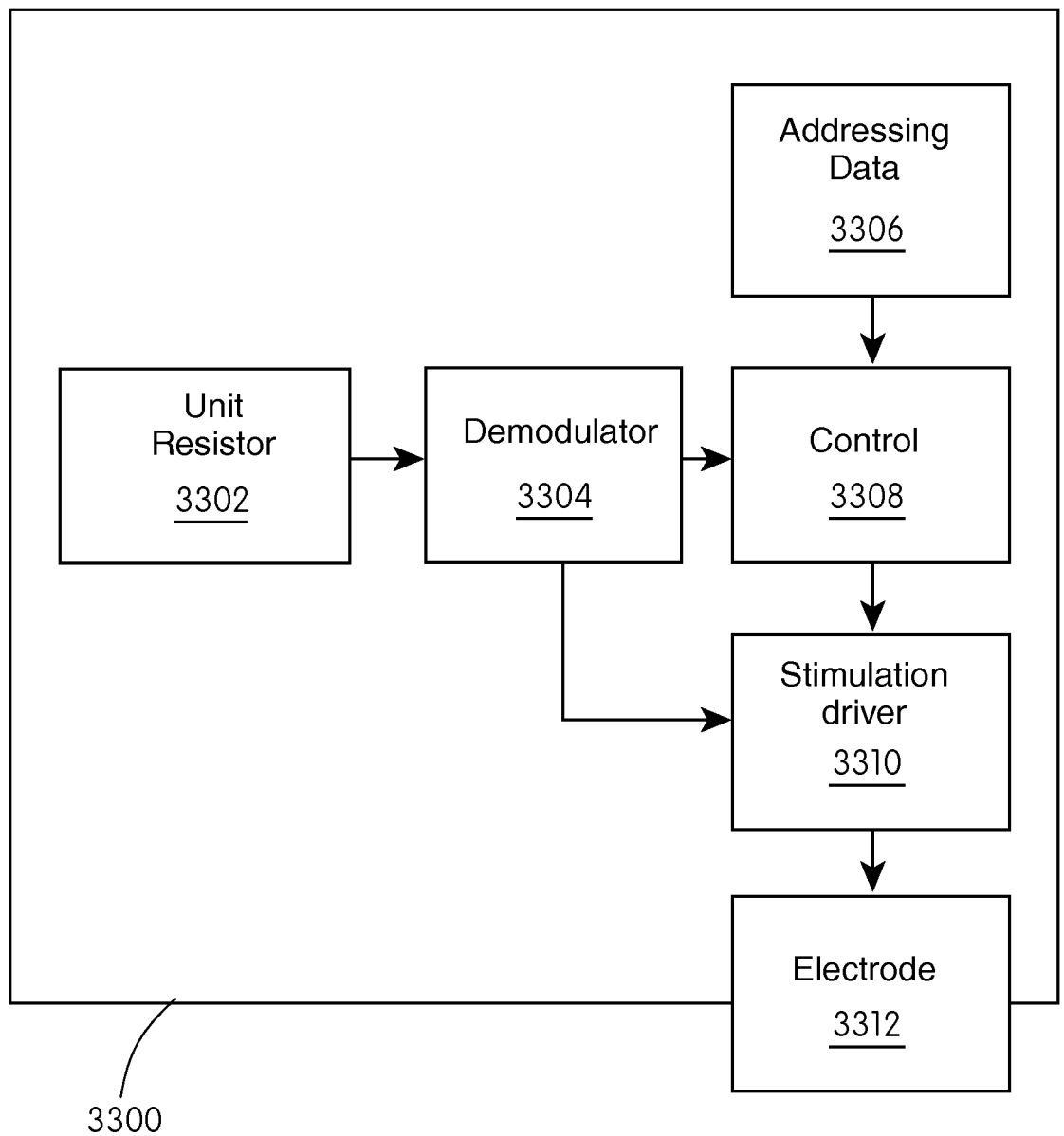
FIG. 33 is a block diagram showing an addressable transponder system, in accordance with an embodiment.

With reference to FIG. 33, a block diagram depicts an addressable micro-transponder 3300. A unit resonator 3302 receives resonated energy output to a demodulator 3304. The demodulator 3304 discriminates data content output to a control circuit 3308. The control circuit 3308 uses addressing data 3306 to filter stimulation instructions output to a stimulation driver 3310. The stimulation driver 3310 outputs a stimulation pulse to an electrode 3312.

Figure 34:
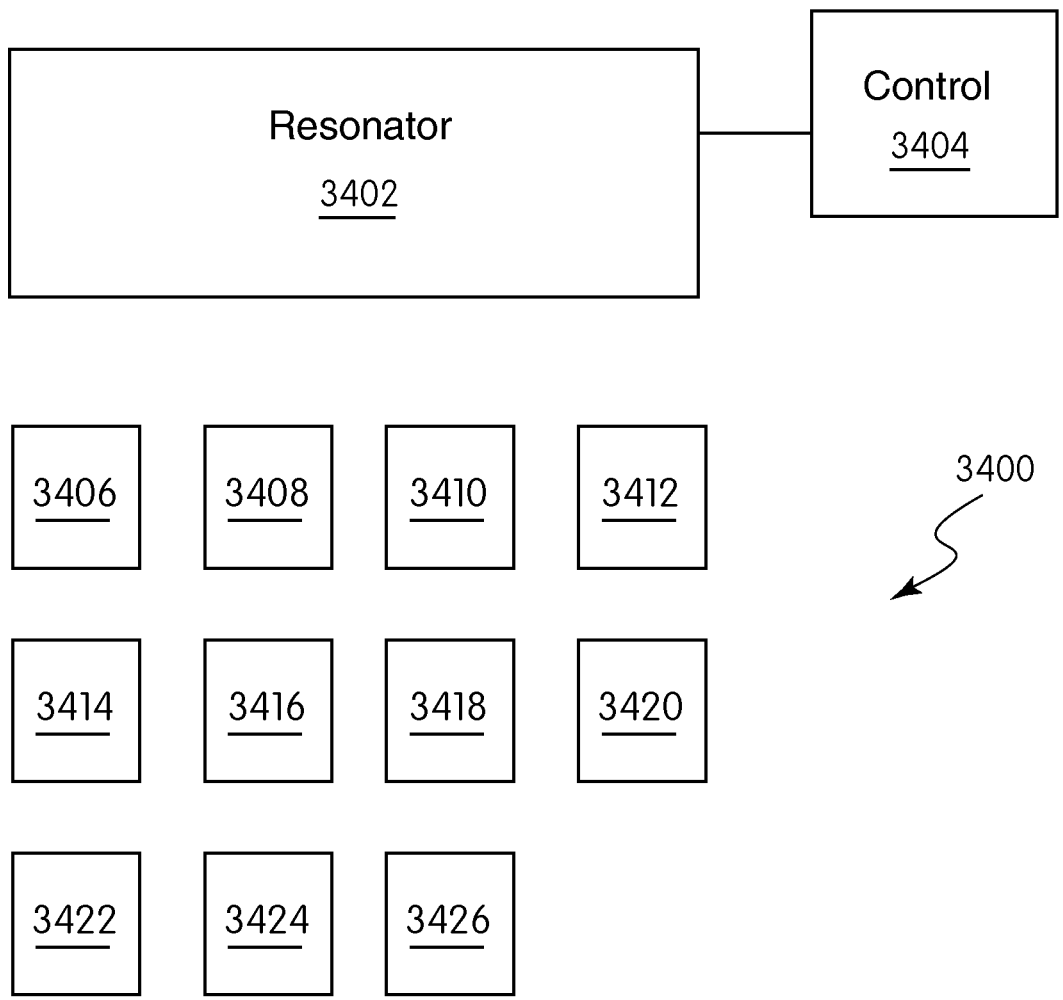
FIG. 34 is a block diagram showing an addressable transponder system, in accordance with an embodiment.

With reference to FIG. 34, a block diagram depicts an addressable micro-transponder system 3400. A resonator 3402 transmits resonant energy in accordance to instructions provided by a control 3404. The microtransponders 3406, 3408, 3410, 3412, 3416, 3418, 3420, 3422, 3424 and 3426 may be arranged in addressable groups. For example, microtransponders 3406, 3408, 3410 and 3412 may form a first group, addressable by a group address. Micro-transponders 3414, 3416, 3418 and 3420 may form a second group addressable by a second group address. Micro-transponders 3422, 3424 and 3426 my form a third group.

Figure 36:
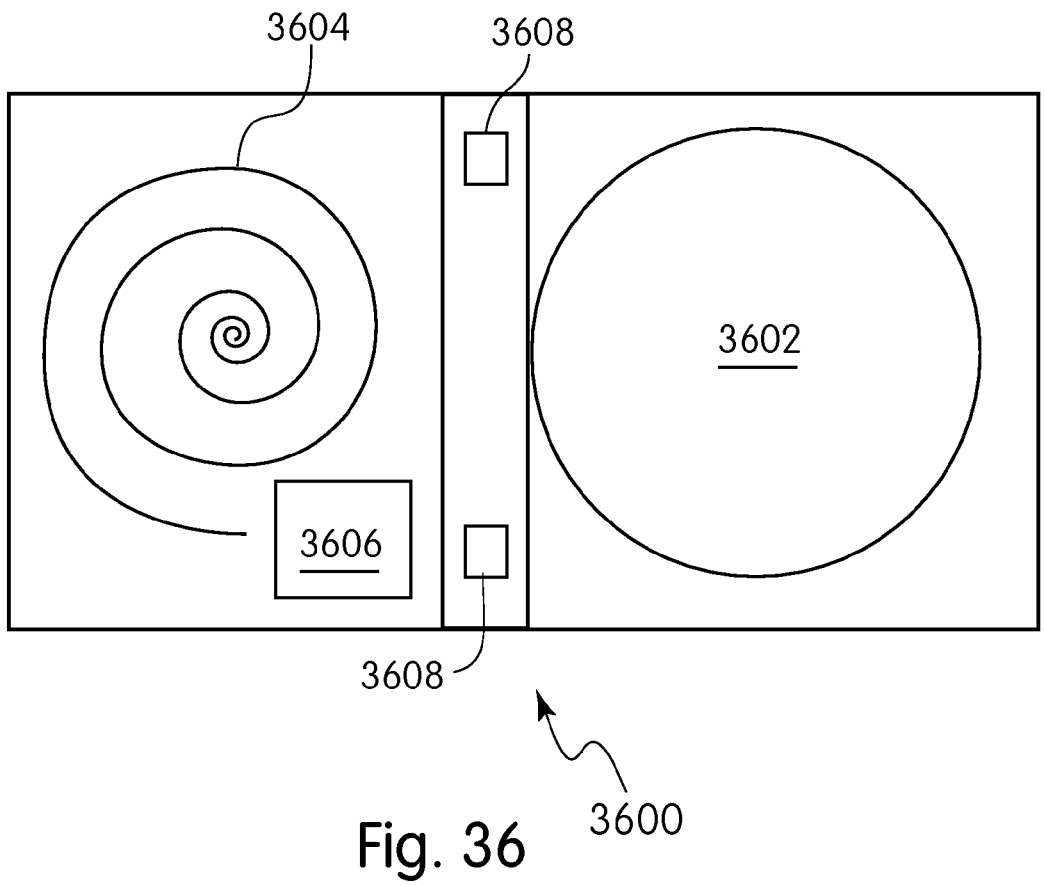
FIG. 36 is a wireless implant platform, in accordance with an embodiment.

With reference to FIG. 36, a wireless micro-implant platform 3600 is shown. The platform 3600 holds surface electrodes 3602 at one end of the platform 3600 and typically on both the top and the bottom side. An LC resonant circuit is formed with a spiral microcoil 3604 and a capacitance 3606. Rectifier diodes 3608 are positioned between the resonant circuit and the electrodes 3602. The surface electrodes 3602 may be used for neural stimulation, or any other suitable use.

Figure 37:
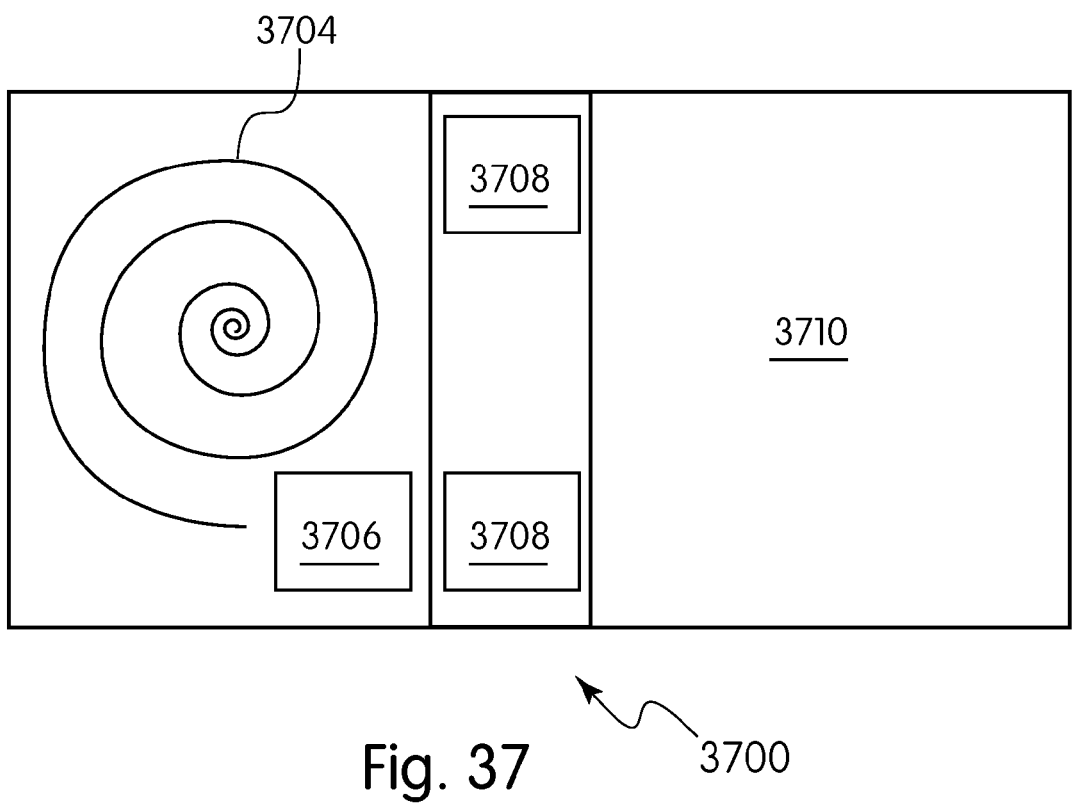
FIG. 37 is a wireless implant platform, in accordance with an embodiment.
Figure 12:
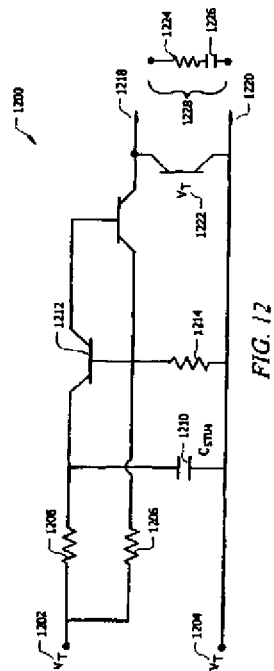
Figure 14:
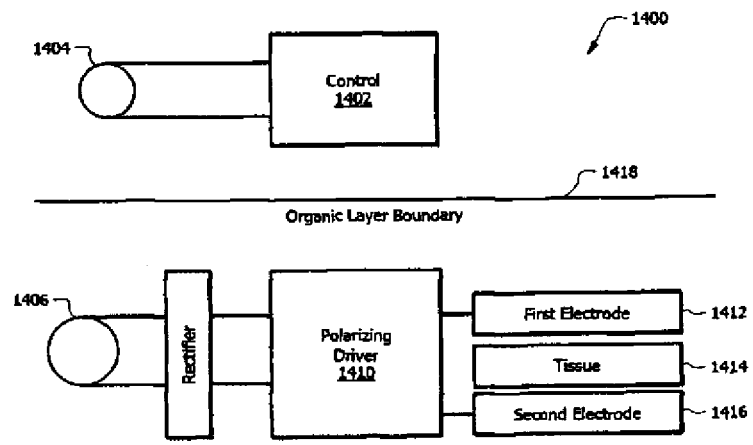
Figure 16:
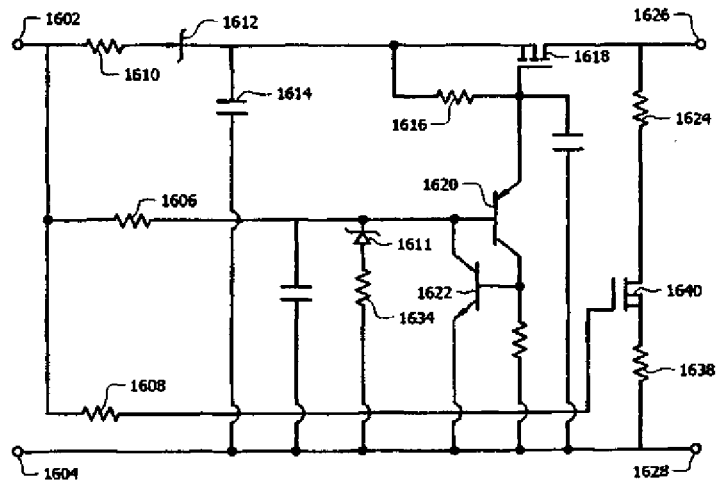
Figure 19C:
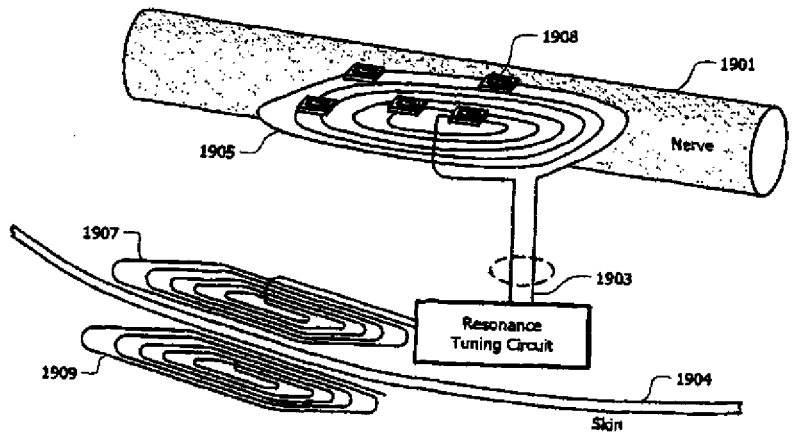

With reference to FIG. 37, a wireless micro-implant platform 3700 is shown. The platform includes an ASIC socket 3710 at one end of platform 3700. An LC resonant circuit is formed with a flat spiral microcoil 3704 and a capacitance 3706. Rectifier diodes 3708 may be positioned between the resonant circuit and the electrodes 3702.

Modifications and Variations

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

Although described to provide numerous features and advantages, the present embodiments could include minimal transponder circuits, for example, as a coil connected to a capacitance and a rectifier.

A voltage booster may be inserted immediately after the rectifier element 318 to boost the supply voltage available for stimulation and operation of integrated electronics beyond the limits of what might be generated by a miniaturized LC resonant tank circuit. The voltage booster may enable electrostimulation and other microtransponder operations using the smallest possible LC components, which may generate too little voltage, for example, less than 0.5 volts.

Examples of high efficiency voltage boosters include charge pumps and switching boosters using low-threshold Schottky diodes. However, it should be understood that any type of conventional high efficiency voltage booster may be utilized in this capacity as long as it can generate the voltage required by the particular application that the microtransponder is applied to.

Micro-transponders may not be physically linked while inside the cannula and stored in low temperature, such as around 40 C; the physically linked array may be formed after the injection by a biocompatible get like material, such as Matrigel™ (a product of BD Biosciences, Inc), that solidifies when exposed to higher temperature, such as body temperature, and the space between each micro-transponder may be adjusted by the pushing speed.

The shape of cannula, width, thickness and length vary for different purposes and clinic uses, for example, for deep tissue injection, the cannula may be made of strong material of sharper edge with a long extended body.

For example, in one embodiment, rather than an elongated strip, the linked microtransponders can be linked both longitudinally and latitudinally to form a geometric shape. The shapes can include squares, hexagons, rectangles, ovals, and circles.

The array can also be formed on a single substrate, with a chain or group of arrays constructed contemporaneously to form a single integrated structure. It may also be possible to construct linked arrays using a monofilament line as a string of arrays.

One such specific variation is dispensing with the subdermal/outer transfer coil to use a three coil power transmission arrangement. Power from the external coil would transmit to the subcutaneous/inner transfer coil which would power the microtransponder micro-coil. The interface between the two transfer coils can comprise radio frequency, low frequency, or direct current power. The wired connection between the two transfer coils can typically be coaxial or balanced line connection. The external coil and the subdermal/outer transfer coil can comprise paralleled coils at the skin surface. There can further be multiple internal drivers to power the microtransponders. The configuration can make use of spatial resolution. Finally, the described embodiment is a single power transfer through one internal tissue boundary, while the invention also extends to a double through two internal boundaries or potentially more.

It is also possible to vary the power source in the invention. The connection between the subdermal (or outer transfer) coil and subcutaneous (or inner transfer) coil does not necessarily have to be a connection at the resonant RF frequency. In alternative embodiments, it is contemplated that this power-transfer connection can be DC, or can be AC at a lower frequency than RF, or a non-resonating AC frequency of the microtransponder micro-coils. If the connection is DC, a power conversion stage would be included in the outer transfer coil circuitry, to convert the received RF power to DC. This can be quite similar to the AC-DC conversion which is normally used to charge up the storage capacitor for stimulation pulses. In this case, the inner transfer coil would need to contain or be combined with an oscillator of some sort, to generate an AC signal (for wireless coupling) from the received DC power. Similar adaptation is used if the connecting link operates at a lower AC frequency on non-resonating AC frequency, with a converter circuit generating an AC signal compatible with the microtransponder micro-coils and power circuits.

According to various embodiments, there is provided a method of providing electrical stimulation to tissue comprising: implanting one or more battery-free microtransponders, having spiral antennas integrated therewith, into tissue; wirelessly providing energy to said plurality of microtransponders; and stimulating said tissue with said energy.

According to various embodiments, there is provided a microtransponder system comprising an external interface unit; a battery-free internal transponder wirelessly receiving energy from said external interface unit; and a stimulation driver powered from said internal transponder.

According to various embodiments, there is provided a microtransponder comprising an antenna; an energy storage circuit connected to store energy received at said antenna; and a stimulator circuit connected to apply pulses to biocompatible electrodes.

According to various embodiments, there is provided a neural stimulation device comprising biocompatible electrodes providing stimulation energy to peripheral nerve tissue; and an inductively coupled stimulation energy source connected to said biocompatible electrodes.

According to various embodiments, there is provided a method for providing neural stimulation comprising receiving energy with an implanted tank circuit; and providing intermittent stimulation pulses from said implanted tank circuit to biocompatible electrodes in contact with neural tissue.

According to various embodiments, there is provided a method of providing neural stimulation comprising receiving externally generated energy by inductive coupling with a flat spiral coil to generate stimulation energy; and providing said stimulation energy to peripheral nerve tissue.

According to various embodiments, there is provided a method and system for providing electrical stimulation to tissue includes implanting one or more battery-free microtransponders having spiral antennas into tissue. Energy is provided wirelessly to the plurality of microtransponders. Tissue is stimulated using the energy.

The following applications may contain additional information and alternative modifications: Ser. No. 61/088,099 filed Aug. 12, 2008 and entitled "In Vivo Tests of Switched-Capacitor Neural Stimulation for Use in Minimally-Invasive Wireless Implants; Ser. No. 61/088,774 filed Aug. 15, 2008 and entitled "Micro-Coils to Remotely Power Minimally Invasive Microtransponders in Deep Subcutaneous Applications"; Ser. No. 61/079,905 filed Jul. 8, 2008 and entitled "Microtransponders with Identified Reply for Subcutaneous Applications"; Ser. No. 61/089,179 filed Aug. 15, 2008 and entitled "Addressable Micro-Transponders for Subcutaneous Applications"; Ser. No. 61/078,954 filed Jul. 8, 2008 and entitled "Neuroplastivity Enhancement"; Ser. No. 61/077,648 filed Jul. 2, 2008 and entitled "Treatment of Tinnitus with Vegus Nerve Stimulation"; Ser. No. 61/079,004 filed Jul. 8, 2008 and entitled "Microtransponder Array with Biocompatible Scaffold"; Ser. No. 61/083,290 filed Jul. 24, 2008 and entitled "Minimally Invasive Microtransponders for Subcutaneous Applications" Ser. No. 61/086,116 filed Aug. 4, 2008 and entitled "Tintinnitus Treatment Methods and Apparatus"; Ser. No. 61/086,309 filed Aug. 5, 2008 and entitled "Wireless Neurostimulators for Refractory Chronic Pain"; Ser. No. 61/086,314 filed Aug. 5, 2008 and entitled "Use of Wireless Microstimulators for Orofacial Pain"; Ser. No. 61/090,408 filed Aug. 20, 2008 and entitled "Update: In Vivo Tests of Switched-Capacitor Neural Stimulation for Use in Minimally-Invasive Wireless Implants"; Ser. No. 61/091,908 filed Aug. 26, 2008 and entitled "Update: Minimally Invasive Microtransponders for Subcutaneous Applications"; Ser. No. 61/094,086 filed Sep. 4, 2008 and entitled "Microtransponder MicroStim System and Method"; Ser. No. 12/323,904, filed Nov. 26, 2008 and entitled "Transfer Coil Architecture"; Ser. No. 12/323,934, filed Nov. 26, 2008 and entitled "Implantable Driver with Charge Balancing"; Ser. No. 12/323,952, filed Nov. 26, 2008 and entitled "A Biodelivery System for Microtransponder Array"; Ser. No. 12/323,969, filed Nov. 26, 2008 and entitled "Implanted Driver with Resistive Charge Balancing"; Ser. No. 12/324,000, filed Nov. 26, 2008 and entitled "Array of Joined Microtransponders for Implantation"; and Ser. No. 12/324,044, filed Nov. 26, 2008 and entitled "Implantable Transponder Pulse Stimulation Systems and Methods" and all of which are incorporated by reference herein.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A linear implantable device array comprising:
   a plurality of implantable devices, each of the plurality of implantable devices comprising: and inductive antenna; an energy storage circuit connected to the inductive antenna and storing energy received at the inductive antenna; and a stimulator circuit connected to the energy storage circuit and applying pulses to a plurality of biocompatible electrodes; and
   connecting material, connecting each of the implantable devices to form a physically-connected array of implantable devices such that the electrodes of each of the implantable devices are at a fixed distance apart from the electrodes of another of the implantable devises, wherein the implantable devices are collectively housed in a cannula, and wherein the cannula is configured to implant the physically-connected array of implantable devices into tissue at a single injection point.

2. A method of providing electrical stimulation to tissue comprising:
   implanting into tissue an array of independent implantable devices, each independent implantable device including an inductive antenna and electrodes, wherein each of the independent implantable devices is physically connected to at least another one of the independent implantable devices in the array with a connecting material such that the electrodes of one of the independent implantable devices are held at a fixed distance apart from the electrodes of another one of the independent implantable devices by the connecting material, and wherein the physically-connected array of independent implantable devices is housed within a cannula prior to being implanted into the tissue;
   providing inductive energy through skin to each of the inductive antennas at the same time using a single control device;
   communicating instructions from the single control device to each of the independent implantable devices using the inductive energy;
   receiving response replies from each of the independent implantable devices by the single control device; and
   stimulating the tissue using one or more of the independent implantable devices in accordance with the instructions.

3. The method of claim 2, wherein implanting into tissue the physically-connected array of independent implantable devices comprises:
   inserting the cannula into the tissue at a single injection point; and
   retracting the cannula from the tissue while simultaneously expelling the physically-connected array of independent implantable devices from the cannula into the tissue at the single injection point.

* * * * *

UNITED STATES PATENT AND TRADEMARK OFFICE
CERTIFICATE OF CORRECTION

Page 1 of 12

PATENT NO. : 8,457,757 B2
APPLICATION NO. : 12/323854
DATED : June 4, 2013
INVENTOR(S) : Cauller et al.

It is certified that error appears in the above-identified patent and that said Letters Patent is hereby corrected as shown below:

On the Title Page

Page 5, item [56] Column 1, Line 18 - Reference should read as follows:
"EZstim II Peripheral Nerve Locator and Stimulator, Model ES400, Operator's Manual, Live-Tech, Inc., 2005, 29 pages."

In the Drawings

Drawing Sheet 2 of 36, FIG. 2, should be replaced with the following:

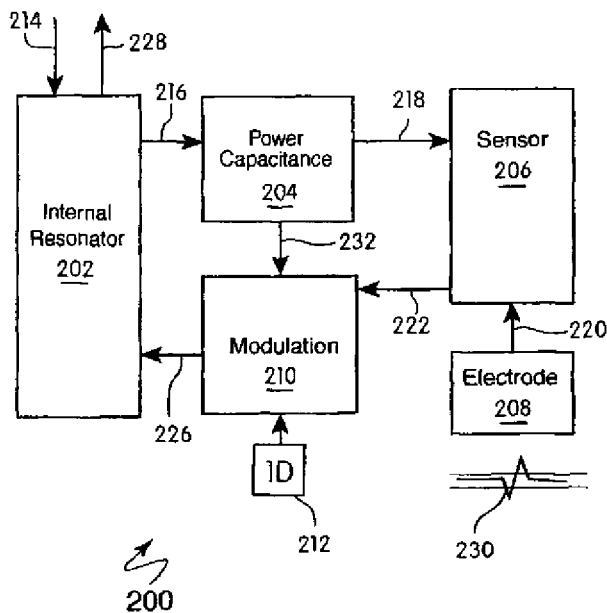

Fig. 2

Signed and Sealed this
Eighth Day of July, 2014

Michelle K. Lee
*Deputy Director of the United States Patent and Trademark Office*

CERTIFICATE OF CORRECTION (continued)

U.S. Pat. No. 8,457,757 B2

Drawing Sheet 3 of 36, FIG. 3, should be replaced with the following:

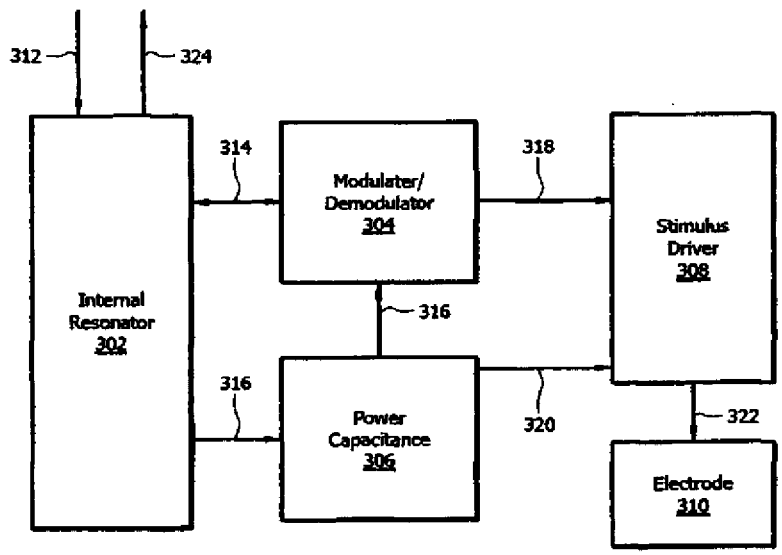

FIG. 3

Drawing Sheet 4 of 36, FIG. 4, should be replaced with the following:

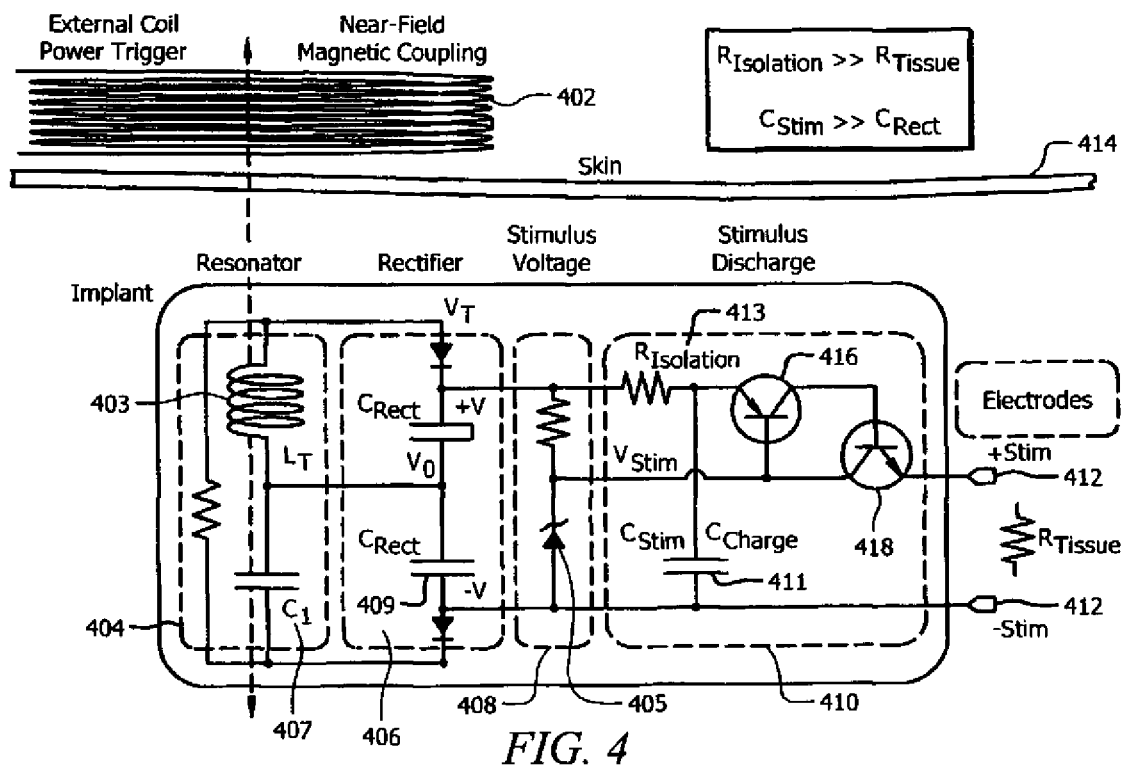

FIG. 4

CERTIFICATE OF CORRECTION (continued)
U.S. Pat. No. 8,457,757 B2

Drawing Sheet 6 of 36, FIGS. 6 and 7, should be replaced with the following:

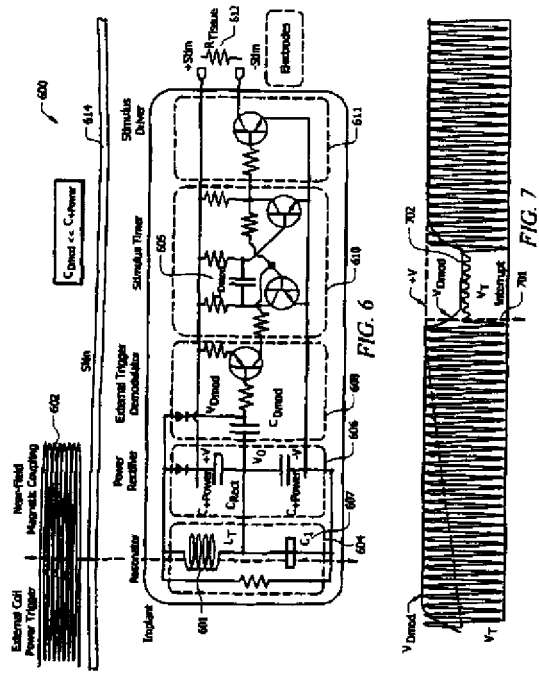

Drawing Sheet 9 of 36, FIG. 10, should be replaced with the following:

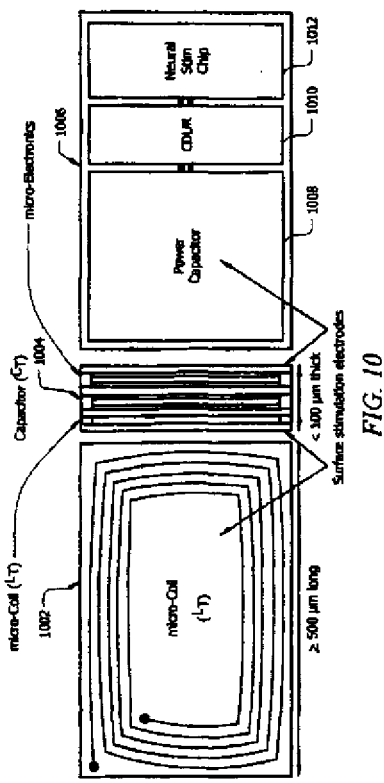

Drawing Sheet 11 of 36, FIG. 12, should be replaced with the following:

Drawing Sheet 13 of 36, FIG. 14, should be replaced with the following:

Drawing Sheet 15 of 36, FIG. 16, should be replaced with the following:

Drawing Sheet 19 of 36, FIG. 19C, should be replaced with the following:

Drawing Sheet 20 of 36, FIG. 20, should be replaced with the following:

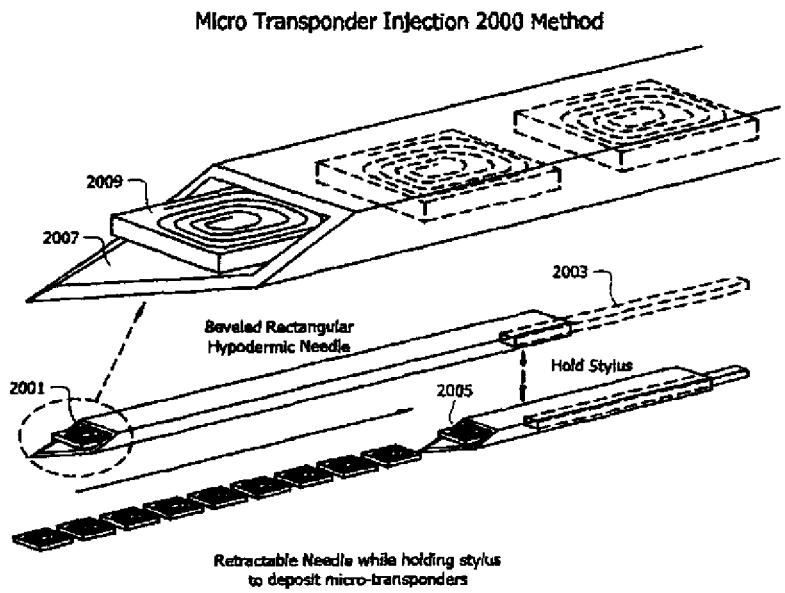

FIG. 20

In the Specification

Column 5, Lines 27-49, should read as follows:
"With reference to FIG. 2, a block diagram depicts a sensing microtransponder 200, in accordance with an embodiment. An internal resonator 202 receives an operation signal 214, where the operation signal 214 has been transmitted inductively by an external resonator (not shown). The operation signal 214 may include instructions, commands, address data or any other suitable data. The internal resonator 202 provides a power signal 216 to a power capacitance 204. The power capacitance 204 may subsequently provide power 218 to an impulse sensor 206, a modem 210, or any appropriate electrical component. The impulse sensor 206 is connected to a sensor electrode 208 placed proximate to peripheral nerve tissue 230. When an impulse passes through the peripheral nerve tissue 230, a charge is generated on the sensor electrode 208. The sensor electrode 208 provides a signal 220 to the impulse sensor 206. The impulse sensor 206 provides a signal 222 to an identification modulator 210. The identification modulator 210 receives a power signal 232 from the power capacitance 204. The identification modulator 210 generates a modulated identification signal 226 using identification data 212. The internal resonator 202 generates a communication signal 228. An external resonator (not shown) receives the communication signal 228."

Column 5, Line 50, through Column 6, Line 3, should read as follows:
"With reference to FIG. 3, a block diagram depicts a microtransponder 300 including data reply in accordance with an embodiment. An internal resonator 302 receives an operation signal 312 from an external resonator (not shown). The operation signal 312 may include data, such as identification information, addressing, commands, instruction or other suitable data. The internal resonator 302 provides a received signal to a modem 304. The internal resonator 302 provides a power signal 316 to a power capacitance 306. The modem 304 demodulates data 318 that has been modulated on the received signal 314. The data 318, typically a trigger signal, is provided to the stimulus driver 308. The stimulus driver 308 receives a power signal 320 from a power capacitance 306. The stimulus driver 308 provides stimulation energy 322 to a stimulation electrode 310 in response to receiving the trigger signal 318. The modem 304 receives power signal 316 from the power capacitance 306. Modem 304 generates a data reply signal 314 in response to data 318. The internal resonator 302 generates a communication signal 324. An external resonator (not shown) receives the communication signal 324."

Column 6, Lines 55-63, should read as follows:
"The stimulus peak amplitude and duration are largely determined by the effective tissue resistance, independent of the applied power intensity. Effective tissue resistance may vary depending on the type of tissue 414 being stimulated, for example, skin, muscle, fat, etc. However, increasing the power may increase the stimulation frequency by reducing the time required to charge the stimulation capacitor 411 to the stimulus voltage Vstim."

Column 7, Lines 52-61, should read as follows:
"The resonator element 604 is coupled to a rectifier element 606, which is in turn coupled to the external trigger demodulator element 608, the stimulus timer element 610 and the stimulus driver element 611. The rectifier element 606 and the stimulus timer element 610 are both coupled in parallel to power capacitors (Cpower). In addition, the stimulus driver element 611 is coupled to electrodes 612, typically formed of gold or a platinum iridium alloy, thereby electrically connecting the stimulus driver element 611 to neural conduction tissue 614, such as axons."

Column 10, Lines 17-39, should read as follows:
"In an exemplary embodiment, a gate of the spike sensor JFET 916 may be coupled via the neural spike electrode 919 to the neural transmission tissue, such as neurons. The gate of the spike sensor JFET 916 may be chosen to have a threshold voltage that is within a voltage range of those signals produced by the neural axons. In this manner, during spike phases of the neural axons, the gate of the spike sensor JFET 916 becomes open, thereby closing the circuit.

Once the circuit closes, the external RF electromagnetic field generates an LC response in the coupled inductor 922 and capacitor 918, which then resonate with the external RF electromagnetic field with its resonance matching the modulating frequency of the RF electromagnetic field.

The LC characteristic of the circuit, as well as the threshold voltage of the gate of spike sensor JFET 916 can be chosen to determine a unique modulation within the coupled inductor 922 and capacitor 918 thereby providing a desired ID signal for the microtransponder. Accordingly, the spike sensor JFET 916 provides the RF identity modulator 917 with a trigger signal for generating desired RF signals. The ID signal may indicate the nature of the neural activity in the vicinity of the microtransponder as well as the location of the neural activity within the body."

CERTIFICATE OF CORRECTION (continued)
U.S. Pat. No. 8,457,757 B2

Column 11, Lines 12-45, should read as follows:
"FIG. 9 is a functional schematic of a complete microtransponder for sensing and/or stimulating neural activity, in accordance with one embodiment. The circuit is designed for dependent triggering operation (synchronous stimulation). The microtransponder 900 includes electrical components adapted to electrically interface with neurons of peripheral nerves. The microtransponder 900 further includes electrical components which enable the microtransponder to wirelessly interact with systems external to the microtransponder. Such systems may include other transponders implanted within the body or external coils and/or a receiver. The wireless capabilities of the microtransponder 900 enable the delivery of electrical signals to and/or from the peripheral nerves. These include electrical signals indicative of neural spike signals and/or signals configured to stimulate peripheral nerves distributed throughout the subcutaneous tissue.
Accordingly, the microtransponder 900 includes the micro-coil 922 coiled about a central axis 912. The micro-coil 922 is coupled in parallel to a capacitor 911 and to an RF identity modulator 917 via a switch 915.

The RF identity modulator 917 is coupled to an RF identity and trigger demodulator 913, which in turn is coupled to a rectifier 914. The rectifier 914 is coupled to a spike sensor trigger 916 and to a stimulus driver 920. The rectifier 914 and the spike sensor 916 are both coupled in parallel to a capacitor 918. In addition, the spike sensor 916 is coupled to a neural spike electrode 919, thereby electrically connecting the spike sensor 916 to neural transmission tissue (neurons). Similarly, the neural stimulus electrode 921 also connects the stimulus driver 920 to neural conduction tissue (axons). The spike sensor 916 is made up of one or more junction field effect transistors (JFET). As will be appreciated by those of ordinary skill in the art, the JFET may include metal oxide semiconductors field effect transistors (MOSFETS)."

Column 11, Line 57, through Column 12, Line 13, should read as follows:
"One configuration of the above components, as depicted by FIG. 9, enables the microtransponder to operate as an autonomous wireless unit, capable of detecting spike signals generated by peripheral nerves, and relaying such signals to external receivers for further processing. It should be understood that the microtransponder performs such operations while being powered by external RF electromagnetic signals. The above-mentioned capabilities are facilitated by the fact that magnetic fields are not readily attenuated by human tissue. This enables the RF electromagnetic signals to sufficiently penetrate the human body so that signals can be received and/or transmitted by the microtransponder. In other words, the micro-coil 922 is designed and configured to magnetically interact with the RF field whose magnetic flux fluctuates within the space encompassed by the micro-coil 922. By virtue of being inductors, the micro-coils 922 convert the fluctuations of the magnetic flux of the external RF field into alternating electrical currents, flowing within the micro-coil 922 and the circuit. The alternating current is routed, for example, into the rectifier 914, which converts the alternating current into direct current. The direct current may then be used to charge the capacitor 918, thereby creating a potential difference across the JFET of the spike sensor 916."

Column 12, Lines 14-46, should read as follows:
"In an exemplary embodiment, a gate of the spike sensor 916 JFET may be coupled via the neural spike electrode 919 to the neural transmission tissue (neurons). The gate of the spike sensor 916 JFET may be chosen to have a threshold voltage that is within a voltage range of those signals produced by the neural axons. In this manner, during spike phases of the neural axons, the gate of the spike sensor 916 becomes open, thereby closing the circuit. Once the circuit closes, the external RF electromagnetic field generates an LC response in the coupled inductor 922 and capacitor 918, which then resonate with the external RF electromagnetic field, with its resonance matching the modulating frequency of the RF electromagnetic field. The LC characteristic of the circuit, as well as the threshold voltage of the gate of spike sensor 916 JFET, can be chosen to determine a unique modulation within the coupled micro-coil (i.e. inductor) 922 and capacitor 918, thereby providing a identifying signal for the microtransponder. Accordingly, the spike sensor 16 JFET provides the RF identity modulator 917 with a unique trigger signal for generating desired RF signals. The identity signal may indicate the nature of the neural activity in the vicinity of the microtransponder, as well as the location of the neural activity within the body as derived from the specific identified microtransponder position.

It should be appreciated that the RF capabilities, as discussed above with respect to the circuit, can render the microtransponder a passive device which reacts to incoming carrier RF signals. That is, the circuit does not actively emit any signals, but rather reflects and/or scatters the electromagnetic signals of the carrier RF wave to provide signals having specific modulation. In so doing, the circuit draws power from a carrier radio frequency (RF) wave to power the electrical components forming the circuit."

Column 12, Lines 47-63, should read as follows:
"While the above-mentioned components illustrated in FIG. 9 may be used to receive signals from the microtransponder in response to spike signals generated by peripheral nerves, other components of circuit of the microtransponder may include components for stimulating the peripheral nerves using the external RF signals. For example, the RF signals received by the micro-coil 922 may be converted to electrical signals, via the RF identity and trigger demodulator 913, so as to provide sufficient current and voltage for stimulating the peripheral nerves. Hence, the RF identity and trigger demodulator 913 derives power from an RF carrier signal for powering the stimulus driver 920, which delivers electrical signals suitable for stimulating neural conduction tissue (axons). This may be used to treat nerves that are damaged or that are otherwise physiologically deficient. Because of the nature of the identifying signal, a microtransponder can be selectively activated to provide electrostimulation."

Column 14, Lines 5-24, should read as follows:
"When a stimulation signal is applied to living tissue at frequencies higher than two hertz, the tissue typically becomes polarized, exhibiting an inherent capacitance 1226 by storing a persistent electrical charge. In order to reduce the polarization effect, a depolarization switch 1222 is connected between the electrodes 1218 and 1220. The gate terminal of the depolarization switch 1222 is connected to the oscillating trigger voltage VT, so that once each cycle, the depolarization switch shorts the electrodes 1218 and 1220 and reduces the charge stored in the inherent tissue capacitance 1226. The timing of the depolarization switch 1222 permits the stimulation pulse to be substantially discharged before the depolarization switch 1222 closes and shorts the electrodes 1218 and 1220. Similarly, the depolarization switch 1222 is timed to open before a subsequent stimulation pulse arrives. The timing of the depolarization switch 1222 may be generated relative to the timing of the stimulation pulse. The timing may be accomplished using digital delays, analog delays, clocks, logic devices or any other suitable timing mechanism."

Column 14, Lines 39-63, should read as follows:
"With reference to FIG. 14, a block diagram depicts a depolarizing microtransponder system 1400 in accordance with an embodiment. A control component energizes an external resonator element 1404 positioned externally relative to an organic layer boundary 1418. Energized, the external resonator element 1404 resonates energy at a resonant frequency, such as a selected RF. Internal resonator element 1406, positioned internally relative to an organic layer boundary 1418, is tuned to resonate at the same resonant frequency, or a harmonically related resonant frequency as the external resonator element 1404. Energized by the resonating energy, the internal resonator element 1406 generates pulses of energy rectified by a rectifier. The energy may typically be stored and produced subject to timing controls or other forms of control. The energy is provided to the depolarizing driver 1410. A first electrode 1412 is polarized relative to a second electrode 1416 so that current is drawn through the tissue 1414 being stimulated, proximate to the electrode 1412 and 1416. The first electrode 1412 is polarized relative to the second electrode 1416 in the opposite polarization to draw an oppositely directed current through the tissue 1414, depolarizing the tissue 1414. The electrodes 1412 and 1416 may be typically made of gold or a platinum iridium alloy, or any other suitable material."

Column 15, Line 45, through Column 16, Line 2, should read as follows:
"With reference to FIG. 17, a circuit diagram depicts a depolarization driver circuit 1700, in accordance with an embodiment. A trigger signal is applied between electrodes 1702 and 1704. A charge capacitance 1714 is charged on the charge capacitance 1714. Schottky diode 1712 prevents the backflow of stimulus charge during the trigger phase. The charge rate is regulated by resistances 1710, 1706 and 1708. Resistances 1706 and 1708 form a voltage divider so that a portion of the trigger signal operate the bipolar switches 1720 and 1722. The trigger signal closes switch 1718, connecting the pulse between electrodes 1726 and 1728. A depolarization resistance 1724 is connected to a bipolar switch 1730 between the electrodes 1726 and 1728 to balance the charge stored in the tissue between the electrodes 1726 and 1728 between pulses. The specific breakdown voltage of the optional Zener diode 1711 provides for auto-triggering setting the upper limit of the voltage divider, at which point the bipolar switches are triggered by any further increase in the stimulus voltage. In addition to providing this auto-triggering feature for the purpose of asynchronous stimulation, the particular breakdown voltage of this Zener diode 1711 sets the maximum stimulus voltage. Otherwise the stimulus voltage is a function of the RF power level reaching the transponder from the external reader coil when the stimulus is triggered."

Column 18, Lines 13-29, should read as follows:
"FIG. 20 is an illustration of how wireless microtransponders can be implanted using a beveled rectangular hypodermic needle, in accordance with one embodiment. As shown, the needle 2005 is curved to conform to the transverse cervical curvature (bevel concave) and without further dissection is passed transversely in the subcutaneous space across the base of the affected peripheral nerve tissue. Rapid insertion usually negates the need for even a short active general anesthetic once the surgeon becomes familiar with the technique. Following the placement of the microtransponders 2009 by the needle 2005, the needle 2005 is carefully withdrawn and the electrode placement and configuration is evaluated using intraoperative testing. Electrostimulation is applied using a temporary RF transmitter placed proximate to the location where the microtransponders 2009 are implanted, so the patient can report on the stimulation location, intensity, and overall sensation."

Column 20, Lines 44-52, should read as follows:
"FIG. 24(a) shows a preloaded injection system with a relaxed spring. FIG. 24(b) shows that after inserting the needle/cannula 2405 into the tissue, handle 2413 is pushed compressing the spring 2415 and stylet 2403 and pushing microtransponder array 2401 into the tissue. After the injection into the tissue, a handle holder is used to retract cannula 2405, leaving the injection array in the tissue. FIG. 25 shows an example look of the injection system immediately after the microtransponder ejection."

Column 20, Lines 53-61, should read as follows:
"Materials for the construction of the injection system are biocompatible, for example the cannula and stylet can be stainless steel and the handle and the handle holder can be acrylonitrile butadiene styrene (ABS), polycarbonate, or polyurethane. The stylet may also be made of bio-compatible plastics. Sterilization can be conducted and verified according to standard GMP procedure required by FDA for the intended production environment and processes and purposes."

Column 21, Lines 39-51, should read as follows:
"Another embodiment of the microtransponder array is shown in FIGS. 28 and 29. The core strip 2803 is a strong strip containing an embedded array of individual microtransponders, where the superior and inferior electrodes of microtransponders are exposed through "windows" 2807. Electrode surfaces and strip may be coated with a lubricious, protein adsorption preventing, "stealth" material. The core strip is then embedded within a porous scaffold/matrix 2801 that the scaffolding will extend into the "windows." Other durable and more flexible material than SU8 can be used, and embedded microtransponders can be better protected. Electrodes of microtransponders 2805 can be totally isolated from proteins/tissues, but still affect ions in solution."

Column 22, Lines 53-63, should read as follows:
"With reference to FIG. 34, a block diagram depicts an addressable microtransponder system 3400. A resonator 3402 transmits resonant energy in accordance to instructions provided by a control 3404. The microtransponders 3406, 3408, 3410, 3412, 3414, 3416, 3418, 3420, 3422, 3424 and 3426 may be arranged in addressable groups. For example, microtransponders 3406, 3408, 3410 and 3412 may form a first group, addressable by a group address. Microtransponders 3414, 3416, 3418 and 3420 may form a second group addressable by a second group address. Microtransponders 3422, 3424 and 3426 my form a third group."

Column 23, Lines 26-33, should read as follows:
"A voltage booster may be inserted immediately after the rectifier element to boost the supply voltage available for stimulation and operation of integrated electronics beyond the limits of what might be generated by a miniaturized LC resonant tank circuit. The voltage booster may enable electro-stimulation and other microtransponder operations using the smallest possible LC components, which may generate too little voltage, for example, less than 0.5 volts."
Column 23, Lines 41-48, should read as follows:

"Microtransponders may not be physically linked while inside the cannula and stored in low temperature, such as around 40°C; the physically linked array may be formed after the injection by a biocompatible gel like material, such as Matrigel™ (a product of BD Biosciences, Inc), that solidifies when exposed to higher temperature, such as body temperature, and the space between each microtransponder may be adjusted by the pushing speed."

In the Claims:

Column 26, Lines 3-19, Claim 1, should read as follows:
"1. A linear implantable device array comprising:
a plurality of implantable devices, each of the plurality of implantable devices comprising:
an inductive antenna;
    an energy storage circuit connected to the inductive antenna and storing energy received at the inductive antenna; and a stimulator circuit connected to the energy storage circuit and applying pulses to a plurality of biocompatible electrodes; and
connecting material, connecting each of the implantable devices to form a physically-connected array of implantable devices such that the electrodes of each of the implantable devices are at a fixed distance apart from the electrodes of another of the implantable devices, wherein the implantable devices are collectively housed in a cannula, and wherein the cannula is configured to implant the physically-connected array of implantable devices into tissue at a single injection point."